United States Patent
Pekna et al.

(10) Patent No.: US 11,266,715 B2
(45) Date of Patent: Mar. 8, 2022

(54) C3A RECEPTOR AGONISTS FOR USE AGAINST ISCHEMIC BRAIN INJURY, STROKE, TRAUMATIC BRAIN INJURY, SPINAL CORD INJURY AND NEURODEGENERATIVE DISORDERS

(71) Applicants: Marcela Pekna, Askim (SE); Milos Pekny, Askim (SE); Anna Stokowska, Gothenburg (SE)

(72) Inventors: Marcela Pekna, Askim (SE); Milos Pekny, Askim (SE); Anna Stokowska, Gothenburg (SE)

( * ) Notice: Subject to any disclaimer, the term of this patent is extended or adjusted under 35 U.S.C. 154(b) by 87 days.

(21) Appl. No.: 16/462,697

(22) PCT Filed: Nov. 20, 2017

(86) PCT No.: PCT/EP2017/079811
§ 371 (c)(1),
(2) Date: May 21, 2019

(87) PCT Pub. No.: WO2018/091715
PCT Pub. Date: May 24, 2011

(65) Prior Publication Data
US 2019/0351016 A1 Nov. 21, 2019

(30) Foreign Application Priority Data
Nov. 21, 2016 (GB) .................................. 1619637

(51) Int. Cl.
| | | |
|---|---|---|
| A61K 38/04 | (2006.01) | |
| A61K 38/08 | (2019.01) | |
| A61K 38/02 | (2006.01) | |
| A61K 38/03 | (2006.01) | |
| A61K 38/10 | (2006.01) | |
| A61K 38/17 | (2006.01) | |
| C07K 14/47 | (2006.01) | |
| C07K 14/00 | (2006.01) | |
| C07K 11/00 | (2006.01) | |
| C07K 7/00 | (2006.01) | |
| A61P 9/10 | (2006.01) | |
| A61P 25/28 | (2006.01) | |
| A61K 9/00 | (2006.01) | |
| A61K 9/06 | (2006.01) | |
| A61K 47/02 | (2006.01) | |
| A61K 47/32 | (2006.01) | |
| A61K 47/38 | (2006.01) | |

(52) U.S. Cl.
CPC ........ *A61K 38/1725* (2013.01); *A61K 9/0043* (2013.01); *A61K 9/06* (2013.01); *A61K 38/04* (2013.01); *A61K 38/08* (2013.01); *A61K 38/10* (2013.01); *A61K 47/32* (2013.01); *A61K 47/38* (2013.01); *A61P 9/10* (2018.01); *A61P 25/28* (2018.01); *C07K 14/472* (2013.01)

(58) Field of Classification Search
None
See application file for complete search history.

(56) References Cited

U.S. PATENT DOCUMENTS

| | | |
|---|---|---|
| 6,715,485 B1 | 4/2004 | Djupesland |
| 8,001,963 B2 | 8/2011 | Giroux |
| 2008/0188528 A1 | 8/2008 | Biediger et al. |
| 2014/0329761 A1 | 11/2014 | Woodruff et al. |
| 2017/0043109 A1 | 2/2017 | Hoekman et al. |

FOREIGN PATENT DOCUMENTS

| | | |
|---|---|---|
| WO | 2002/44737 A2 | 6/2002 |
| WO | 2005/101013 A2 | 10/2005 |
| WO | 2012/174591 A1 | 12/2012 |
| WO | 2014/152391 A1 | 9/2014 |

OTHER PUBLICATIONS

Tanaka et al., PLoS One 11:e0159150 (11 pages) (Sep. 2016) (Year: 2016).*
Hagberg et al., The role of inflammation in perinatal brain injury, Nat. Rev. Neurol. 11:192-208 (2015).
Hanson et al., Intranasal delivery bypasses the blood-brain barrier to target therapeutic agents to the central nervous system and treat neurodegenerative disease, BMC Neurosci. 9 Suppl 3:S5 (2008).
Hedtjarn et al., Interleukin-18 involvement in hypoxic-ischemic brain injury, J. Neurosci. 22:5910-5919 (2002).
Heese et al., Inflammatory signals induce neurotrophin expression in human microglial cells, J. Neurochem. 70:699-707(1998).
Hilton et al., Re-Establishment of Cortical Motor Output Maps and Spontaneous Functional Recovery via Spared Dorsolaterally Projecting Corticospinal Neurons after Dorsal Column Spinal Cord Injury in Adult Mice, The Journal of neuroscience. 36:4080-4092 (2016).
Hiu et al., Enhanced phasic GABA inhibition during the repair phase of stroke: a novel therapeutic target, Brain. 139:468-480 (2016).
Horner et al., Regenerating the damaged central nervous system, Nature. 407:963-970 (2000).

(Continued)

*Primary Examiner* — Thea D'Ambrosio
(74) *Attorney, Agent, or Firm* — Marshall, Gerstein & Borun LLP

(57) ABSTRACT

The present invention relates to use of a human C3a receptor agonist in the manufacture of a medicament for the treatment or prevention of an ischemic brain injury, wherein the medicament is formulated for intranasal delivery, human C3a receptor agonist for such use, as well as devices for intranasal administration comprising a human C3a receptor agonist and kits comprising such devices.

14 Claims, 7 Drawing Sheets
Specification includes a Sequence Listing.

(56) References Cited

OTHER PUBLICATIONS

Hou et al., Synaptic vesicle proteins and neuronal plasticity in adrenergic neurons, Neurochem. Res. 25:1275-1300 (2000).
Huang et al., Neuronal protection in stroke by an sLex-glycosylated complement inhibitory protein, Science. 285:595-599 (1999).
Hung et al., Astrocytic GAP43 Induced by the TLR4/NF-kappaB/STAT3 Axis Attenuates Astrogliosis-Mediated Microglial Activation and Neurotoxicity, J. Neurosci. 36:2027-2043 (2016).
Illum et al., Intranasal delivery to the central nervous system, Blood-Brain Barrier in Drug Discovery: Optimizing Brain Exposure of CNS Drugs and Minimizing Brain Side Effects for Peripheral Drugs. 535-565, (2015).
Intellectual Property Office Search Report, GB1619637.0, dated Aug. 8, 2017.
International Preliminary Report on Patentability for Corresponding International Application No. PCT/EP2017/079811, dated May 31, 2019, 11 pages.
International Search Report and Written Opinion for Corresponding International Application No. PCT/EP2017/079811, dated Feb. 13, 2018, 15 pages.
Jander et al., Lymphocytic infiltration and expression of intercellular adhesion molecule-1 in photochemically induced ischemia of the rat cortex, J. Cereb. Blood Flow Metab. 15:42-51 (1995).
Jantzie et al., Doxycycline reduces cleaved caspase-3 and microglial activation in an animal model of neonatal hypoxia-ischemia, J. Cereb. Blood Flow Metab. 25:314-324 (2005).
Jarlestedt et al., Receptor for complement peptide C3a: a therapeutic target for neonatal hypoxic-ischemic brain injury, FASEB J. 27:3797-3804 (2013).
Jarlestedt et al., Trace fear conditioning detects hypoxic-ischemic brain injury in neonatal mice, Dev. Neurosci. 33:222-230 (2011).
Jauneau et al., Interleukin-1beta and anaphylatoxins exert a synergistic effect on NGF expression by astrocytes, J. Neuroinflammation. 3:8 (2006).
Jinsmaa et al., Anti-analgesic and anti-amnesic effect of complement C3a, Life Sciences. 67:2137-2143 (2000).
Jones, Multiple synapse formation in the motor cortex opposite unilateral sensorimotor cortex lesions in adult rats, J. Comp. Neurol. 414:57-66 (1999).
Kildsgaard et al., Cutting edge: targeted disruption of the C3a receptor gene demonstrates a novel protective anti-inflammatory role for C3a in endotoxin-shock, J. Immunol. 165:5406-5409 (2000).
Kind, Fall in rectal temperature as an indication of anaphylactic shock in the mouse, J. Immunol. 74:387-390 (1955).
Klos et al., International Union of Basic and Clinical Pharmacology, [corrected]. LXXXVII. Complement peptide C5a, C4a, and C3a receptors, The American Society for Pharmacology and Experimental Therapeutics. 65:500-543 (2013).
Klos et al., The role of the anaphylatoxins in health and disease, Mol. Immunol. 46:2753-2766 (2009).
Kurinczuk et al., Epidemiology of neonatal encephalopathy and hypoxic-ischaemic encephalopathy, Early Hum. Dev. 86:329-338 (2010).
Lee et al., Photochemically induced cerebral ischemia in a mouse model, Surg. Neurol. 67:620-625 (2007).
Leger et al., Object recognition test in mice, Nat. Protoc. 8:2531-2537 (2013).
Leke et al., Impairment of the organization of locomotor and exploratory behaviors in bile duct-ligated rats, PLoS One. 7:e36322 (2012).
Li et al., An age-related sprouting transcriptome provides molecular control of axonal sprouting after stroke, Nat. Neurosci. 13:1496-1504 (2010).
Li et al., Growth-associated gene and protein expression in the region of axonal sprouting in the aged brain after stroke, Neurobiol. Dis. 23:362-373 (2006).
Lian et al., Astrocyte-Microglia Cross Talk through Complement Activation Modulates Amyloid Pathology in Mouse Models of Alzheimer's Disease, J. Neurosci. 36: 577-589 (2016).
Lian et al., NFkappaB-activated astroglial release of complement C3 compromises neuronal morphology and function associated with Alzheimer's disease, Neuron. 85:101-115 (2015).
Liauw et al., Thrombospondins 1 and 2 are necessary for synaptic plasticity and functional recovery after stroke, J. Cereb. Blood Flow Metab. 28:1722-1732 (2008).
Lin et al., Intranasal administration of IGF-1 attenuates hypoxic-ischemic brain injury in neonatal rats, Exp. Neurol. 217:361-370 (2009).
Lin et al., Synthesis and transport of GAP-43 in entorhinal cortex neurons and perforant pathway during lesion-induced sprouting and reactive synaptogenesis, Molecular Brain Research. 14:147-153 (1992).
Loane et al., Role of microglia in neurotrauma, Neurotherapeutics: the journal of the American Society for Experimental NeuroTherapeutics. 7:366-377 (2010).
Lochhead et al, Intranasal delivery of biologies to the central nervous system, Adv. Drug. Deliv. Rev. 64:614-628 (2012).
Lu et al., Combinatorial therapy with neurotrophins and cAMP promotes axonal regeneration beyond sites of spinal cord injury, J. Neurosci. 24:6402-6409 (2004).
Luke et al., Unilateral ischemic sensorimotor cortical damage induces contralesional synaptogenesis and enhances skilled reaching with the ipsilateral forelimb in adult male rats, Synapse. 54:187-199 (2004).
Marlier et al., Mechanisms and Functional Significance of Stroke-Induced Neurogenesis, Frontiers in Neuroscience. 9:458 (2015).
Meredith et al., Intranasal delivery of proteins and peptides in the treatment of neurodegenerative diseases, The AAPS Journal. 17(4):780-787 (2015).
Mestriner et al., Skilled reaching training promotes astroglial changes and facilitated sensorimotor recovery after collagenase-induced intracerebral hemorrhage, Experimental Neurology. 227:53-61 (2011).
Micheva et al., Single-synapse analysis of a diverse synapse population: proteomic imaging methods and markers, Neuron. 68:639-653 (2010).
Misra et al., Drug Delivery Systems from Nose to Brain, Current Pharmaceutical Biotechnology. 13:2355-2379 (2012).
Mocco et al., Complement component C3 mediates inflammatory injury following focal cerebral ischemia, Circ. Res. 99:209-217 (2006).
Monsinjon et al., Regulation by complement C3a and C5a anaphylatoxins of cytokine production in human umbilical vein endothelial cells, FASEB J. 17:1003-1014 (2003).
Mufson et al., Hippocampal plasticity during the progression of Alzheimer's disease, Neuroscience. 309:51-67 (2015).
Munoz-Cernada et al., Factors involved in the design of nasal delivery systems for peptides and proteins, Biotecnologia Aplicada. 30(2):88-96 (2013).
Murphy et al., Plasticity during stroke recovery: from synapse to behaviour, Nature reviews, Neuroscience. 10:861-872 (2009).
Mwaniki et al., Long-term neurodevelopmental outcomes after intrauterine and neonatal insults: a systematic review, Lancet. 379:445-452 (2012).
Nakagawa et al., Bilateral movement training promotes axonal remodeling of the corticospinal tract and recovery of motor function following traumatic brain injury in mice, Cell Death & Disease. 4:e534 (2013).
Nowicka et al., Spatiotemporal dynamics of astroglial and microglial responses after photothrombotic stroke in the rat brain, Acta. Neurobiol. Exp. 68:155-168 (2008).
Orsini et al. Versatility of the complement system in neuroinflammation, neurodegeneration and brain homeostasis, Front Cell Neurosci. 8:380 (2014).
Pekna et al., Modulation of neural plasticity as a basis for stroke rehabilitation, Stroke. 43:2819-2828 (2012).
Pekny et al., The dual role of astrocyte activation and reactive gliosis, Neuroscience Letters. 565:30-38 (2014).
Pereira et al., Early enriched housing results in partial recovery of memory deficits in female, but not in male, rats after neonatal hypoxia-ischemia, Brain Res. 1218:257-266 (2008).

(56) References Cited

OTHER PUBLICATIONS

Perez-Alcazar et al., Altered cognitive performance and synaptic function in the hippocampus of mice lacking C3, Exp. Neurol. 253:154-164 (2014).
Porritt et al., Photothrombosis-induced infarction of the mouse cerebral cortex is not affected by the Nrf2-activator sulforaphane, PLoS One. 7:e41090 (2012).
Qiu et al., Less neurogenesis and inflammation in the immature than in the juvenile brain after cerebral hypoxia-ischemia, J. Cereb. Blood Flow Metab. 27:785-794 (2007).
Rahpeymai et al., Complement: a novel factor in basal and ischemia-induced neurogenesis, EMBO J. 25:1364-1374(2006).
Reid et al., Downsizing a human inflammatory protein to a small molecule with equal potency and functionality, Nat. Communic. 4:2802 (2013).
Reid et al., Potent heterocyclic ligands for human complement c3a receptor, J. Med. Chem. 57(20):8459-8470 (2014).
Rice et al., The influence of immaturity on hypoxic-ischemic brain damage in the rat, Ann. Neurol. 9:131-141 (1981).
Rocha Ferreira et al., Antimicrobial peptides and complement in neonatal hypoxia-ischemia induced brain damage, Front Immunol. 6:56 (2015).
Rojas et al., Effects of daily environmental enrichment on behavior and dendritic spine density in hippocampus following neonatal hypoxia-ischemia in the rat, Exp. Neurol. 241:25-33 (2013).
Rynkowski et al., C3a receptor antagonist attenuates brain injury after intracerebral hemorrhage, J. Cereb. Blood Flow Metab. 29:98-107 (2009).
Scafidi et al., Intranasal epidermal growth factor treatment rescues neonatal brain injury, Nature. 506:230-234 (2014).
Schafer et al., Microglia sculpt postnatal neural circuits in an activity and complement-dependent manner, Neuron. 74:691-705 (2012).
Schallert et al., CNS plasticity and assessment of forelimb sensorimotor outcome in unilateral rat models of stroke, cortical ablation, parkinsonism and spinal cord injury, Neuropharmacology. 39:777-787 (2000).
Scheff et al., Hippocampal synaptic loss in early Alzheimer's disease and mild cognitive impairment, Neurobiology of Aging. 27:1372-1384 (2006).
Schraufstatter et al., Complement activation in the context of stem cells and tissue repair, World J. Stem. Cells. 7(8):1090-1108 (2015).
Schraufstatter et al., Complement C3a and C5a Induce different signal transduction cascades in endothelial cells, J. Immunol. 169: 2102-2110 (2002).
Schroeter et al., Local immune responses in the rat cerebral cortex after middle cerebral artery occlusion, J. Neuroimmunol. 55:195-203 (1994).
Scully et al., Selective hexapeptide agonists and antagonists for human complement C3a receptor, J. Med.Chem. 53:4938-4948 (2010).
Sheldon et al., Strain-related brain injury in neonatal mice subjected to hypoxia-ischemia, Brain Res. 810:114-122 (1998).
Shinjyo et al., Complement Peptide C3a Promotes Astrocyte Survival in Response to Ischemic Stress, Mol. Neurobiol. 53:3076-3087 (2016).
Shinjyo et al., Complement-derived anaphylatoxin C3a regulates in vitro differentiation and migration of neural progenitor cells, Stem Cells. 27:2824-2832 (2009).
Shiromoto et al., The Role of Endogenous Neurogenesis in Functional Recovery and Motor Map Reorganization Induced by Rehabilitative Therapy after Stroke in Rats, Journal of Stroke and Cerebrovascular Diseases. 26:260-272 (2017).
Singh et al., Potent complement C3a receptor agonists derived from oxazole amino acids: Structure-activity relationships, Bioorg. Med. Chem. Lett. 25(23):5604-5608 (2015).
Stevens et al., The classical complement cascade mediates CNS synapse elimination, Cell. 131:1164-1178 (2007).
Stokowska et al., Complement peptide C3a stimulates neural plasticity after experimental brain ischaemia, Brain. 140(2): 353-369 (2017).
Sun et al., Inhibition of injury-induced cell proliferation in the dentate gyrus of the hippocampus impairs spontaneous cognitive recovery after traumatic brain injury, Journal of Neurotrauma. 32:495-505 (2015).
Svedin et al., Matrix metalloproteinase-9 gene knock-out protects the immature brain after cerebral hypoxia-ischemia, J. Neurosci. 27:1511-1518, (2007).
Takatsuru et al., Neuronal circuit remodeling in the contralateral cortical hemisphere during functional recovery from cerebral infarction, J. Neurosci. 29:10081-10086 (2009).
Tamakoshi et al., Motor skills training promotes motor functional recovery and induces synaptogenesis in the motor cortex and striatum after intracerebral hemorrhage in rats, Behavioural Brain Research. 260:34-43 (2014).
Ten et al., Complement component C1q mediates mitochondria-driven oxidative stress in neonatal hypoxic-ischemic brain injury, J. Neurosci. 30:2077-2087 (2010).
Teo et al., Hypoxic postconditioning reduces microglial activation, astrocyte and caspase activity, and inflammatory markers after hypoxia-ischemia in the neonatal rat brain, Pediatr. Res. 77:757-764 (2015).
Toni et al., LTP promotes formation of multiple spine synapses between a single axon terminal and a dendrite, Nature. 402:421-425 (1999).
Van Beek et al., Expression of receptors for complement anaphylatoxins C3a and C5a following permanent focal cerebral ischemia in the mouse, Exp. Neurol. 161: 373-382 (2000).
Vasek et al., A complement-microglial axis drives synapse loss during virus-induced memory impairment, Nature. 534:538-543 (2016).
Vavrek et al., BDNF promotes connections of corticospinal neurons onto spared descending interneurons in spinal cord injured rats, Brain. 129:1534-1545 (2006).
Waddell et al., Sex differences in cell genesis, hippocampal volume and behavioral outcomes in a rat model of neonatal HI, Exp. Neurol. 275:285-295 (2016).
Walker et al., Stress as necessary component of realistic recovery in animal models of experimental stroke, J. Cereb. Blood Flow Metab. 34:208-214 (2014).
Wang, Translational Animal Models in Drug Discovery and Development (2012).
Warraich et al., Neural plasticity: the biological substrate for neurorehabilitation, PM & R: The American Academy of Physical Medicine and Rehabilitation. Suppl. 2:S208-S219 (2010).
Watson et al., Induction of reproducible brain infarction by photochemically initiated thrombosis, Ann. Neurol. 17:497-504 (1985).
Wattananit et al., Monocyte-Derived Macrophages Contribute to Spontaneous Long-Term Functional Recovery after Stroke in Mice, J. Neurosci. 36: 4182-4195(2016).
Wieloch et al., Mechanisms of neural plasticity following brain injury, Curr. Opin. Neurobiol. 16:258-264 (2006).
Winship et al., Remapping the somatosensory cortex after stroke: insight from imaging the synapse to network, Neuroscientist. 15:507-524 (2009).
Wu et al., Complement component C3a plays a critical role in endothelial activation and leukocyte recruitment into the brain, J. Neuroinflammation. 13:23 (2016).
Wu et al., The receptor for complement component C3a mediates protection from intestinal ischemia-reperfusion injuries by inhibiting neutrophil mobilization, Proc. Natl. Acad. Sci. USA. 110:9439-9444 (2013).
Yang et al., Neuroprotective effects of the SCR1-3 functional domain of CR1 on acute cerebral ischemia and reperfusion injury in rats, Neurol. Res. 35:976-983 (2013).
Zang et al., Loss of synaptophysin-positive boutons on lumbar motor neurons innervating the medial gastrocnemius muscle of the SOD1G93A G1H transgenic mouse model of ALS, Journal of Neuroscience Research. 79:694-699 (2005).

(56) References Cited

OTHER PUBLICATIONS

Alawieh et al., Modulation of post-stroke degenerative and regenerative processes and subacute protection by site-targeted inhibition of the alternative pathway of complement, Journal of Neuroinflammation. 12:247 (2015).
Arumugam et al., Neuroprotection in stroke by complement inhibition and immunoglobulin therapy, Neuroscience. 158:1074-1089 (2009).
Arvidsson et al., Neuronal replacement from endogenous precursors in the adult brain after stroke, Nat. Med. 8:963-970 (2002).
Bahadur et al., Physicochemical and physiological considerations for efficient nose-to-brain targeting, Expert Opinion on Drug Delivery. 9:19-31 (2012).
Baskin et al., Two effective behavioral tasks for evaluating sensorimotor dysfunction following traumatic brain injury in mice, Journal of Neuroscience Methods. 129:87-93 (2003).
Becerril-Ortega et al., Iron overload accelerates neuronal amyloid-beta production and cognitive impairment in transgenic mice model of Alzheimer's disease, Neurobiology of Aging. 35:2288-2301 (2014).
Bellows-Peterson et al., De novo peptide design with C3a receptor agonist and antagonist activities: theoretical predictions and experimental validation, J. Med. Chem. 55(9):4159-4168 (2012).
Bellucci et al., Review: Parkinson's disease: from synaptic loss to connectome dysfunction, Neuropathology and Applied Neurobiology. 42:77-94 (2016).
Benowitz et al., GAP-43: an intrinsic determinant of neuronal development and plasticity, Trends Neurosci. 20:84-91 (1997).
Benowitz et al., The pattern of GAP-43 immunostaining changes in the rat hippocampal formation during reactive synaptogenesis, Molecular Brain Research. 8:17-23 (1990).
Boire et al., Complement Component 3 Adapts the Cerebrospinal Fluid for Leptomeningeal Metastasis, Cell. 168:1101-1113 (2017).
Bokisch et al., Anaphylatoxin inactivator of human plasma: its isolation and characterization as a carboxypeptidase, J. Clin. Invest. 49:2427-2436 (1970).
Boos et al., Deletion of the complement anaphylatoxin C3a receptor attenuates, whereas ectopic expression of C3a in the brain exacerbates, experimental autoimmune encephalomyelitis, J. Immunol. 173:4708-4714 (2004).
Brennan et al., Complement receptor C3aR1 controls neutrophil mobilization following spinal cord injury through physiological antagonism of CXCR2, JCI. Insight. 4 (2019).
Burda et al., Astrocyte roles in traumatic brain injury, Experimental Neurology. 275:305-315 (2016).
Calautti et al., Functional neuroimaging studies of motor recovery after stroke in adults: a review, Stroke. 34:1553-1566 (2003).
Carmichael et al., Growth-associated gene expression after stroke: evidence for a growth-promoting region in peri-infarct cortex, Exp. Neurol. 193:291-311 (2005).
Carmichael et al., New patterns of intracortical projections after focal cortical stroke, Neurobiol. Dis. 8:910-922 (2001).
Carmichael et al., Synchronous neuronal activity is a signal for axonal sprouting after cortical lesions in the adult, The Journal of Neuroscience. 22:6062-6070 (2002).
Chapman et al., Intranasal Treatment of Central Nervous System Dysfunction in Humans, Pharm. Res. 30:2475-2484 (2013).
Chauhan et al., Brain uptake of neurotherapeutics after intranasal versus intraperitoneal delivery in mice, J. Neurol. Neurosurg. 2(1):pii: 009 (2015).
Chavez-Valdez et al., Necrostatin-1 attenuates mitochondrial dysfunction in neurons and astrocytes following neonatal hypoxia-ischemia, Neuroscience. 219:192-203 (2012).
Chen et al., Activating mitochondrial regulator PGC-1alpha expression by astrocytic NGF is a therapeutic strategy for Huntington's disease, Neuropharmacology. 63:719-732 (2012).
Chen et al., Niaspan increases angiogenesis and improves functional recovery after stroke, Ann. Neurol. 62:49-58 (2007).
Chonkar et al., Smart Polymers in Nasal Drug Delivery, Indian J. Pharm. Sci. 77(4): 367-375, (2015).
Cikla et al., Suppression of microglia activation after hypoxia-ischemia results in age-dependent improvements in neurologic injury, Journal of Neuroimmunology. 291:18-27 (2016).
Costa et al., Role of complement component C5 in cerebral ischemia/reperfusion injury, Brain Res. 1100:142-51 (2006).
Crider et al., Complement component 3a receptor deficiency attenuates chronic stress-induced monocyte infiltration and depressive-like behavior, Brain Behav Immun. 70: 246-256 (2018).
Cui et al., Niacin treatment of stroke increases synaptic plasticity and axon growth in rats, Stroke. 41:2044-2049 (2010).
Cui et al., The neurorestorative benefit of GW3965 treatment of stroke in mice, Stroke. 44:153-161 (2013).
Davoust et al., Receptor for the C3a anaphylatoxin is expressed by neurons and glial cells, Glia. 26:201-211 (1999).
Dawbarn et al., Neurotrophins and neurodegeneration, Neuropathology and Applied Neurobiology. 29:211-230 ((2003).
De Rosa et al., Intranasal administration of nerve growth factor (NGF) rescues recognition memory deficits in AD11 anti-NGF transgenic mice, Proc. Natl. Acad. Sci. 102:3811-3816 (2005).
De Simoni et al., Neuroprotection by complement (C1) inhibitor in mouse transient brain ischemia, Journal of Cerebral Blood Flow & Metabolism. 23:232-239 (2003).
Dekker et al., Noradrenaline release from streptolysin O-permeated rat cortical synaptosomes: effects of calcium, phorbol esters, protein kinase inhibitors, and antibodies to the neuron-specific protein kinase C substrate B-50 (GAP-43), Journal of Neurochemistry. 56:1146-1153 (1991).
Denonne et al., Discovery of new C3aR ligands. Part 2: amino-piperidine derivatives, Bioorganic & Medicinal Chemistry Letters. 17:3262-3265 (2007).
Dijkhuizen et al., Functional magnetic resonance imaging of reorganization in rat brain after stroke, Proc. Natl. Acad. Sci. 98:12766-12771 (2001).
Dillard et al., Complement C3a regulates Muc5ac expression by airway clara cells independently of Th2 responses, Am. J. Respir. Crit. Care. Med. 175:1250-1258 (2007).
Ducruet et al., C3a receptor modulation of granulocyte infiltration after murine focal cerebral ischemia is reperfusion dependent, J. Cereb. Blood Flow Metab. 28:1048-1058 (2008).
Ducruet et al., Complement inhibition promotes endogenous neurogenesis and sustained anti-inflammatory neuroprotection following reperfused stroke, PLoS One. 7:e38664 (2012).
Edwards et al., Neurological outcomes at 18 months of age after moderate hypothermia for perinatal hypoxic ischaemic encephalopathy: synthesis and meta-analysis of trial data, BMJ (Clinical research ed.). 340:c363 (2010).
Fang et al., The immune complex CTA1-DD/IgG adjuvant specifically targets connective tissue mast cells through FcgammaRIIIA and augments anti-HPV immunity after nasal immunization, Nature Publishing Group. 6:1168-1178 (2013).
Feigin et al., Global and regional burden of stroke during 1990-2010: findings from the Global Burden of Disease Study 2010, Lancet. 383:245-254 (2014).
Filli et al., Structural and functional reorganization of propriospinal connections promotes functional recovery after spinal cord injury, Neural Regeneration Research. 10:509-513 (2015).
Finkelman et al., Human IgE-independent systemic anaphylaxis, The Journal of Allergy and Clinical Immunology. 137:1674-1680 (2016).
Ganeshina et al., Synapses with a segmented, completely partitioned postsynaptic density express more AMPA receptors than other axospinous synaptic junctions, Neuroscience. 125:615-623 (2004).
Goldshmit et al., Treadmill training after spinal cord hemisection in mice promotes axonal sprouting and synapse formation and improves motor recovery, Journal of Neurotrauma. 25:449-465 (2008).
Gong et al., Mild hypothermia inhibits systemic and cerebral complement activation in a swine model of cardiac arrest, J. Cereb. Blood Flow Metab. 35:1289-1295 (2015).
Gu et al., Cortical neurogenesis in adult rats after reversible photothrombotic stroke, J. Cereb. Blood Flow Metab. 20:1166-1173 (2000).

(56) References Cited

OTHER PUBLICATIONS

Hagberg et al. Perinatal brain damage: The term infant, Neurobiol. Dis. 92:102-112 (2016).
Bivard et al., Transient Ischemic Attack Results in Delayed Brain Atrophy and Cognitive Decline, Stroke, 49(2):384-90 (2018).
Cai et al., Functional Dynamics of Neutrophils After Ischemic Stroke, Translational Stroke Research, 11:108-121 (2020).
Emsley et al., A randomised phase II study of interleukin-1 receptor antagonist in acute stroke patients, J. Neurol. Neuro., Psych., 76:1366-1372 (2005).
European Patent Application No. 17809224.3, Office Action, dated Feb. 9, 2021.
Jickling et al., Targeting neutrophils in ischemic stroke: translational insights from experimental studies, J. Cereb. Blood. Flow Met., 35:888-901 (2015).
Koch et al., Drug delivery via the nose, Innovations in Pharmaceutical Technology, 90-94 (Jun. 2002).
Kuchcinski et al., Thalamic alterations remote to infarct appear as focal iron accumulation and impact clinical outcome, Brain, 140(7):1932-46 (2017).
Lindsberg et al., Coronary Heart Disease/Atherosclerosis/Myocardial Infarction: Endothelial ICAM-1 Expression Associated With Inflammatory Cell Response in Human Ischemic Stroke, Ovid: Cor. Heart Dis./Atheros./Myoc. Inf., 94(5):939-945 (1996).

* cited by examiner

C3A RECEPTOR AGONISTS FOR USE AGAINST ISCHEMIC BRAIN INJURY, STROKE, TRAUMATIC BRAIN INJURY, SPINAL CORD INJURY AND NEURODEGENERATIVE DISORDERS

CROSS-REFERENCE TO RELATED APPLICATIONS

This application is the U.S. national phase of International Patent Application No. PCT/EP2017/079811, filed 20 Nov. 2017, which claims priority benefit of Great Britain Patent Application No. 1619637.0, filed 21 Nov. 2016.

Incorporation-by-Reference of Sequence Listing Materials Submitted Electronically This application contains, as a separate part of the disclosure, a Sequence Listing in computer readable form (Filename: 52374_Seqlisting.txt; Size: 18,614 bytes; Created: May 17, 2019), which is incorporated by reference in its entirety.

The present invention provides C3a receptor agonists for use in the prevention and treatment of ischemic and other types of brain injury as well as compositions, devices for intranasal administration and kits comprising a C3a receptor agonist.

BACKGROUND

Stroke is the primary cause of disability in adults and the second most common cause of death (Feigin et al., 2014). Loss of function after stroke is due to cell death in the infarcted tissue and cell dysfunction in surrounding and remote brain areas that are connected to the damaged area (Wieloch and Nikolich, 2006). Ischemic brain damage induces endogenous repair processes that include proliferation and differentiation of neural stem cells, resulting in partial replacement of lost neurons (Arvidsson et al., 2002; Gu et al., 2000) and extensive rewiring of the remaining neuronal connections (Carmichael et al., 2001). The latter process involves sprouting of axonal projections and establishment of new synaptic contacts that result in cortical map rearrangement (Winship and Murphy, 2009). Understanding the mechanisms controlling these ischemia-induced neural plasticity processes and their modulation is paramount to identification of novel treatment strategies to promote functional recovery.

The complement system is a part of innate immunity that provides an effective first line of defense against invading microorganisms by contributing to opsonization and cytolysis, promoting phagocytosis of foreign particles and leukocyte recruitment. The inventors have previously shown that C3aR signalling stimulates neurogenesis in unchallenged adult mice (Rahpeymai et al., 2006) and C3a regulates neural progenitor cell migration and differentiation in vitro (Shinjyo et al., 2009). Complement activation-mediated neutrophil infiltration is detrimental in several types of ischemic injury. Consistent with this view, complement inhibition proved neuroprotective in cerebral ischemia with reperfusion (Arumugam et al., 2009; Costa et al., 2006; De Simoni et al., 2003; Gong et al., 2015; Huang et al., 1999; Mocco et al., 2006; Yang et al., 2013). Treatment with a C3aR antagonist improved functional and morphological outcome following ischemia-reperfusion in adult mice (Ducruet et al., 2012). Blocking the binding of C3a to C3aR modulated tissue injury after stroke and established antagonism of C3aR as a promising strategy for ameliorating injury after ischemia/reperfusion (Ducruet et al., 2008). C3aR activation led to increased vascular permeability, smooth muscle contraction, activation of myeloid cells such as neutrophils, monocytes/macrophages, basophils, and platelets, as well as directed migration of inflammatory cells (Klos et al., 2009). C3aR plays a critical role in endothelial activation and leukocyte recruitment into the brain (Wu et al., 2016). Treatment with C3aR antagonist improved neurologic outcome after experimental intracerebral hemorrhage. The authors proposed that the inhibition of C3aR may be a promising target for therapeutic intervention in hemorrhagic stroke (Rynkowski et al., 2009). However, the precise role of C3a in the ischemic brain is unclear. In a permanent cerebral ischemia model, deletion of the C3 gene was associated with the development of larger infarcts and reduced post-stroke neurogenesis (Rahpeymai et al., 2006). In an in vitro ischemia model, C3a increased the survival of astrocytes (Shinjyo et al., 2015). Overexpression of C3a in reactive astrocytes in the immature brain was shown to be neuroprotective, and intraventricular treatment with C3a ameliorated memory impairment resulting from neonatal hypoxia-ischemia in wild type control ($C3aR^{+/+}$) mice but not C3aR-deficient ($C3aR^{-/-}$) mice (Järlestedt et al., 2013). In addition, C3 expression was upregulated in sprouting neurons isolated from rat cortex after ischemic stroke (Li et al., 2010). As some growth factors have been shown to promote axonal regeneration and sprouting after spinal cord injury (Lu et al., 2004; Vavrek et al., 2006), the finding that C3a induces upregulation of neural growth factor (NGF) in microglia and astrocytes in vitro (Heese et al., 1998; Jauneau et al., 2006) implies that complement can also exert pro-regenerative functions indirectly. Taken together, these findings teach that C3a has multiple and opposing roles in the injured nervous system but also raise the possibility that the complement proteins, and C3aR signalling in particular, are involved in ischemia-induced neural plasticity including cell replacement, reorganization of axonal circuitry, and consequently, regulation of synaptic input. However, the role of the complement system in ischemic brain injury is complex and seems to depend not only on factors such as the type of ischemic injury and the developmental stage of the brain but also on length of time after injury.

Ischemic stroke induces endogenous repair processes that include proliferation and differentiation of neural stem cells and extensive rewiring of the remaining neural connections, yet about 50% of stroke survivors live with severe long-term disability. There is an unmet need for drug therapies to improve recovery by promoting brain plasticity in the sub-acute to chronic phase after ischemic stroke.

Neonatal hypoxic-ischemic encephalopathy (HIE) due to perinatal asphyxia is the leading cause of neurological injury resulting from birth complications. It is caused by the disruption of blood flow and oxygen delivery to the brain prior to or during delivery and occurs in 1-3 of 1000 live term births (Kurinczuk et al., 2010). Recent advances in critical care have improved the survival of infants suffering from HIE, but approximately 50% of survivors will develop complications such as intellectual disability and cerebral palsy (Mwaniki et al., 2012). Therapeutic hypothermia of children with HIE is a clinically accepted therapy that reduces by 12% the number of children with disabilities at 2 years of age (Edwards et al., 2010).

Inflammation is a critical contributor to both normal development and injury outcome in the immature brain;

depending on the timing and context, inflammation can prime the brain for injury or be neuroprotective (Hagberg et al., 2015).

The immature and adult brains show dramatic differences in the role of the complement proteins in ischemic injury such as e.g neonatal but not adult mice deficient in C1q, the initial component of the classical pathway of complement activation, were protected against hypoxic-ischemic injury (Ten et al., 2010). Thus the effects of an intervention to treat ischemic brain injury in neonates cannot be directly extrapolated to the treatment of ischemic brain injury in adults and vice versa.

There is a need for new materials for and methods of treating ischemic brain injuries that occur at different stages in life, including new materials and methods which involves a clinically feasible administration route.

BRIEF SUMMARY OF THE DISCLOSURE

The present invention has surprisingly found that intranasal administration of C3a receptor agonists (such as C3a) can be used to treat ischemic brain injury. Suitably, such administration may advantageously result in one or more of the following: a reduction in cognitive impairment and/or tissue loss following ischemic stress; an increase in the density of pre-synaptic terminals in the peri-infarct cortex; stimulation of post-ischemic neural plasticity; reduction of activation and/or proliferation of astrocytes and/or microglia (jointly called reactive gliosis); and an improvement in functional recovery. Furthermore, such administration may reduce risk of serious adverse reactions, such as anaphylaxis, compared to other administration routes. Thus, the inventors have surprisingly identified that intranasal administration of C3a receptor agonists can be used to provide clinically feasible treatment of an ischemic brain injury.

Although best known for its role in the elimination of pathogenic bacteria, complement has also other functions such as the initiation of inflammation and the regulation of antibody production. Research during the past 10 years has shown that complement is a major regulator of brain plasticity and function in the healthy as well as diseased brain.

Intraventricular administration of drugs is not clinically feasible. The efficiencies of delivery to central nervous system for proteins is very low (<0.05%) (Lochhead and Thorne, 2012). Furthermore, systemic administration of C3a carries a risk of serious adverse reactions including anaphylaxis (Finkelman et al., 2016). In addition, the availability in the CNS of systemically administered C3a would be limited due its rapid inactivation by serum carboxypeptidases (Bokisch and Muller-Eberhard, 1970) as well as by the blood-brain barrier.

Accordingly, the present invention provides use a human C3a receptor agonist in the manufacture of a medicament for the treatment or prevention of one or more of: an ischemic brain injury, stroke, traumatic brain injury, spinal cord injury and neurodegenerative disorders, wherein the medicament is formulated for intranasal delivery. Suitably, the medicament may be for the treatment or prevention of an ischemic brain injury.

Suitably, the human C3a receptor agonist may comprise arginine or Leu-Gly-Leu-Ala-Arg (SEQ ID NO: 1, positions 73-77) (at the C-terminal. Suitably, the human C3a receptor agonist may comprise amino acids 65 to 77 of SEQ ID NO: 1 or amino acids 57 to 77 of SEQ ID NO: 1, preferably at the C-terminal. Suitably, the human C3a receptor agonist may be a human C3a as shown in SEQ ID NO: 1 or a C3a receptor agonist having at least 70% identity thereto.

The amino acid sequence of human C3a peptide (SEQ ID NO: 1).

```
SVQLTEKRMD KVGKYPKELR KCCEDGMREN PMRFSCQRRT
RFISLGEACK KVFLDCCNYI TELRRQHARA SHLGLAR
```

Suitably, the C3a receptor agonist may be selected from the group consisting of: a C3a peptide, Trp-Trp-Gly-Lys-Lys-Tyr-Arg-Ala-Ser-Lys-Leu-Gly-Leu-Ala-Arg (SEQ ID NO: 2) and derivatives thereof; Phe-Leu-Pro-Leu-Ala-Arg (SEQ ID NO: 3); Phe-Ile-Pro-Leu-Ala-Arg (SEQ ID NO: 6); Phe-Trp-Thr-Leu-Ala-Arg (SEQ ID NO: 7); Phe-Leu-Thr-Leu-Ala-Arg (SEQ ID NO: 8); Boc-Leu-oxazole-Arg; Boc-Ile-oxazole-Arg; Boc-Ile-5-methyl-oxazole-Arg; 3-indole-carboxylic acid-Leu-imidazole-Arg; 3-indole-carboxylic acid-Leu-oxazole-Arg; 5-bromonicotinic acid-Leu-oxazole-Arg; 4-(biphenyl-4-yl)-4-oxobutanoic acid-Ile-oxazole-Arg; isoquinoline-1-Ile-oxazole-Arg; (2-Benzhydryl-4-methyl-1H-imidazole-5-carbonyl)-L-Arg; (2-Benzhydryl-1H-imidazole-5-carbonyl)-L-Arg; (2-Benzhydryl-1,5-dimethyl-1H-imidazole-4-carbonyl)-L-Arg; and 2-cyclohexyl-2-phenyl-N-[1-(3-pyridin-3-ylpropanoyl)piperidin-4-yl] acetamide and their derivatives or compounds described in US patent publication no. 2008/0188528 A1, incorporated herein by reference in its entirety and specifically for the C3a receptor agonist compounds described therein.

Suitably, the medicament formulated for intranasal administration may be a composition comprising the C3a receptor agonist and a pharmaceutically acceptable carrier, such as a buffer (e.g. phosphate buffered saline). In one embodiment of the invention, the composition of the invention may comprise a galenical gel formulation of an agonist, wherein such formulation comprises of thickening and gelling agents such as for example of colloidal silicon dioxide, cellulose and cellulose derivatives, polysaccharides, polyvinyl alcohol and like. A pharmaceutical formulation may comprise a lypophylic transport/carrier moiety such as fatty acid, for example caprylic acid, lauric acid, oleic acid, linoleic acid, or arachidonic acid, or mixtures thereof. Mucoadhesive agents, e.g., sodium hyaluronate, chitosan, acrylic acid derivatives, lectin, and low methylated pectin, surface-engineered nanoparticles, efflux transporter inhibitors, and vasoconstrictors, may be used to reduce clearance, to prolong the residence time of the formulation at the delivery site, and to increase transport from the nasal epithelium to the brain.

Recommended dosages for intranasal administration are in the range of about 0.1 nanogram to about 500 milligrams per kilogram of body weight per day. Effective doses may be extrapolated from dose-response curves derived from in vitro or animal model test systems. Such animal models and systems are well known in the art. For example, human neural cells may be cultured with different doses of a C3a receptor agonist. Calcium ion mobilization from intracellular stores may be used as a measure of C3a receptor activation, cell death may be used as a measure of toxicity. In another example, rodents after experimental brain ischemia may be intranasally treated with different doses of a C3a receptor agonist and the degree and speed of recovery of motor function may be used as a as measure of therapeutic effect. An effective dose for clinical application may be calculated based on the weight ratio between said rodent and humans. The amount of an agent administered as a unit dose will further depend upon the type of pharmaceutical composition being administered, for example, a solution, a suspension, a gel, an emulsion, a powder, or a sustained-release formulation. For example, dosages used for administration of a C3a receptor agonist can include, but are not limited to, an effective amount within the dosage range of about 0.1 ng per kg body weight to about 500 mg per kg body weight, or within 1 ng per kg body weight to about 500 mg per kg body weight, or within about 10 ng per kg body weight to about 50 mg per kg body weight, or within about 0.1 µg per kg body weight to about 500 mg per kg body weight, or within about 1 µg per kg body weight to about 500 mg per kg body weight, within about 10 µg per kg body weight to about 500 mg per kg body weight.

Suitably, the ischemic brain injury may be ischemic stroke, neonatal hypoxic-ischemic encephalopathy, focal cerebral ischemia or global cerebral ischemia.

Suitably, the medicament may be formulated for daily intranasal administration. Suitably, the medicament may be administered for at least three days or at least a week or at least a month. Suitably, if the ischemic brain injury is the result of an ischemic stroke, the medicament is administered after the active (aka acute to subacute) phase of the stroke, such as 7 days after the ischemic stroke. Suitably, if the ischemic brain injury is the result of an ischemic stroke, the medicament may be administered daily for at least three weeks or at least two months if impairment of neurological functions, such as motor functions or cognitive functions, persists.

By the "acute phase" is meant the period of the first 24 hours after symptom onset. The "subacute phase" refers to the period of 24 hours to 5 days after symptom onset. Suitably, the duration of the active phase is determined by the treating physician. In some variations, duration of active phase is determined based on, e.g., the extent and duration of brain edema.

Throughout the description and claims of this specification, by "neonatal" is meant the period between birth and one month of age.

In another aspect, the present invention relates to a human C3a receptor agonist for use in the treatment or prevention of one or more of: an ischemic brain injury, stroke, traumatic brain injury, spinal cord injury and neurodegenerative disorders, wherein the human C3a receptor agonist is formulated for intranasal delivery. Suitably, the human C3a receptor agonist may be for use in the treatment or prevention of an ischemic brain injury.

Suitably, the C3a receptor agonist may comprise arginine or may comprise the sequence Leu-Gly-Leu-Ala-Arg (SEQ ID NO: 1, positions 73-77) at the C-terminal.

Suitably, the C3a receptor agonist may comprise amino acids 65 to 77 of SEQ ID NO: 1 or amino acids 57 to 77 of SEQ ID NO: 1.

Suitably, the C3a receptor agonist may be a human C3a as shown in SEQ ID NO: 1 or a C3a receptor agonist having at least 70% identity thereto.

Suitably, the C3a receptor agonist may be selected from the group consisting of: a C3a peptide, Trp-Trp-Gly-Lys-Lys-Tyr-Arg-Ala-Ser-Lys-Leu-Gly-Leu-Ala-Arg (SEQ ID NO: 2) and derivatives thereof; Phe-Leu-Pro-Leu-Ala-Arg (SEQ ID NO: 3); Phe-Ile-Pro-Leu-Ala-Arg (SEQ ID NO: 6); Phe-Trp-Thr-Leu-Ala-Arg (SEQ ID NO: 7); Phe-Leu-Thr-Leu-Ala-Arg (SEQ ID NO: 8); Boc-Leu-oxazole-Arg; Boc-Ile-oxazole-Arg; Boc-Ile-5-methyl-oxazole-Arg; 3-indole-carboxylic acid-Leu-imidazole-Arg; 3-indole-carboxylic acid-Leu-oxazole-Arg; 5-bromonicotinic acid-Leu-oxazole-Arg; 4-(biphenyl-4-yl)-4-oxobutanoic acid-Ile-oxazole-Arg; isoquinoline-1-Ile-oxazole-Arg; (2-Benzhydryl-4-methyl-1H-imidazole-5-carbonyl)-L-Arg; (2-Benzhydryl-1H-imidazole-5-carbonyl)-L-Arg; (2-Benzhydryl-1,5-dimethyl-1H-imidazole-4-carbonyl)-L-Arg; and 2-cyclohexyl-2-phenyl-N-[1-(3-pyridin-3-ylpropanoyl)piperidin-4-yl] acetamide and their derivatives or compounds described in US patent publication no. 2008/0188528 A1, incorporated herein by reference in its entirety and specifically for its description of C3a receptor agonist compounds and how to make them.

Suitably, the human C3a receptor agonist formulated for intranasal administration may be a composition comprising the C3a receptor agonist and a pharmaceutically acceptable carrier, such as a buffer (e.g. phosphate buffered saline), or a gel.

Suitably, the ischemic brain injury is ischemic stroke, neonatal hypoxic-ischemic encephalopathy, focal cerebral ischemia or global cerebral ischemia.

Suitably, the human C3a receptor agonist is formulated for daily intranasal administration. Suitably, the human C3a receptor agonist may be administered for at least three days or at least a week. Suitably, if the ischemic brain injury is the result of an ischemic stroke, the human C3a receptor agonist may be administered 7 days after the ischemic stroke.

In a further aspect, the present invention provides a method of treating or preventing one or more of: an ischemic brain injury, stroke, traumatic brain injury, spinal cord injury and neurodegenerative disorders, said method comprising administering intranasally a therapeutically effective amount of a human C3a receptor agonist to a subject in need thereof. Suitably, the method may be for treating or preventing an ischemic brain injury.

Suitably, the human C3a receptor agonist may comprise arginine at the C-terminal or the sequence Leu-Gly-Leu-Ala-Arg (SEQ ID NO: 1, positions 73-77) at the C-terminal.

Suitably, the human C3a receptor agonist may comprise amino acids 65 to 77 of SEQ ID NO: 1 or amino acids 57 to 77 of SEQ ID NO: 1.

Suitably, the human C3a receptor agonist may be human C3a as shown in SEQ ID NO: 1 or a C3a receptor agonist having at least 70% identity thereto.

Suitably, the human C3a receptor agonist may be selected from the group consisting of: a C3a peptide, Trp-Trp-Gly-Lys-Lys-Tyr-Arg-Ala-Ser-Lys-Leu-Gly-Leu-Ala-Arg (SEQ ID NO: 2) and derivatives thereof; Phe-Leu-Pro-Leu-Ala-Arg (SEQ ID NO: 3); Phe-Ile-Pro-Leu-Ala-Arg (SEQ ID NO: 6); Phe-Trp-Thr-Leu-Ala-Arg (SEQ ID NO: 7); Phe-Leu-Thr-Leu-Ala-Arg (SEQ ID NO: 8); Boc-Leu-oxazole-Arg; Boc-Ile-oxazole-Arg; Boc-Ile-5-methyl-oxazole-Arg; 3-indole-carboxylic acid-Leu-imidazole-Arg; 3-indole-carboxylic acid-Leu-oxazole-Arg; 5-bromonicotinic acid-Leu-oxazole-Arg; 4-(biphenyl-4-yl)-4-oxobutanoic acid-Ile-oxazole-Arg; isoquinoline-1-Ile-oxazole-Arg; (2-Benzhydryl-4-methyl-1H-imidazole-5-carbonyl)-L-Arg; (2-Benzhydryl-1H-imidazole-5-carbonyl)-L-Arg; (2-Benzhydryl-1,5-dimethyl-1H-imidazole-4-carbonyl)-L-Arg; and 2-cyclohexyl-2-phenyl-N-[1-(3-pyridin-3-ylpropanoyl)piperidin-4-yl]acetamide and their derivatives or compounds described in US patent publication no. 2008/0188528 A1, incorporated herein by reference in its entirety and specifically for its description of C3a receptor agonist compounds and how to make them.

Suitably, the human C3a receptor agonist may be in a composition. The composition may comprise the human C3a receptor agonist and a pharmaceutically acceptable carrier. Suitably, the carrier may be a buffer, such as e.g.

phosphate buffered saline, or a gel, such as e.g. colloidal silicon dioxide, cellulose and cellulose derivatives, polysaccharides, polyvinyl alcohol and like.

Suitably, the ischemic brain injury may be ischemic stroke, neonatal hypoxic-ischemic encephalopathy, focal cerebral ischemia or global cerebral ischemia.

Suitably, the human C3a receptor agonist may be administered daily. Suitably, the human C3a receptor agonist may be administered for at least 3 consecutive days or at least a week.

Suitably, if the ischemic brain injury is the result of an ischemic stroke, the administering step may occur at least 7 days after the ischemic stroke.

Suitably, if the ischemic brain injury is the result of neonatal hypoxic-ischemic encephalopathy, the administering step may occur at least 1 hour after birth.

In yet another aspect, the present invention relates to a device for intranasal administration of a human C3a receptor agonist, wherein the device comprises a composition comprising a human C3a receptor agonist and a pharmaceutically acceptable carrier. Suitably, the device may be an intranasal spray device comprising a bottle, pump and an actuator. Suitably, the device may be a unit dose device or a multiple dose device. The delivery device can include, but is not limited to, unit dose containers, pump sprays, airless and preservative-free sprays, nebulizers, dose inhalers and pressurized dose inhalers, droppers, squeeze bottles, a nasal tampon, or a nasal sponge .together with a suitable applicator. Type of device will depend on the formulation of the C3a receptor agonist and can deliver an aerosol, drops or gel depots. Suitably, the device should provide for delivery of a C3a receptor agonist high in the nasal cavity so as to reach the olfactory epithelium, thereby maximizing delivery to the brain and limiting the delivery to the respiratory region of nasal cavity or throat thus preventing deposition of a drug in the lungs or stomach. Different approaches to satisfy such delivery requirement are known in the art (Ilium, "Intranasal delivery to the central nervous system" (2015) in "Blood-Brain Barrier in Drug Discovery: Optimizing Brain Exposure of CNS Drugs and Minimizing Brain Side Effects for Peripheral Drugs", pp. 535-565, DOI: 10.1002/9781118788523. ch 25, incorporated herein by reference). Examples of potentially suitable devices for aerosol delivery are: Impel NeuroPharma's POD device as described in US patent publication no. 20170043109 A1; ViaNase CPD device (Kurve Technology) as described in U.S. Pat. No. 8,001,963 B2; or Bi-directional device (OptiNose) as described in U.S. Pat. No. 6,715,485 B1, all incorporated herein by reference in their entirety.

Suitably, the human C3a receptor agonist may comprise arginine or Leu-Gly-Leu-Ala-Arg (SEQ ID NO: 1, positions 73-77) (at the C-terminal. Suitably, the human C3a receptor agonist may comprise amino acids 65 to 77 of SEQ ID NO: 1 or amino acids 57 to 77 of SEQ ID NO: 1, preferably at the C-terminal. Suitably, the human C3a receptor agonist may be a human C3a as shown in SEQ ID NO: 1 or a C3a receptor agonist having at least 70% identity thereto.

Suitably, the C3a receptor agonist may be selected from the group consisting of: a C3a peptide; Trp-Trp-Gly-Lys-Lys-Tyr-Arg-Ala-Ser-Lys-Leu-Gly-Leu-Ala-Arg (SEQ ID NO: 2) and derivatives thereof; Phe-Leu-Pro-Leu-Ala-Arg (SEQ ID NO: 3); Phe-Ile-Pro-Leu-Ala-Arg (SEQ ID NO: 6); Phe-Trp-Thr-Leu-Ala-Arg (SEQ ID NO: 7); Phe-Leu-Thr-Leu-Ala-Arg (SEQ ID NO: 8); Boc-Leu-oxazole-Arg; Boc-Ile-oxazole-Arg; Boc-Ile-5-methyl-oxazole-Arg; 3-indole-carboxylic acid-Leu-imidazole-Arg; 3-indole-carboxylic acid-Leu-oxazole-Arg; 5-bromonicotinic acid-Leu-oxazole-Arg; 4-(biphenyl-4-yl)-4-oxobutanoic acid-Ile-oxazole-Arg; isoquinoline-1-Ile-oxazole-Arg; (2-Benzhydryl-4-methyl-1H-imidazole-5-carbonyl)-L-Arg; (2-Benzhydryl-1H-imidazole-5-carbonyl)-L-Arg; (2-Benzhydryl-1,5-dimethyl-1H-imidazole-4-carbonyl)-L-Arg; and 2-cyclohexyl-2-phenyl-N-[1-(3-pyridin-3-ylpropanoyl)piperidin-4-yl] acetamide and their derivatives or compounds as described in US patent publication no. 2008/0188528 A1, incorporated herein by reference in its entirety and specifically for its description of C3a receptor agonist compounds and how to make them.

Suitably, the carrier may be a buffer, such as, e.g. phosphate buffered saline, or a gel, such as e.g. colloidal silicon dioxide, cellulose and cellulose derivatives, polysaccharides, polyvinyl alcohol and like.

Suitably, the composition may be formulated for daily intranasal administration. Suitably, the composition may be formulated for administration over at least three days or at least a week.

Suitably, the composition may be formulated for or may be administered at any appropriate time period for the treatment or prevention of the particular disease or disorder.

In a further aspect, the present invention provides a kit comprising a device in accordance with the invention and instructions for use.

Advantageously, the methods, devices and kits of the invention may be utilised to aid recovery by promoting brain plasticity in the subacute to chronic phase after ischemic stroke and/or ameliorates HI-induced cognitive impairment after asphyxia.

Throughout the description and claims of this specification, the words "comprise" and "contain" and variations of them mean "including but not limited to", and they are not intended to (and do not) exclude other moieties, additives, components, integers or steps. Further, throughout the description and claims of this specification, wherever words "comprise" and "contain" it is intended to also include the options of "consisting essentially of" and "consisting".

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Aspects of the invention that have been described herein as methods also can be described as "uses," and all such uses are contemplated as aspects of the invention. Likewise, compositions described herein as having a "use" can alternatively be described as processes or methods of using, which are contemplated as aspects of the invention.

The invention includes, as an additional aspect, all embodiments of the invention narrower in scope in any way than the variations defined by specific paragraphs above or by original claims. For example, where certain aspects of the invention that are described as a genus or set, it should be understood that every member of a genus or set is, individually, an aspect of the invention. Likewise, every individual subset is intended as an aspect of the invention. By way of example, if an aspect of the invention is described as a members selected from the group consisting of 1, 2, 3, and 4, then subgroups (e.g., members selected from {1,2,3} or {1,2,4} or {2,3,4} or {1,2} or {1,3} or {1,4} or {2,3} or {2,4} or {3,4}) are contemplated and each individual species {1} or {2} or {3} or {4} is contemplated as an aspect or variation of the invention. Likewise, if an aspect of the invention is characterized as a range, or being practiced over a range, such as a temperature range, then integer subranges are contemplated as aspects or variations of the invention. Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

Although the Applicant invented the full scope of the invention described herein, the Applicant does not intend to claim subject matter described in the prior art work of others. Therefore, in the event that statutory prior art within the scope of a claim is brought to the attention of the Applicant by a Patent Office, tribunal, or other entity or individual, the Applicant reserves the right to exercise amendment rights under applicable patent laws to redefine the subject matter of such a claim to specifically exclude such statutory prior art or obvious or noninventive variations of statutory prior art from the scope of such a claim. Variations of the invention defined by such amended claims also are intended as aspects of the invention.

Various aspects of the invention are described in further detail below. The headings herein are for the convenience of the reader and not intended to be limiting. Additional aspects, embodiments, and variations of the invention will be apparent from the Detailed Description and/or Drawing and/or claims. The original claims appended hereto are hereby incorporated by reference as part of the summary of the invention.

BRIEF DESCRIPTION OF THE DRAWINGS

Embodiments of the invention are further described hereinafter with reference to the accompanying drawings, in which.

DETAILED DESCRIPTION

Figure 1:
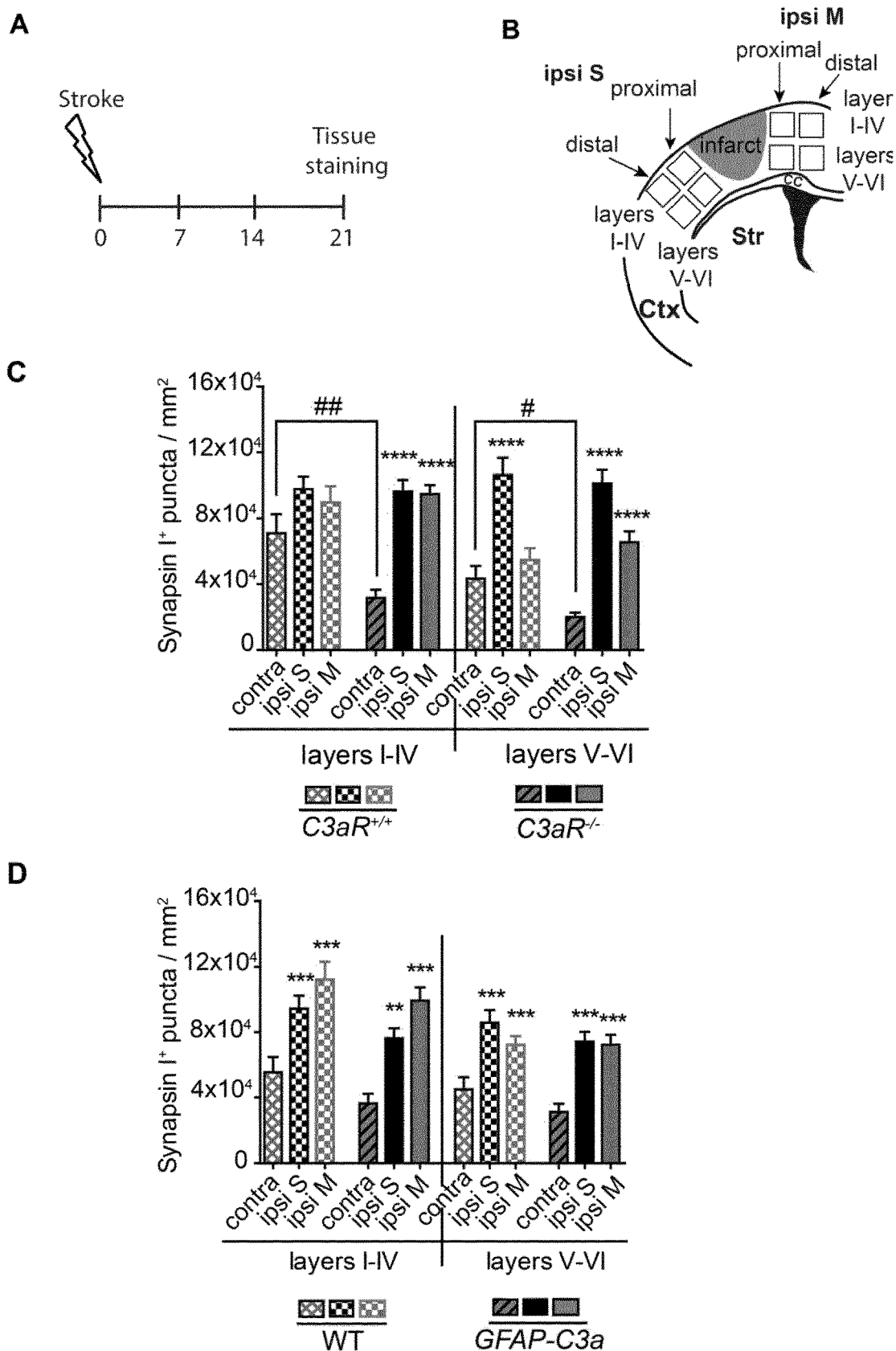
FIG. 1 shows that signalling through C3aR stimulates an increase in synaptic density in the contralesional cortex. (A) Study design. (B, C) Density of synapsin I+ puncta in the proximal peri-infarct and contralesional cortex (mean±SEM; C3aR$^{+/+}$ n=10, C3aR$^{-/-}$ n=14, WT n=13, GFAP-C3a n=12). (C) Schematic diagram indicating cortical regions chosen for analysis. One-way ANOVA with Sidak's planned comparisons: P<0.01, *P<0.001, ****P<0.0001 for ipsi vs. contra comparisons; #P<0.05, ##P<0.01 for between-genotype comparisons. contra—contralesional cortex; ipsi M—ipsilesional motor cortex; ipsi S—ipsilesional somatosensory cortex

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated. Typically, a physician will determine the actual dosage of the C3a receptor agonist, or composition comprising the same, which will be most suitable for an individual subject and it will vary with the age, weight and response of the particular subject. Preferably, the actual dosage that is used results in minimal toxicity to the subject. Preferably, the subject to be treated is a human.

The terms "peptide", "protein" and "polypeptide" are used interchangeably herein.

The term "C3a receptor" as used herein is synonymous with the complement component 3a receptor 1 (C3AR1) and relates to a specific G protein-coupled receptor (GPCR) involved in the complement system. Human C3a receptor is located on chromosome 12p13.31. The polynucleotide sequence of human C3a receptor 1 is set forth in SEQ ID NO: 4. The amino acid sequence is set forth in SEQ ID NO: 5.

The polynucleotide sequence of human C3a receptor 1 (SEQ ID NO: 4).

```
ctgtgaggtc agatagtggt ctagagcata agacttaact tattgccgga aacagagaga
gaacagaaga agagaaagct cagcaaattt tcttgccata cttcatgact tcactgtggc
taagtgtggg gaccagacag gactcgtgga gacatccagg tgctgaagcc ttcagctact
gtctcagttt tttggtaaga aaacctagac ctacctgatg acttgtgctt agcctgtttt
gctcattata ggtaatgagt ttgagtgtca ctatcttcta tttcccctat tccttctctg
actttgaatt cttttatctt atctctatgt ctaacttcct ttttctaaat attccacatt
gcatttgtct ttgcttttaa tattttcata gtggaattaa tagtgaattt ttacatcatt
tctttccttt ctttgaattg gctatgtatt tcaccctgaa ctttgattcc agctgtcccc
attaatttgt ttttcaaata attgattgca cttttttttcc ctttccattt cctctttctt
tttttattc ttttgcccat tccttattgc tactgactct gttatcctat tactacaatt
tgattctggg gtccactttt ctttctctat cacagtggaa ttttagtttc aggatattaa
ttacctttaa attacggctg gtcaacttag taataatttt ttttaatcct ctactaatct
taaacacata aaggtatggt attttttagcc aaattaactt gaagaaatgt aaaaagtaat
cttgctctgc aggactttt tttttttttt ttttttttga gacagagtct cactctgttg
cccaggctgg agtacagtag catgatctca gctcactgca acctccgcct cccaggttca
agcgattctc ctgcctcagc ctcctgagta ggtgggattg caggcacgtg ctaccacacc
cagttaaatt tttttgtatt tttagtagag acagggttcc accatgttgg ccaggttggt
ctcaaactcc tgacctcagg tgatctaccc gcctctgcct cccaaagtgc tgggattaca
ggcgtgagcc accacaccca gccttgttct aaaggacttt taatccctga ctcctacata
ctttcatttc aaaacagata ataacaatat ttaacatata gctcatgaca gataactcta
tttttattaa aattttgctg tttgcagtcc ctgctacttc agttcatgca gttctcggca
gcttcccctt tattagcaat accatatatc tttttttttt taatgtgatt tttttttttt
tttggtagta aaaacagcat ttgcctaaca gtcctcggac ctgaaatcca agaacctccc
tagtaatgat tatatgcttg taatctaatt tgctgagttt cactgtcaaa cttgagaaat
aaaagcagag aaaacgtagg ctgggcacag tggctcatgt ctgtaacccc agcacactgt
```

-continued

```
gaggccaaca tgggaggatt gcttgagtcc aggagtttga gagcagcttg ggcaacatag caagaccta  tctctacaaa caaacaaaca aacaaacaac aacaacaaca acaaaatgag gagaggagag atgattacca agttttcttt cagccctagc atcccatgac tctattcttc tctcaatatt ttaggggggt accgtgatag tatttaaata tctgagtaga caaggccatg gaaaggggaa tgagaataat ttcttcttct tttttttttt ttgagatgga gttttgcttt tgttgcccag gctggagtgt agtggcgcaa cctcggctca ccacaacctc tgcctcccag gttcaagcga ttctcctgcc tcagcctcct gagtagctgg gattacaggc atgtgccacc atgcccacct aattttgtat ttttagtaga cacagagttt ctccatgttg ataggctgg tctcaaactg acctcaggtg atctgcctgc cttggcttcc caaagtgctg ggataacagg tgtgagccac tgtgcccagc ccatgtcttc tttttatta ttttgttgac ttgctatttt aacttctgct aatcatatga ggccctatgg caatatttgg ctgactcagc agaactactt tcaagtcaca aaaatattt gagcctctat aaaagtaaaa tgttatttta tccagtaaaa attaggaatt tcacaaaaag aaagttaaaa gggacagcat gggaattaag gaagaggcct gggtaaggat tacatggata caaattagaa ttttagatgt aattgcaaaa gaaaaaaaaa gtcaaccccc aaaatgggca tccatctatt caagtaattt ttttttttctt ttttttttctt ttgagacaga gtctctttgt catgcaggct ggagtgcagt ggtgcaatct cagctcactg caacctccac ctctccagtt caagcgattc tcgtgcctca gcctcccaag tagctgggat tacaagtgtg agctaccaca cccagctaat tttgtattt ttggtagaga tgggattttg ccatgttagc caggctggtc ttgaactcct agccccaagc gatcttctcc cctcggcccc ccaaagtgct gcgattacag gcatgagcca ctgcgcccag cctttccaca taatctttaa ccttggtgtc tcataaggca ttatgttaaa ttatgtgaaa tgagcattta tgaataagac tccttttac catcataaag tttaaatcca gaataataga ttagacagcc attataatta ttgtacaaga taaaatgtgt cattgcatat agaatatgaa aaaaaggttc aaacatgcgc acacacacaa attaagaagc tgaagacttg gtgaagggca taattccaga tagaagtaaa cagcattagc catggaacgg aaaatggcat taagttggaa tagtgaattg ttcaggaaag ctataaagca gggtacattt acgagcatgt tcacagttag gggaaggtaa tatcacagag gccaagagaa gagagtgtta agaagtcagt gtatctaatg acacatattg tggaaggtga ctgagaaaca aacgtttgga tttggttttt agaagtaatt ttagcagaat tatggaagca gaagatacat tacaaagaat taagaagttg gtggccggcc gggcctggtg gctcacatct gtaatcccgg gactttggga ggccgaggcg ggcggatcac caggtcagga aatcaagatc atcctggcta acatggtgaa accccgtctc tactaaaaat acaaaaatta gccgggcgtg gtggtacacg cctgtaatcc cagctcctcg ggaggctgag gcagaagaat tgcttaaacc cgggatgcgg aggctgtagt gagccgagat cgcaccattg cactccagcc tgggagacag agcgagactc catcacaaaa aaaaaaaaaa aaaaaaaaaa aagggccggg cgcggtggct cacgcctgta atcccaacac tttgggaggc cgaggcgggc ggatcgcctg aggtcgggag atcaacatca tcctggccaa catggagaaa ccccgttctc tactaaaaat acaaaaaaaa attagccggg catggtggcg catgcctgta atcccagcta ctgggaggct gaggcaggag aatcacttga acccgggagg aggaggttgc agtgagccaa gatcgcgcca ctgcactcca gcgtgggcaa caagagcgaa actccatctc aagaaaaaag aaaaaagaa gaagttagtg ttcagaacag taggcgtagg ccccaaaaca aagcagtatc cttgaaaaag agaaattatg
```

-continued

```
ctaaattaag agacttaaga agaaagtgcg atctgaagta gatattgtcg tggacaagcc
agctataaaa gatgtcttag ggacagttga aaaataatca tataaaaggg ggggcatggt
ggttcgtgcc tgtaatctca gcacttcggg aggccgagga agaatcagta gagcccagga
gttggagacc agcctgagca acatagcaag accccatctt tacaaacaga aacaaaacag
ataaaggtcg ggtattcctt atggtacata ttgtataatg tggagactgc taactgaaaa
aagaaaaaaa tgtataaaaa atatgtattt acacccatgt tcattgatgc ataattcaca
atagtcaaaa ggtgaaagca atccagatgt cctctgtgga atgactggat aaacaaaatg
aagtatagac ctacaatgga atattattca gccttaaaaa gaaagaaaat tctgacccat
gccacaacgc ggaggaagct tgaagacatt atgctaagtg aaatacacca gacacaaaaa
gacaaatact gtgtgattcc acttagatca gatatctaaa gtagtcgaat tcatagaaat
tgaaagtaca atggtgattg ccaggggctg agaaaaggag aaaatgggga attctttcct
gagcacattt tcagttttgt aagatgaaaa agttctgaaa attggttgta caacgtgaat
atggtaaaca ctactgaact gtgtacttaa aaatggtgaa gatggtaaat gttatgatac
atgtgtttgg caattaaaat ttttttgtta gggccaggcg cggtggctcg cacctgtaat
cccagcactt tgggagggag aggagggagg atcactcgag cctagcagtt caagagtagc
ctggccaaca tggcaaaacc tgtctctgct aaaaatacaa aaattagttg gtacgttggt
gggcaactgc agtcccagct actcaggagg ctgaggcacg ataattgctt gaacccggga
ggcagaggct gcagtgagcc gagattgtat cactgcactc cagcctgaat gacggaggga
gattctgtct caaaaataat aataataata ataaaaata aataaatgaa gcactgtccc
acatattaga aggcttctag ccatcacagc ccctgctgtc taaagatacg catgtgtata
cctaaatgca cacacacaca taaaaaaagg tcaagaggat ataaattcag gtgctaaaat
aataatcact gactagtgag tatatttta ttttctttt tgtttgtcta tattttccaa
ttttcttcat gcatattttt tgcttttgta ataataaagc tcttttccca agttacggtc
ataaaacaca aataaataag aaagaaatga taggtagtga ggaagtcaat gcagagggcc
aacaactctt ggaaaatttg aaagcaaaag gagatggagt tgtatctaaa agacatcgct
gagtctagag tacctctttc tgtggcggcg agtcctctga aaatctggtg gggagagtgg
atgaagcttc tgccctcaga gaaatgagaa tatgtaaagt tgaagttttg catatcattt
taggtggtga tggaacttcc taaaaccctt tcgtgacctc aggttggaga cctccagtcc
agatattttt gtgtgtttac ttatttagct tatttgttta tttttaaaca cactgggtga
agaaaggagc cagtggaaaa accaagattg aaagtacaag aaagaggaga aatttacact
aatatggact tccagatgag gctgtgattt tgatacacac ataaatcaat acagtagatt
ttaaattgtc tatcatagga tgggcatggt ggctcatgcc tataatccca gcactttggg
aggccaaggc aggcagatca cccgaggtca ggagttcaag accagcctgg ccaacatggc
aaaacccgt ctctactaaa aatacaaaaa ttagccaggc gtggtggtgc acgcctgtaa
tcccagctac tctggaggct gaggcaggag aatcgcttga actcgggagg cggagcttac
agtgagctga aatcaatcca ctgcactcca gcctgcgcga cagaggaaga ctctgtctga
aaataatta ataaattaat aaataaatat aattgtctat cagagaatgc ttttatgtgg
tcccgtgtga ggtgaaggaa ggcaaactaa acagcgtgga ggaccttctg gtttcatgat
cccacatctt tatgtgggaa gattagaatc ctaagaatat gtatgcattt tcaaaaagat
actgtttgtt ttaacatttt tttcatcttt ttgcagaagt ttagcaatgg cgtctttctc
tgctgagacc aattcaactg acctactctc acagccatgg aatgagcccc cagtaattct
```

-continued

```
ctccatggtc attctcagcc ttactttttt actgggattg ccaggcaatg ggctggtgct gtgggtggct ggcctgaaga tgcagcggac agtgaacaca atttggttcc tccacctcac cttggcggac ctcctctgct gcctctcctt gcccttctcg ctggctcact tggctctcca gggacagtgg ccctacggca ggttcctatg caagctcatc ccctccatca ttgtcctcaa catgtttgcc agtgtcttcc tgcttactgc cattagcctg gatcgctgtc ttgtggtatt caagccaatc tggtgtcaga atcatcgcaa tgtagggatg gcctgctcta tctgtggatg tatctgggtg gtggcttttg tgatgtgcat tcctgtgttc gtgtaccggg aaatcttcac tacagacaac cataatagat gtggctacaa atttggtctc tccagctcat tagattatcc agactttat ggagatccac tagaaaacag gtctcttgaa acattgttc agccgcctgg agaaatgaat gataggttag atccttcctc tttccaaaca atgatcatc cttggacagt ccccactgtc ttccaacctc aaacatttca aagaccttct gcagattcac tccctagggg ttctgctagg ttaacaagtc aaaatctgta ttctaatgta tttaaacctg ctgatgtggt ctcacctaaa atccccagtg ggtttcctat tgaagatcac gaaaccagcc cactggataa ctctgatgct tttctctcta ctcatttaaa gctgttccct agcgcttcta gcaattcctt ctacgagtct gagctaccac aaggtttcca ggattattac aatttaggcc aattcacaga tgacgatcaa gtgccaacac ccctcgtggc aataacgatc actaggctag tggtgggttt cctgctgccc tctgttatca tgatagcctg ttacagcttc attgtcttcc gaatgcaaag gggccgcttc gccaagtctc agagcaaaac ctttcgagtg gccgtggtgg tggtggctgt ctttcttgtc tgctggactc cataccacat ttttggagtc ctgtcattgc ttactgaccc agaaactccc ttggggaaaa ctctgatgtc ctgggatcat gtatgcattg ctctagcatc tgccaatagt tgctttaatc ccttccttta tgccctcttg gggaaagatt ttaggaagaa agcaaggcag tccattcagg gaattctgga ggcagccttc agtgaggagc tcacacgttc cacccactgt ccctcaaaca atgtcatttc agaaagaaat agtacaactg tgtgaaaatg tggagcagcc aacaagcagg ggctcttagg caatcacata gtgaaagttt ataagaggat gaagtgatat ggtgagcagc ggacttcaaa aactgtcaaa gaatcaatcc agcggttctc aaacggtaca cagactattg acatcagcat cacctagaaa cttgttagaa atgcaaattc tcaagccgca tcccagactt gctgaatcgg aatctctggg ggttgggacc cagcaagggc acttaacaaa ccctcgtttc tgattaatgc taaatgtaag aatcattgta aacattagtt ctatttctat cccaaactaa gctatgtgaa ataagagaag ctactttgtt tttaaatgat gttgaatatt tgtcgatatt tccatcatta aatttttcct tagcattgtc taagtcttcc agattccatt taaaaccatt tcttgttctc ctacgtgagt gaaagatgat catatatcct aatgctttgt tgtcgtgtgg tgttgatggt tttaaacgaa agaaagtgc aaaaagaaaa tgcctgtgaa gacaagaagc catgagactg agtctggagc ataggttat gcaatgatgc ctgtccctgg gaacacccct gggtacagga tatagaaatt tccactatta catagagttt ccactattac aactaaataa gcatctattg tgtgaaaact gactcatgaa atgttatgaa agctgtggtt tggggagttc tgtttcttct aactgcctac cggttgggca cctatttcc actcctcttc ctaagctcct taatttcctt attactcccc agcctccaaa tcttccacat cagactttgt gcctcaaaca acctctaatt tcgtaagatt ctagttactc ccttcctctt gctccaaatg aatactttct aagaaagtat ttcaagtgga aggagaaaga gggtggagga tggagcagca attcttctac tctctgcaac tgagtacct accaggcttg ccatcacatt
```

-continued

```
ttaaaacatg acgacaggca acttacatgc caaaattacc aaatatatct tctgggtttt ttaaatcctt ttctttgcca aagtaataca tgcacatagt tttaaaataa tttaataagg tatataatga aatatgaggt ctcctacctc actgtgccca aaagttccct cctcccactc tcatttccca gagataatcc ttgcacaatt ttagatgttt cctttgataa ttatcatgat gtttctaaat catgtgctta tgctgctctt ttctggaggc atgataaaac gacttcttgt tttgaaagat gaagatgttt atccaagcac cccatatttt taatttgttt atccagcatc ccaacattca ttaataacca tattttaatt cattcatgac cacatatttt tcttctactt tgtctataca ctccaaccat ttatatagct ttccttctgt ccctttttca tttaaaacaa aattacctaa ctccctacca ccttctcatt tttctgtata tataaatgtt tgtgtcaaac gtctgaaatt tctggcttgt ttgtatcaca acgtggcctc atctaaacca aatacaatga tgtagtctaa aaacagaaaa tgacatgtgt tttagacctg caagacacta tctgttcaat ggctgaggtg agggtctgga ctacagattt tttataaagt atatgcagaa aaattacaaa tcactaggaa ttctttcagt tgtgaagaat gtctgacata agatttgaag tgctaccttt ccagcttata tattaatttg cttatatatt tgatatgaat aaatgctttt tttctcatgg gtccttgcga ggctcagaga tttatgaa
```

The amino acid sequence of human C3a receptor 1 (SEQ ID NO: 5).

```
MASFSAETNSTDLLSQPWNEPPVILSMVILSLTFLLGLPGNGLVLWVAGLKMQRTVNTIWFLHLTL

ADLLCCLSLPFSLAHLALQGQWPYGRFLCKLIPSIIVLNMFASVFLLTAISLDRCLVVFKPIWCQN

HRNVGMACSICGCIWVVAFVMCIPVFVYREIFTTDNHNRCGYKFGLSSSLDYPDFYGDPLENRSLE

NIVQPPGEMNDRLDPSSFQTNDHPWTVPTVFQPQTFQRPSADSLPRGSARLTSQNLYSNVFKPADV

VSPKIPSGFPIEDHETSPLDNSDAFLSTHLKLFPSASSNSFYESELPQGFQDYYNLGQFTDDDQVP

TPLVAITITRLVVGFLLPSVIMIACYSFIVFRMQRGRFAKSQSKTFRVAVVVVAVFLVCWTPYHIF

GVLSLLTDPETPLGKTLMSWDHVCIALASANSCFNPFLYALLGKDFRKKARQSIQGILEAAFSEEL

TRSTHCPSNNVISERNSTTV
```

The term "agonist" as disclosed herein refers to a substance which initiates a physiological response when combined with a receptor. Accordingly, agents which stimulate cell signalling via the human C3a receptor are agonists in accordance with the present invention. Suitably, human C3a receptor agonist can activate the C3a receptor. Suitably, the human C3a receptor agonist may be a ligand for the human C3a receptor. Suitably, the human C3a receptor agonist can trigger calcium ions mobilization in human myeloid cells such as blood monocytes or microglial cell, which can be measured in common in vitro assays using fluorescent calcium indicators.

In some aspects, a human C3a receptor agonist in accordance with the present invention is a C3a receptor agonist which stimulates a C3a receptor, following brain ischemic injury, to:
i. Stimulate neurogenesis in the peri-infarct region;
ii. Stimulate axonal and/or glial plasticity in the peri-infarct region;
iii. Increase the density of pre-synaptic terminals in the peri-infarct cortex;
iv. Increase the expression of GAP-43 in the peri-infarct cortex;
v. Improve functional recovery;
vi. Stimulates recovery of motor function;
vii. Reduces activation and/or proliferation of glial cells (astrocytes and/or microglial cells); or
viii. any combinations of i. to vii. above.

Methods for determining whether a C3a receptor agonist stimulates a C3a receptor to achieve such results are disclosed in the examples herein. Specifically, the methods utilising a C3a peptide as disclosed in the Examples can be used where the C3a peptide is replaced with a C3a receptor agonist to be tested.

Suitably, the human C3a receptor agonist may comprise arginine or the amino acid sequence Leu-Gly-Leu-Ala-Arg (SEQ ID NO: 1, positions 73-77) at the C-terminal. The pentapeptide Leu-Gly-Leu-Ala-Arg (SEQ ID NO: 1, positions 73-77) has been shown to be the minimal sequence required for C3a receptor activation.

Suitably, the human C3a receptor agonist may comprise amino acids 65 to 77 of SEQ ID NO: 1 or amino acids 57 to 77 of SEQ ID NO: 1, preferably at the C-terminal. However, any fragments of a C3a peptide, such as the human C3a peptide, which can activate a human C3a receptor are encompassed.

Suitably, the human C3a receptor agonist may be a functional fragment or functional ortholog or a functional variant of a naturally occurring C3a peptide, such as a functional fragment or functional ortholog or a functional variant of a human C3a peptide as set forth in SEQ ID NO: 1.

Suitably, the human C3a receptor agonist may be a human C3a as shown in SEQ ID NO: 1 or a C3a receptor agonist having at least 70% identity, or at least 75% identity or at least 80% identity or at least 85% identity or at least 90% identity or at least 95% identity thereto across its entire length.

Virtually all naturally occurring C3a sequences comprise six cysteine residues to positions equivalent to positions 22, 23, 36, 49, 56 and 57 of SEQ ID NO: 1. Suitably, functional variants of a C3a peptide may conserve some or all of these cysteine residues. Generally, the arrangement of basic amino acids are observed across C3a orthologs. Hence, functional variants of a C3a peptide may conserve or have conservative substitutions of basic amino acids.

In contrast to C-terminal portion (residues 58 to 77 of SEQ ID NO: 1), the N-terminal portion (residues 1 to 21) is not highly conserved and modification at the N-terminal portion with hydrophobic residues or hydrophobic moieties have been shown to increase potency—see Klos et al., Pharmacological reviews, January 2013, 65(1) 500-543 the content of which are incorporated herein by reference. Thus, suitably functional variants of a C3a peptide may have substitutions or modifications within the N-terminal domain.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in protein is preferably replaced with another amino acid residue from the same side chain family. Alternatively, in another embodiment, mutations can be introduced randomly along all or part of coding sequences, such as by saturation mutagenesis, and the resultant mutants can be screened for biological activity to identify mutants that retain activity as a human C3a receptor agonist. Following mutagenesis of SEQ ID NO: 1, the encoded proteins can be expressed recombinantly and the protein can be tested for human C3a receptor agonist activity.

As used herein, a "functional fragment" of protein is one which retains activity as a human C3a receptor agonist as defined herein. Suitably, the functional fragment may be 5 or more amino acids, such as 5 or more amino acids of the C-terminal of SEQ ID NO: 1 or another a C3a peptide ortholog.

Calculations of sequence homology or identity (the terms are used interchangeably herein) between sequences are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 75%, 80%, 82%, 84%, 85%, 86%, 87%, 88%, 89%, 90%, 91%, 92%, 93%, 94%, 95%, 96%, 97%, 98%, 99%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman et al. (1970) J. Mol. Biol. 48:444-453) algorithm which has been incorporated into the GAP program in the GCG software package (available at http COLON SLASH SLASH www.gcg.com), using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at at http COLON SLASH SLASH www.gcg-.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a BLOSUM 62 scoring matrix with a gap penalty of 12, a gap extend penalty of 4, and a frameshift gap penalty of 5.

Alternatively, the percent identity between two amino acid or nucleotide sequences can be determined using the algorithm of Meyers et al. (1989) *CABIOS* 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and X BLAST programs (version 2.0) of Altschul, et al. (1990) J. Mol. Biol. 215: 403-410). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, gapped BLAST can be utilized as described in Altschul et al. (1997, Nucl. Acids Res. 25:3389-3402). When using BLAST and gapped BLAST programs, the default parameters of the respective programs (e.g., XBLAST and NBLAST) can be used. See http COLON SLASH SLASH www.ncbi.nlm.nih.gov.

Preferably where the C3a receptor is a polypeptide, the polypeptide is not a native polypeptide. In this regard, the term "native polypeptide" or "naturally occurring polypeptide" means an entire polypeptide that is in its native environment and when it has been expressed by its native nucleotide sequence. Typically, the nucleotide sequence encoding polypeptides having the specific properties as defined herein is prepared using recombinant DNA techniques (i.e. recombinant DNA). However, in an alternative embodiment of the invention, the nucleotide sequence could be synthesised, in whole or in part, using chemical methods well known in the art (see Caruthers MH et al (1980) Nuc Acids Res Symp Ser 215-23 and Horn T et al (1980) Nuc Acids Res Symp Ser 225-232).

As used herein, the term "recombinant" refers to a biomolecule, for example a gene or a protein that (1) has been removed from its naturally occurring (native) environment, (2) is not associated with all or a portion of a nucleic acid molecule or protein as it is found in nature, (3) is operatively linked to a polynucleotide or polypeptide which it is not linked to in nature, or (4) does not occur in nature.

A C3a receptor agonist may be encoded by a nucleic sequence capable of hybridising to the complement of a nucleotide sequence encoding SEQ ID NO: 1 of a functional fragment thereof.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences encoding a human C3a receptor agonist that are capable of hybridising to the sequences that are complementary to the sequences encoding a C3a peptide discussed herein, or any functional fragment thereof.

Hybridisation conditions are based on the melting temperature (Tm) of the nucleotide binding complex, as taught in Berger and Kimmel (1987, Guide to Molecular Cloning Techniques, Methods in Enzymology, Vol. 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical nucleotide sequences while an intermediate (or low) stringency hybridisation can be used to identify or detect similar or related polynucleotide sequences.

Preferably, the present invention encompasses the use of sequences encoding a human C3a receptor agonist that are complementary to sequences that are capable of hybridising under high stringency conditions or intermediate stringency conditions to nucleotide sequences encoding a C3a peptide.

More preferably, the present invention encompasses the use of sequences encoding a human receptor agonist that are complementary to sequences that are capable of hybridising under high stringency conditions (e.g. 65° C. and 0.1×SSC [1×SSC-0.15 M NaCl, 0.015 M Na-citrate pH 7.0]) to nucleotide sequences encoding C3a peptide (such as SEQ ID NO: 1).

Suitably, the C3a receptor agonist may be selected from the group consisting of: a C3a peptide;
Trp-Trp-Gly-Lys-Lys-Tyr-Arg-Ala-Ser-Lys-Leu-Gly-Leu-Ala-Arg (SEQ ID NO: 2) and its derivatives (as described by Bellows-Peterson et al., 2012, J Med Chem, 55(9): 4159-4168); Hexapeptides (as disclosed in Scully et al, 2010, J. Med. Chem., 53; 4938-4948): Phe-Leu-Pro-Leu-Ala-Arg (SEQ ID NO: 3); Phe-Ile-Pro-Leu-Ala-Arg (SEQ ID NO: 6); Phe-Trp-Thr-Leu-Ala-Arg (SEQ ID NO: 7); Phe-Leu-Thr-Leu-Ala-Arg (SEQ ID NO: 8) and their derivatives;

oxazole peptidomimetics: Boc-Leu-oxazole-Arg; Boc-Ile-oxazole-Arg; Boc-Ile-5-methyl-oxazole-Arg; 3-indole-carboxylic acid-Leu-imidazole-Arg; 3-indole-carboxylic acid-Leu-oxazole-Arg; 5-bromonicotinic acid-Leu-oxazole-Arg; 4-(biphenyl-4-yl)-4-oxobutanoic acid-Ile-oxazole-Arg; isoquinoline-1-Ile-oxazole-Arg and their derivatives (as described in Reid et al, 2013, Nat Communic., 4:2802 and Singh et al, 2015, Bioorg Med Chem Lett.; 25(23):5604-8), both incorporated herein by reference in their entirety; imidazole peptidomimetics: (2-Benzhydryl-4-methyl-1H-imidazole-5-carbonyl)-L-Arg; (2-Benzhydryl-1H-imidazole-5-carbonyl)-L-Arg; (2-Benzhydryl-1,5-dimethyl-1H-imidazole-4-carbonyl)-L-Arg and their derivatives (as described in Reid et al, 2013, Nat Communic., 4:2802 and Reid et al, 2014, J Med Chem., 57(20): 8459-70); and non-arginine compounds: 2-cyclohexyl-2-phenyl-N-[1-(3-pyridin-3-ylpropanoyl)piperidin-4-yl]acetamide and their derivatives (as described by Denonne et al, 2007, Discovery of new C3aR ligands. Part 2: amino-piperidine derivatives. Bioorg Med Chem Lett. 17(12):3262-5) or compounds described in US patent publication no. 2008/0188528 A1, incorporated herein by reference in its entirety and specifically for its description of C3a receptor agonist compounds and how to make them.

A C3a receptor agonist as provided herein may be part of a composition (e.g. a pharmaceutical composition) that comprises the C3a receptor agonist and one or more other components. A composition may be a composition that comprises a C3a receptor agonist of the invention and a pharmaceutically acceptable excipient, adjuvant, diluent and/or carrier. Compositions may routinely contain pharmaceutically acceptable concentrations of salt, buffering agents, preservatives, compatible carriers, supplementary immune potentiating agents such as adjuvants and cytokines and optionally other therapeutic agents or compounds.

As used herein, "pharmaceutically acceptable" refers to a material that is not biologically or otherwise undesirable, i.e., the material may be administered to an individual along with the selected C3a receptor agonist without causing any undesirable biological effects or interacting in a deleterious manner with any of the other components of the pharmaceutical composition in which it is contained.

Excipients are natural or synthetic substances formulated alongside an active ingredient (e.g. a neurotoxin as provided herein), included for the purpose of bulking-up the formulation or to confer a therapeutic enhancement on the active ingredient in the final dosage form, such as facilitating drug absorption or solubility. Excipients can also be useful in the manufacturing process, to aid in the handling of the active substance concerned such as by facilitating powder flowability or non-stick properties, in addition to aiding in vitro stability such as prevention of denaturation over the expected shelf life. Pharmaceutically acceptable excipients are well known in the art. A suitable excipient is therefore easily identifiable by one of ordinary skill in the art. By way of example, suitable pharmaceutically acceptable excipients include water, saline, aqueous dextrose, glycerol, ethanol, and the like.

Adjuvants are pharmacological and/or immunological agents that modify the effect of other agents in a formulation. Pharmaceutically acceptable adjuvants are well known in the art. A suitable adjuvant is therefore easily identifiable by one of ordinary skill in the art.

Diluents are diluting agents. Pharmaceutically acceptable diluents are well known in the art. A suitable diluent is therefore easily identifiable by one of ordinary skill in the art.

Carriers are non-toxic to recipients at the dosages and concentrations employed and are compatible with other ingredients of the formulation. The term "carrier" denotes an organic or inorganic ingredient, natural or synthetic, with which the active ingredient is combined to facilitate the application. Pharmaceutically acceptable carriers are well known in the art. A suitable carrier is therefore easily identifiable by one of ordinary skill in the art.

Suitably, the C3a receptor agonist may be in a composition comprising a pharmaceutically acceptable carrier. Suitably, the composition is formulated for intranasal delivery. Suitably, the medicament formulated for intranasal administration may be a composition comprising the C3a receptor agonist and a pharmaceutically acceptable carrier, such as a buffer (e.g. phosphate buffered saline). In one embodiment of the invention, the composition of the invention may comprise a galenical gel formulation of an agonist, wherein such formulation comprises of thickening and gelling agents such as for example of colloidal silicon dioxide, cellulose and cellulose derivatives, polysaccharides, polyvinyl alcohol and like. A pharmaceutical formulation may comprise a lypophylic transport/carrier moiety such as fatty acid, for example caprylic acid, lauric acid, oleic acid, linoleic acid, or arachidonic acid, or mixtures thereof. Mucoadhesive agents, e.g., sodium hyaluronate, chitosan, acrylic acid derivatives, lectin, and low methylated pectin, surface-engineered nanoparticles, efflux transporter inhibitors, and vasoconstrictors, may be used to reduce clearance, to prolong the residence time of the formulation at the delivery site, and to increase transport from the nasal epithelium to the brain.

C3a receptor agonists and compositions comprising the same are useful in the treatment or prevention of one or more of: an ischemic brain injury, stroke, traumatic brain injury, spinal cord injury and neurodegenerative disorders.

Advantageously, a human C3a receptor agonist may stimulate neural plasticity. Neural plasticity that includes changes in function and number of synapses, sprouting of axons and dendrites which leads to representational map shifts (Filli and Schwab, 2015; Hilton et al., 2016; Horner and Gage, 2000; Murphy and Corbett, 2009), together with neurogenesis (Marlier et al., 2015; Sun et al., 2015) and distinct glial responses (Burda et al., 2016; Loane and Byrnes, 2010; Pekny et al., 2014), play a critical role in recovery from various types of CNS insults. These plasticity processes are a basic substrate mediating not only spontaneous but also rehabilitation-enhanced functional recovery after brain and spinal cord injuries (Goldshmit et al., 2008; Mestriner et al., 2011; Nakagawa et al., 2013; Shiromoto et al., 2016; Tamakoshi et al., 2014; Warraich and Kleim, 2010). Neural plasticity and its impairment appear to be a pathogenic contributor to development of some neurodegenerative diseases. For example, loss of synapses is among the first steps of neurodegeneration in Parkinson's (Bellucci et al., 2016) and Alzheimer's disease, where it is accompanied also by a reduction in dendritic complexity (Mufson et al., 2015; Scheff et al., 2006). Synapse loss in the spinal cord is characteristic for progression of motor neuron diseases such as amyotrophic lateral sclerosis (Zang et al., 2005). Therefore, promotion of reactive synaptogenesis as well as replacement of dying neurons and glial cells through the process of cell genesis appears as potential therapeutic modality in these diseases. Furthermore, neurotrophins, such as nerve growth factor released by microglia and astrocytes upon stimulation with C3a (Heese et al., 1998; Jauneau et al., 2006), may limit neuronal loss in chronic neurodegenerative conditions by providing a trophic support (Chen et al., 2012; Dawbarn and Allen, 2003). For those reasons, stimulating neural plasticity such as achieved by intranasal administration of C3a receptor agonists is expected to have positive effects also in neurological conditions other than ischemic brain injury, for example hemorrhagic stroke, traumatic brain injury, spinal cord injury, neurodegenerative disorders such as Alzheimer's disease, Parkinson's disease, amyotrophic lateral sclerosis.

Accordingly, a C3a receptor agonist of the invention or a composition comprising a C3a receptor agonist of the invention may have utility in the treatment or prevention of one or more of: an ischemic brain injury, stroke, traumatic brain injury, spinal cord injury and neurodegenerative disorders.

Neurodegenerative disorders as used herein includes neurodegenerative diseases in which impairment of neural plasticity is a factor in the development of the disease such as in Parkinson's and Alzheimer's disease and further includes motor neuron diseases such as amyotrophic lateral sclerosis. Suitably, the neurodegenerative disorder may be selected from: Parkinson's disease, Alzheimer's disease and amyotrophic lateral sclerosis.

An "ischemic brain injury" as used herein refers to a brain injury which results from insufficient blood flow to the brain to meet metabolic domain. Insufficient blood flow can lead to ischemia and result in death of brain tissue or ischemic stroke.

Suitably, the ischemic brain injury may be the result of focal ischemia or global ischemia.

Suitably, the ischemic brain injury may be one or more of the following: ischemic stroke, neonatal hypoxic-ischemic encephalopathy and focal cerebral ischemia.

Suitably, the ischemic brain injury may be ischemic stroke. It has been surprisingly found that a C3a receptor agonist has particular utility in the treatment or prevention of ischemic brain injury resulting from ischemic stroke.

Advantageously, a human C3a receptor agonist may increase the density of pre-synaptic terminals, such as pre-synaptic glutamergic terminals. Suitably, the human C3a receptor agonist may increase the density of synapsin $I^+$ puncta and/or $VGLUT1^+$ puncta in the infarct-proximal region.

Advantageously, a human C3a receptor agonist may stimulate axonal, per-synaptic and/or glial plasticity after ischemia. Suitably, the human C3a receptor agonist may increase the density of $GAP-43^+$ puncta in the proximal ipsilesional somatosensory cortex and in the contralesional cortical region.

Advantageously, a human C3a receptor agonist may improve functional recovery following ischemia.

Advantageously, a human C3a receptor agonist may stimulate neural plasticity in the peri-infarct cortex. Without wishing to be bound by theory, increased density of synapsin $I^+$ puncta in deep cortical layers of the peri-infarct cortex associates with improvement of functional recovery.

Suitably, a human C3a receptor agonist or a composition comprising the same formulated for intranasal delivery may advantageously be administered after the active (acute and subacute) phase of the stroke. For example, 7 days after the ischemic stroke may result in one or more of the advantageous effects disclosed herein.

Suitably, a human C3a receptor agonist or a composition comprising the same formulated for intranasal delivery may advantageously fulfil the clinical need for drugs for treating chronic ischemic stroke.

Suitably, the ischemic brain injury may be neonatal hypoxic-ischemic encephalopathy.

Advantageously, a C3a receptor agonist may ameliorate hypoxia-induced reactive gliosis.

In another aspect, the present invention relates to a device for intranasal administration of a human C3a receptor agonist, wherein the device comprises a composition comprising a human C3a receptor agonist of the invention and a pharmaceutically acceptable carrier. Suitably, the device may be an intranasal spray device comprising a bottle, pump and an actuator. Suitably, the device may be a unit dose device or a multiple dose device.

The delivery device can include, but is not limited to, unit dose containers, pump sprays, airless and preservative-free sprays, nebulizers, dose inhalers and pressurized dose inhalers, droppers, squeeze bottles, a nasal tampon, or a nasal sponge, together with a suitable applicator. Type of device will depend on the formulation of the C3a receptor agonist and can deliver an aerosol, drops or gel depots. Suitably, the device should provide for delivery of a C3a receptor agonist high in the nasal cavity so as to reach the olfactory epithelium, thereby maximizing delivery to the brain and limiting the delivery to the respiratory region of nasal cavity or throat thus preventing deposition of a drug in the lungs or stomach. Different approaches to satisfy such delivery requirement are known in the art (Ilium, "Intranasal delivery to the central nervous system" (2015) in "Blood-Brain Barrier in Drug Discovery: Optimizing Brain Exposure of CNS Drugs and Minimizing Brain Side Effects for Peripheral Drugs", pp. 535-565, DOI: 10.1002/9781118788523. ch 25, incorporated herein by reference). Examples of potentially suitable devices for aerosol delivery are: Impel NeuroPharma's POD device as described in US patent publication no. 20170043109 A1; ViaNase CPD device (Kurve Technology) as described in U.S. Pat. No. 8,001,963 B2; or Bi-directional device (OptiNose) as described in U.S. Pat. No. 6,715,485 B1, all incorporated herein by reference in their entirety.

In a further aspect, the present invention relates to a kit comprising a device in accordance with the invention and instructions for use. Such instructions may be in accordance with any administration regimen detailed herein.

Human C3a receptor agonists and compositions comprising the same are formulated for intranasal administration. Such formulations may provide a therapeutically effective amount of a C3a receptor agonist required for the dosing regimen selected. Suitably, the human C3a receptor agonists and compositions may be formulated to provide a therapeutically effective amount in a single intranasal dose daily, weekly or monthly or the human C3a receptor agonists and compositions may be formulated to provide a therapeutically effective amount in multiple doses over the same time periods.

By "multiple doses" it is meant two or more doses. Suitably, the multiple does may be between 2 and 6 times a day or every two days, every three days, every four days, every five days, every week.

Suitably, "a therapeutically effective amount" may in the range of about 0.1 nanogram to about 500 milligrams per kilogram of body weight per day.

Suitably the device of the invention may be dimensioned to contain enough C3a receptor agonist or composition comprising same for the subject's treatment.

The invention will now be further described by way of Examples, which are meant to serve to assist one of ordinary skill in the art in carrying out the invention and are not intended in any way to limit the scope of the invention.

EXAMPLES

Materials and Methods
Animals $C3aR^{-/-}$ mice (Kildsgaard et al., 2000) were backcrossed onto the C57BL/6J genetic background (Jackson Laboratories) for 10 generations. Heterozygous mice were then intercrossed to generate homozygous $C3aR^{-/-}$ mice. WT C57BL/6J mice served as controls. GFAP-C3a mice on a C57BL6/CNr genetic background were generated as previously described (Boos et al., 2004) and their WT littermates were used as controls. Male, 7- to 9-month-old mice weighing between 35-45 g were used: $C3aR^{-/-}$ (n=14), $C3aR^{+/+}$ (n=10), GFAP-C3a (n=12) and WT (n=13). For the treatment experiments, male, 5-month-old WT C57BL/6CNr mice (Charles River), weighing 30-35 g were used. For in vivo imaging of fluorescent peptide translocation after intranasal administration, 2.5-month-old male C57BL/6 Albino mice (Charles River) were used. Mice were housed under standard conditions on a 12 h light/12 h dark cycle with food and water ad libitum. All experiments were conducted according to protocols approved by the Ethics Committee of the University of Gothenburg (permit number: 146-2008, 170-2009, 308-2012, 41-2015).

Photothrombotic Stroke Induction

Cortical photothrombosis was induced using the Rose Bengal method (Lee et al., 2007; Watson et al., 1985) with some modifications. Anesthesia was induced with isoflurane (Forene®, Abbott) in air and oxygen (1:1) initially at 5% and reduced to 2.5% during the surgical procedure. Body temperature was monitored by a rectal probe and maintained at 37° C. using a homeothermic control unit (Harvard Apparatus). Anesthetized mice were placed in a stereotaxic frame, the skull was exposed through a midline scalp incision and Rose Bengal (200 µl, 10 mg/ml solution in sterile saline, Sigma) was injected intraperitoneally. After 5 min, the skull and underlying brain tissue were illuminated for 12 min by a 2 mm diameter cold laser beam (50 mW, 561 nm; Cobolt AB) positioned at AP +0.5 mm and ML −2.7 mm relative to Bregma, targeting the border between left primary somatosensory and motor cortex (Porritt et al., 2012). For intervention experiments targeting motor cortex, stroke was induced as above with the following modifications: Transcranial illumination lasting 15 min was delivered using cold light source (LQ1600, Fiberoptic-Heim AG) equipped with 2 mm wide fiber optic probe and directed to AP +0 and ML −1.5 relative to Bregma. After illumination, the scalp was sutured and mice were placed in a warm cage for 45 min to recover from anesthesia prior to being returned to the home cage. Mice were provided with moist mashed food placed on the floor of the home cage and their weight was monitored daily for 7 days after surgery. There were no significant differences in body weight, body temperature (36.5±0.5° C.), duration of surgery, or post-stroke mortality between cohorts. Each cohort contained an even distribution of mice from the matched strains or treatment groups.

Intranasal Treatment

Purified human C3a peptide (Complement Technologies) was diluted in sterile phosphate buffered saline (PBS) to a concentration of 200 nM and a total of 20 µl (10 µl/nostril; corresponding to approximately 1.13 µg/kg body weight) of peptide solution or PBS was given intranasally to awake, hand-restrained mice held in a supine position. Solutions were administered through a pipette tip, drop-wise in 5 µl portions divided by 1 min intervals to allow for absorption. C3a or PBS was given every 24 hours on days 7 to 21 post-stroke for the short-term study or on days 7 to 28 post-stroke for the long-term study. Mice were assigned to C3a or PBS treatment using randomization stratified by body weight to avoid potential confounding effects of body weight on behavioural performance. The investigators carrying out behavioural studies and analysing data were blinded to treatment group. For the assessment of potential systemic anaphylactic response due to intranasal C3a inoculation, body temperature was monitored using a rectal temperature probe (Harvard Apparatus) inserted approximately 4 mm into the rectum of awake mice restrained by the scruff. Baseline temperature was taken before intranasal administration and 5, 15, 30, 45 and 75 min after C3a or PBS administration.

In Vivo Epifluorescent Imaging

C3a (Complement Technologies) was labelled with VivoTag XL 680 fluorescent tag (Perkin Elmer) and purified according to manufacturer's instructions. A minimum of 10 µg of labelled C3a (0.4 mg/kg of body weight) was determined in a pilot experiment to be necessary for reliable detection of the fluorescent signal in live animals due to its significant attenuation by skull bones. Mice received 20 µl of PBS or 65 µM C3a-VivoTag (0.48 mg/kg of body weight) intranasally as described above. One and three hours later, mice were anesthetized with 2% isoflurane and imaged in the IVIS Lumina III Bio-imaging platform (Caliper Technologies). After imaging, mice were deeply anesthetized with isoflurane and killed by cervical dislocation for ex vivo imaging. Brains were quickly dissected from the skull and imaged using the same fluorescent filter sets. All mice and brains were imaged simultaneously with the PBS-treated control (acting as the tissue autofluorescence reference) placed in the middle, to minimize the potential confound of weaker illumination toward the sides of the observation field. Acquired images were processed and analysed using Living Image software (Caliper Technologies). Epifluorescent signal intensities are presented as radiant efficiency [(photons/sec/cm$^2$/sr)/(µW/cm$^2$)] after subtraction of the residual tissue autofluorescence signal defined by the PBS control.

Tissue Preparation and Infarct Volume Measurements

Twenty-one days after ischemia induction, mice were deeply anesthetized with thiopental (Hospira) and transcardially perfused with 0.9% saline, followed by 4% paraformaldehyde in 0.1 M PBS. Brains were removed and immersed in the same fixative overnight. Tissue was dehydrated, embedded in paraffin, and cut into 6-µm serial coronal sections. Every 20 th section was stained with hematoxylin and eosin (HE). Infarct size was evaluated morphometrically on digital images with ImageJ software (NIH, ver. 1.47q) by manual delineation of the infarct and hemisphere areas on sections spanning the entire lesion along the anterior-posterior axis by an investigator blinded to experimental group. Volume of injury was derived by multiplying area of total tissue loss that includes shrinkage due to scarring [(contralesional hemisphere–ipsilesional hemisphere)+infarcted tissue] on each section by the total inter-section distance.

Tissue Immunostaining

For immunofluorescent evaluation, sections were deparaffinized, heated three times for 5 min in a microwave oven in 0.01 M citric buffer (pH 6.0), and blocked in PBS containing 0.05% Tween-20 (Sigma) and 1% in Bovine serum albumin (BSA, Sigma) for GAP-43 and synapsin I staining, 3% normal goat serum for VGLUT1 staining or 4% normal donkey serum for GAP-43 double stainings. Goat anti-synapsin Ia/b antibody (1:150; Santa Cruz, sc-7379) was followed by biotin-conjugated donkey anti-goat immunoglobulin (Ig) secondary antibody (1:200; Jackson Research Lab, 705-065-147) and Cy3-conjugated streptavidin (1:100; Sigma). Guinea pig anti-VGLUT1 (1:500; Millipore, AB5905) was followed by Alexa Fluor 488 goat anti-guinea pig Ig (1:500; Molecular Probes, A11073). For single staining, mouse anti-GAP-43 antibody (1:1000; Millipore, MAB347), was followed by biotinylated rabbit anti-mouse Ig secondary antibody (1:200; Dako, E0354) and Cy3-conjugated streptavidin (1:100; Sigma). For double stainings, mouse anti-GAP-43 antibody (1:250; Millipore) together with either rabbit anti-synaptophysin antibody (1:200; Millipore, 04-1019), rabbit anti-β3-tubulin (1:200; Covance, Covance PRB-435P), rabbit anti-GFAP (1:200; Dako, Z0334) or rabbit-anti-S100β (1:200; Dako, Z0311), were followed by a mixture of donkey anti-mouse-Alexa555 (1:250, Molecular Probes, A31570), donkey anti-rabbit-Alexa488 (1:250 for synaptophysin and β3-tubullin or 1:2000 for S100β and GFAP; Molecular Probes, A11034) and DAPI (0.5 µg/ml; Molecular Probes, D1306). All antibodies and dye-conjugates were diluted in the respective blocking buffer. Sections representing all experimental groups were stained simultaneously, when more than one round of staining was necessary due to large number of slides. Sections stained with only the secondary antibody served as negative control, and no signal was observed for any secondary antibody including antibodies against mouse Ig.

Image Acquisition and Analysis

Highest signal intensity single plane images of immunostained sections were obtained by laser scanning confocal microscope (LSM TCS SP2, Leica Microsystems, ×63/NA 1.3 objective for synapsin I and GAP-43; and LSM 700, Carl Zeiss for VGLUT1 ×40/NA 1.3) at 1024×1024 pixels resolution. Images from a 238 µm×238 µm optical field (Synapsin I and GAP-43) or 160 µm×160 µm (for VGLUT1) were taken from two adjacent but not overlapping optical fields (referred to as proximal and distal) in the medial (motor) and lateral (somatosensory) peri-infarct cortex, each at superficial (I-IV) and deep (V-VI) cortical layers as well as at two depths in medial and lateral dorsal striatum (total of 4 images per region). Corresponding images were taken in the contralesional hemisphere and corpus callosum, the latter serving as an internal background control. Images were acquired in a standardized way including controlled and standardized exposure time and number of exposures. As there were no significant differences in the parameters of fluorescence-positive GAP-43+ puncta between cortical layers, these data were pooled and expressed as values per entire region. Similar values of all parameters for punctate staining in medial and lateral regions within the contralesional hemisphere were obtained for mice with sensorimotor stroke, so these values were pooled. Three standard sections per animal in 160 µm intervals were analysed. All sections were scanned with the same acquisition parameters.

For co-localization analysis, peri-infarct region of sections double-stained for GAP-43 and neuronal or glial markers were imaged with ×63/NA 1.4 objective (LSM 700, Zeiss) using sequential scanning mode with a 20 nm-wide exclusion window at emission spectra overlap to avoid any potential mixing of signal from the two channels. Images were collected as Z-stacks (voxel size: 0.09 µm×0.09 µm×0.34 µm—optical thickness) using 16-bit color space.

Single-stained images were analysed using MetaMorph® software (Molecular Devices, ver. 2.8.5) to obtain number, average size and intensity of positive punctuate structures per image. Average intensity per punctum was highly homogenous between the groups and regions; therefore this measure was not pursued further. Co-localization analysis was performed with ImageJ (ver. 2.0; Coloc2 plugin) using automatic thresholding and statistical verification of non-random findings (estimated probability of random co-localization P=1.0) according to Costes' method, following background subtraction. An experimenter blinded to experimental group performed all image acquisitions and quantifications.

Behavioural Assessment

Functional impairment of mice treated intranasally with C3a or vehicle was assessed using a modified cylinder test and a grid walking task to closely evaluate forepaw function. Mice were tested once on each task one week before stroke induction to establish baseline performance. Next, they were tested on days 7, 14 and 21 (short-term study) or days 7, 14, 28, 42 and 56 (long-term study) post-stroke. Behavioural assessments were carried out at approximately the same time each day, during the first half of light cycle. The experimenter scoring behaviour was blinded to treatment group. Due to larger than expected behavioural variation within groups in terms of scores at baseline and impairment following stroke, and in order to increase power for detection of differences, plotted scores are presented and analysed as ratio between score on a particular day and baseline score for each individual mouse (i.e., as fold of baseline performance).

Grid walking task: Mice were allowed to walk on a 35 cm×25 cm wire grid with 11-mm square mesh fixed 60 cm above the lab bench for 5 min as described previously (Baskin et al., 2003). A camera was placed beneath the grid to record video for later assessment of stepping errors (foot faults). Total foot faults for each forelimb, along with non-foot fault steps for that forelimb, were counted during frame-by-frame analysis of the videos. A ratio between the number of foot faults and total number of steps taken for the affected paw was calculated [#R foot faults/(#R foot faults+#R non-foot fault steps)]. A step was considered a foot fault if it was not providing support and the foot passed through the grid hole. If an animal was resting with the grid at the level of the wrist after a foot slip, this was also considered a fault. Foot fault scores are presented as fold of baseline performance.

Spontaneous forelimb asymmetry task (cylinder test): The method of Schallert and colleagues (Schallert et al., 2000) was used with minor modifications. Mice were videotaped with an HD digital camera while rearing in a 15-cm wide Plexiglas cylinder until they performed 10 rears (5-10 min). Two mirrors were arranged at 90° angle and placed behind the cylinder to assist with detailed analysis of all movements. All paw contacts with the cylinder wall during vertical exploration were scored on videos played back frame-by-frame. Due to marked muscle weakness resulting from injury to primary motor cortex, mice often place the other paw to support the body while rearing after initial single paw contact. Therefore, forelimb asymmetry index for mice was calculated as the percentage of individual right (affected) paw touches to total paw touches [R contacts/(R contacts+L contacts+both paws contacts)]. Asymmetry score is presented as fold of baseline performance.

Statistical Analysis

Sample size required for detection of significant differences with 80% power and significance level at α=0.05 was determined in a pilot study using WT untreated animals, and was estimated to be between 9 and 12, for infarct size compressions and behavioural experiments, respectively. Longitudinal behavioural data were analysed by two-way repeated measures ANOVA followed by Dunnett's post-hoc tests for within-group comparisons between specific time points or Sidak's post-hoc tests for between-group comparisons at particular time points. Other types of data were analysed by unpaired t-test for comparisons between two groups or one-way ANOVA followed by planned multiple comparisons using Sidak's method for comparisons between more than two groups. For data sets with non-Gaussian distribution, as determined by omnibus K2 normality test, non-parametric equivalents of the above mentioned tests were used. Specifically, behavioural data were analysed by Friedmann's test followed by Dunn's post-hoc test or Wilcoxon signed ranked test for within-group comparisons, and Mann-Whitney U test for between-group comparisons at individual time points. For other comparisons, a Kruskal-Wallis test followed by Dunn's post hoc analysis was applied. Association between density and size of synapsin I$^+$ puncta and behavioural performance was determined by simple linear regression. Pearson's linear correlation was used to determine the association between density of synapsin I$^+$ and VGLUT1$^+$ puncta. Reported P-values are adjusted for multiple comparisons where applicable. Data are presented as mean±SEM or median±interquartile ranges (IQRs). All analyses were two-tailed, and P values <0.05 were considered statistically significant. Analyses were performed in Prism (GraphPad Inc.; ver. 6.05f).

Exclusion of data points: In the analysis of neural plasticity markers, occasional extreme values scored for single images that were confirmed to be due to tissue section artifacts were excluded from the analysis. Such outliers were defined as values differing by >2*SD from the mean value for the parameter or by >1.5*IQR from the median for non-normally distributed data. Animals that displayed marked left paw preference (UR paw contacts >1.50 vs. median ratio of 0.94) in the cylinder task at baseline and consequently did not show a significant impairment in the targeted (right) paw function after stroke, despite the presence of lesion of the expected size, were excluded from the analysis of this behavioural task. This criterion was established prior to the study and was based on the inventors' previous observations. Since these mice did not display any marked difference in other parameters, they were not excluded from the remaining analyses so as not to unnecessarily reduce the group size. Distribution of outliers was comparable between experimental groups and the numbers of included and excluded animals are reported in the figures and figure legends.

Results

Signalling through C3aR Positively Regulates the Number of Synapses in the Contralesional Hemisphere Photothrombotic stroke was induced in the left cortex at the border between primary motor and primary somatosensory cortical areas corresponding to the forelimb. Morphometric analysis of the infarct volume 21 days after stroke induction did not show any significant difference in the extent of brain tissue loss between C3aR$^{-/-}$ and C3aR$^{+/+}$ mice (P=0.065) or between GFAP-C3a mice and their WT littermates (P=0.081), although there was a trend toward larger infarct volume in both groups of genetically modified mice.

To assess post-stroke changes in synaptic and axonal plasticity, the inventors visualized the pre-synaptic terminals by immunostaining with antibodies against a pan-synaptic marker synapsin I and used high-content image analysis to quantify synapsin I immunoreactive puncta in the peri-infarct region and the corresponding regions of the contralesional hemisphere. In all four experimental groups, the inventors found significantly higher density of synapsin I$^+$ puncta in the injured cortex proximal to the infarct (FIG. 1B-C), and this difference was more pronounced in somatosensory cortex than in motor cortex. Although the density of synapsin I$^+$ puncta in the ipsilesional hemisphere was comparable between groups, it was reduced by 50% in the contralesional cortex of C3aR$^{-/-}$ mice (P=0.001, P=0.032 in superficial and deep cortical layers, respectively, FIG. 1B). In all experimental groups, the average size of synapsin I$^+$ puncta in the infarct-proximal region was increased in the ipsilesional compared with the contralesional cortex. There was a marked overall reduction in the density of synapsin I$^+$ puncta in the contralesional cortex of C3aR$^{-/-}$ mice compared with C3aR$^{+/+}$ mice in areas corresponding to distal peri-infarct regions. C3aR$^{-/-}$ mice had fewer synapsin I$^+$ puncta in the deep layers of distal ipsilesional (i.e., secondary) motor cortex than C3aR$^{+/+}$ mice. GFAP-C3a mice did not differ from their WT littermates in the density of synapsin I$^+$ puncta in any of the cortical regions assessed (FIG. 1C).

The average size of synapsin I$^+$ puncta in the deeper layers of the ipsilesional secondary motor cortex was significantly smaller in C3aR$^{-/-}$ mice compared with C3aR$^{+/+}$ mice (P=0.014). The differences between C3aR$^{-/-}$ and C3aR$^{+/+}$ mice in synapsin I expression in the contralesional hemisphere appear to be induced by brain ischemia, since the density and size of synapsin I$^+$ puncta did not differ between genotypes in age-matched naïve mice. The markedly lower density and size of synapsin I$^+$ puncta in naïve compared with injured mice point to active involvement of the contralesional hemisphere in stroke-induced synaptic remodelling.

Figure 2:
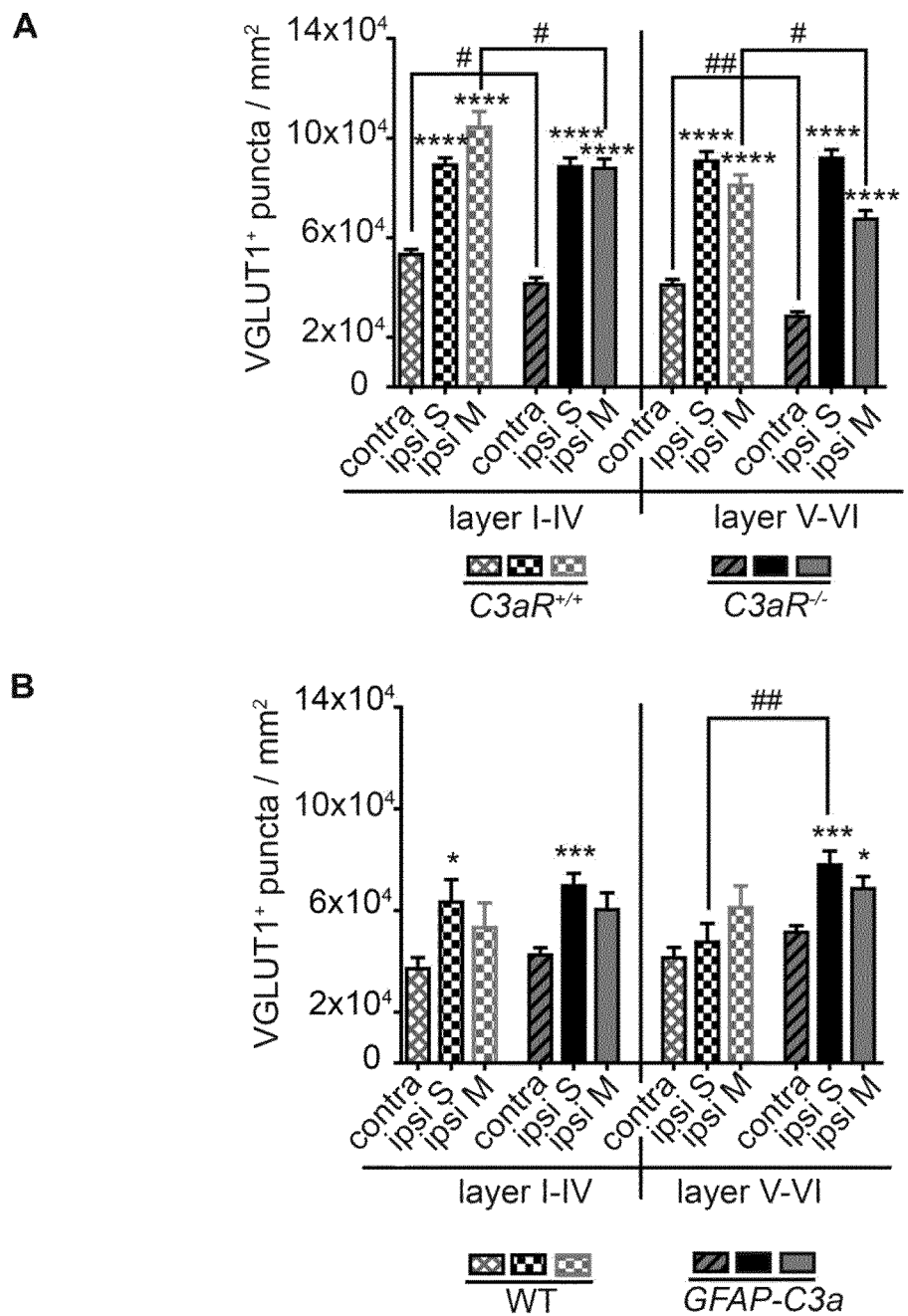
FIG. 2 shows that signalling through C3aR stimulates an increase in the density of glutamatergic synapses in the peri-infarct region. (A, B) Density of VGLUT1+ puncta in the proximal peri-infarct and contralesional cortex (mean±SEM; C3aR$^{+/+}$ n=6, C3aR$^{-/-}$ n=6, WT n=6, GFAP-C3a n=7). One-way ANOVA with Sidak's planned comparisons: *P<0.05, *P<0.001, **P<0.0001 for ipsi vs. contra comparisons; #P<0.05, ##P<0.01 for between-genotype comparisons. contra—contralesional cortex; ipsi M—ipsilesional motor cortex; ipsi S—ipsilesional somatosensory cortex

Next, the inventors used antibodies against VGLUT1 that have been shown to visualize the majority of glutamatergic synapses and approximately 75% of all synapsin I positive synapses in the cortex (Micheva et al., 2010). The inventors found that the density of VGLUT1$^+$ puncta was increased in the infarct-proximal region of both C3aR$^{+/+}$ and C3aR$^{-/-}$ mice; the density of VGLUT1$^+$ puncta was lower in the contralesional and motor cortex of C3aR$^{-/-}$ mice (P<0.05; FIG. 2A). In the GFAP-C3a but not WT mice, the density of VGLUT1$^+$ puncta in the deep layers of the ipsilesional cortex was higher compared with the contralesional hemisphere. In the somatosensory cortex, the density of VGLUT1$^+$ puncta was higher in GFAP-C3a mice compared with WT mice (P=0.002; FIG. 2B). In the superficial layers of the ipsilesional somatosensory cortex, the density of VGLUT1$^+$ puncta was increased in both WT and GFAP-C3a mice (P=0.022 and P=0.0006, respectively; FIG. 2B). Although the VGLUT1$^+$ puncta were larger in the ipsilesional compared to contralesional cortex in both C3aR$^{+/+}$ and C3aR$^{-/-}$ mice, C3aR$^{-/-}$ mice had smaller VGLUT1$^+$ puncta in the deep layers of the ipsilesional motor cortex (P=0.01). In both layers of the ipsilesional somatosensory cortex in GFAP-C3a mice, VGLUT1$^+$ puncta were larger compared with WT mice (P<0.05).

Taken together, these data suggest that C3aR is important for the post-stroke increase in the number of pre-synaptic glutamatergic terminals, and possibly synapses, and this response is cortical region and layer specific.

Figure 3:
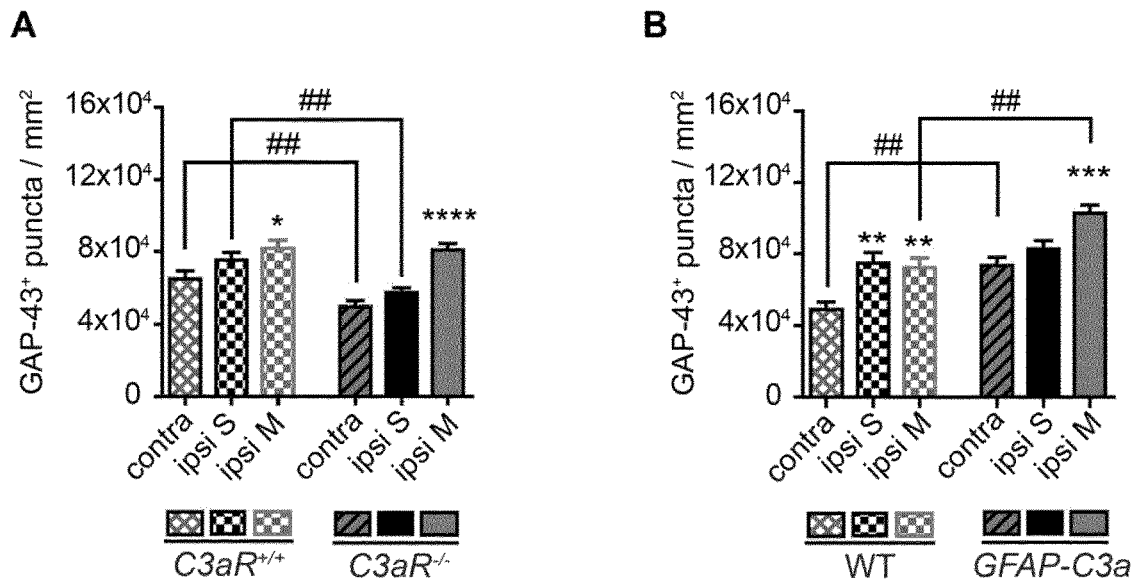
FIG. 3 shows that signalling through C3aR stimulates post-stroke GAP-43 expression in the cortex. (A, B) Density of GAP-43+ puncta in the proximal peri-infarct and contralesional cortex (mean±SEM; C3aR$^{+/+}$ n=10, C3aR$^{-/-}$ n=14, WT n=13, GFAP-C3a n=12). One-way ANOVA with Sidak's planned comparisons: *P<0.05, P<0.01, *P<0.001, **P<0.0001 for ipsi vs. contra comparisons; #P<0.05, ##P<0.01 for between-genotype comparisons. contra—contralesional cortex; ipsi M—ipsilesional motor cortex; ipsi S—ipsilesional somatosensory cortex

Signalling through C3aR Positively Regulates the Expression of GAP-43, a Marker of Axonal, Pre-Synaptic and Glial Plasticity To assess the effects of C3a and C3aR signalling on axonal plasticity, brain sections were stained with antibodies against GAP-43, one of the major phosphoproteins in the neuronal growth cone that is involved in neurite extension. GAP-43 is considered a surrogate marker of axonal plasticity (Benowitz and Routtenberg, 1997) but can also regulate neurotransmitter release (Dekker et al., 1991) and mediate glial plasticity during astrogliosis (Hung et al., 2016). The inventor's data demonstrate that GAP-43 in the peri-infarct cortex is predominantly localized in the neuronal compartment (approximately 60% overlap with β3-tubulin) and in the direct vicinity of pre-synaptic terminals (approximately 70% overlap with synaptophysin), and to a lesser degree in astrocytes (22% overlap with S100beta and 48% overlap with GFAP). Regardless of genotype, the inventors observed increased density (20% to 70% increase, P<0.05 to P<0.0001) and size (10% to 25% increase, P<0.01 to P<0.0001) of GAP-43$^+$ puncta in the injured compared with the contralesional hemisphere (FIG. 3). Further, the inventors found that C3aR$^{-/-}$ mice had 20% to 25% fewer GAP-43$^+$ puncta in the proximal ipsilesional somatosensory cortex as well as in the contralesional cortical region compared with C3aR$^{+/+}$ mice (P=0.006 and P=0.030, respectively, FIG. 3A). Conversely, GFAP-C3a mice had higher density of GAP-43$^+$ puncta in the peri-infarct motor (33% increase, P=0.0002) and contralesional cortex (50% increase, P=0.003) than their WT littermates (FIG. 3B). GAP-43$^+$ puncta in these regions were also moderately larger in GFAP-C3a than in WT mice (P=0.013 and P=0.021 in the ipsi- and contralesional cortex, respectively). Similar differences were observed in the distal peri-infarct regions. Taken together, these findings indicate that C3a signalling through C3aR stimulates axonal, pre-synaptic, and glial plasticity after focal ischemic brain injury in both hemispheres.

Intranasal C3a Treatment Improves Functional Recovery in WT Mice

To determine the therapeutic potential of C3a in a clinically relevant scenario, the inventors next investigated whether delayed treatment with C3a affects functional recovery and neural plasticity processes in WT mice.

Intranasal administration allows for repeated, rapid, and non-invasive delivery of peptides to the brain. Since the transfer of molecules occurs mainly via peri-vascular bulk flow along olfactory and trigeminal nerves, this method does not rely on crossing the blood-brain barrier and allows peptides to reach cerebrospinal fluid within minutes (Lochhead and Thorne, 2012). As C3aR activation is known to cause histamine release from basophiles and mast cells in a similar way as stimulation by IgE, the inventors monitored body temperature change to verify that intranasal administration of C3a peptide does not cause systemic hypersensitivity or anaphylaxis (Kind, 1955). The transient (5-10 min) and very small drop in body temperature observed after administration of C3a or PBS is consistent with a general response to intranasal administration of a non-sensitizing agent (Fang et al., 2013) and indicates the absence of an adverse systemic response to C3a.

Figure 4:
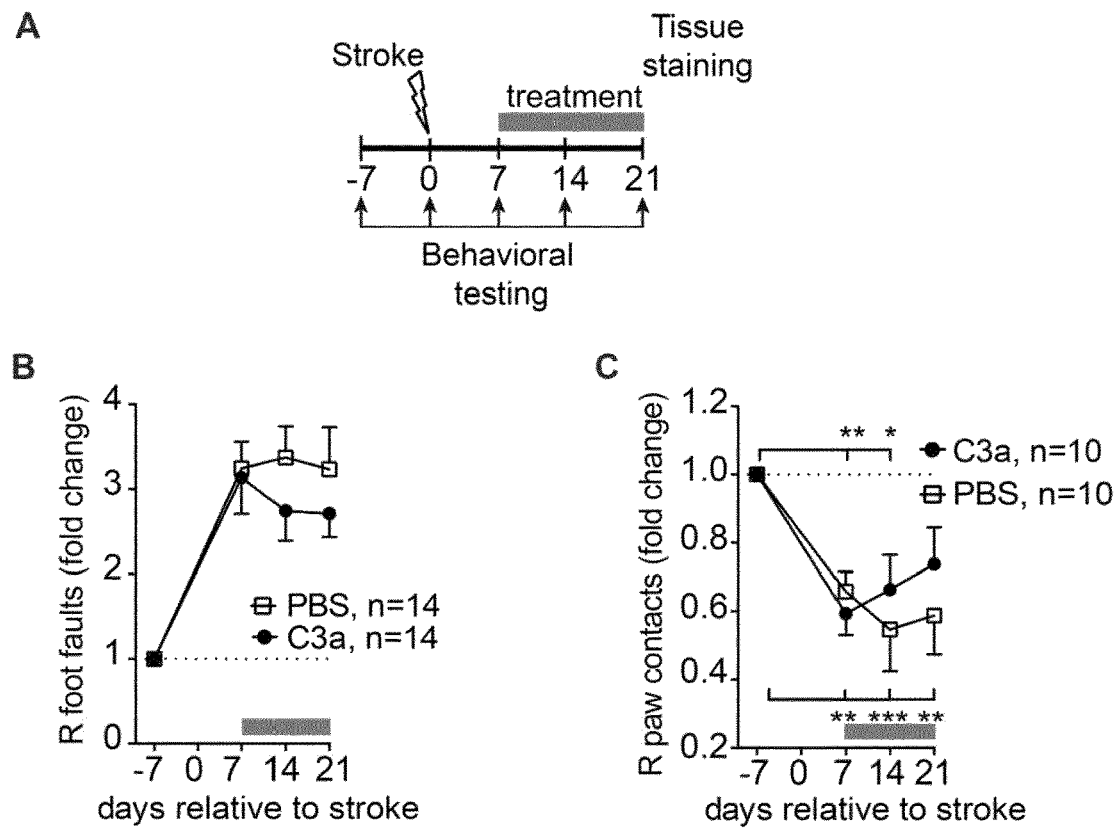
FIG. 4 shows that intranasal C3a stimulates recovery of forepaw function after stroke. (A) Study design. (B) Fold change relative to baseline performance in right (R, affected) paw foot faults over time in the grid walking task. (C) Fold change relative to baseline performance in R forepaw usage while rearing in the cylinder test over time (4 mice/group excluded). Gray bar indicates treatment period. Mean±SEM. P<0.01, ***P<0.001 post-stroke vs. baseline performance of C3a treated mice; § P<0.05, §§ P<0.01 §§§ P<0.001 post-stroke vs. baseline performance of PBS treated mice; determined by two-way ANOVA repeated measures and Dunnett's test for within-group comparisons.

Using fluorescently labelled C3a and epifluorescent imaging in live animals, the inventors first confirmed that C3a can be delivered to the mouse brain through intranasal administration and can be subsequently detected in the brain tissue for at least 3 hours. As the neural plasticity responses in GFAP-C3a mice appeared to be more pronounced in motor regions than in sensory processing regions, WT mice were subjected to photothrombotic stroke in the motor cortex, leading to substantial impairment of the forepaw function, and treated daily with C3a between days 7 and 21 post-stroke (FIG. 4A). Intranasal C3a treatment had no effect on infarct volume (P=0.429). In the grid walking task, C3a-treated mice showed a tendency toward reduced number of right paw foot faults on days 14 and 21 compared with day 7 (P=0.0545 and P=0.0839 for days 14 and 21, respectively, Dunnett's test), whereas no trend toward significant improvement was observed in PBS-treated mice (P=0.147 and P=0.486 on days 14 and 21, respectively, FIG. 4B). At all time points after stroke, both groups showed significant impairment with respect to the baseline performance (P<0.001). In the cylinder test, C3a-treated mice showed continuous improvement between days 7 and 21 such that on day 21 their frequency of right paw use for body support did not differ from baseline performance (P=0.062, FIG. 4C). The PBS-treated mice showed sustained impairment until the end of the testing period (P=0.001 day 21 versus baseline; n=10 mice/group). These results show that intranasal C3a treatment can promote the recovery of forepaw function after ischemic stroke.

Intranasal C3a Stimulates Neural Plasticity in the Peri-Infarct Cortex

Figure 5:
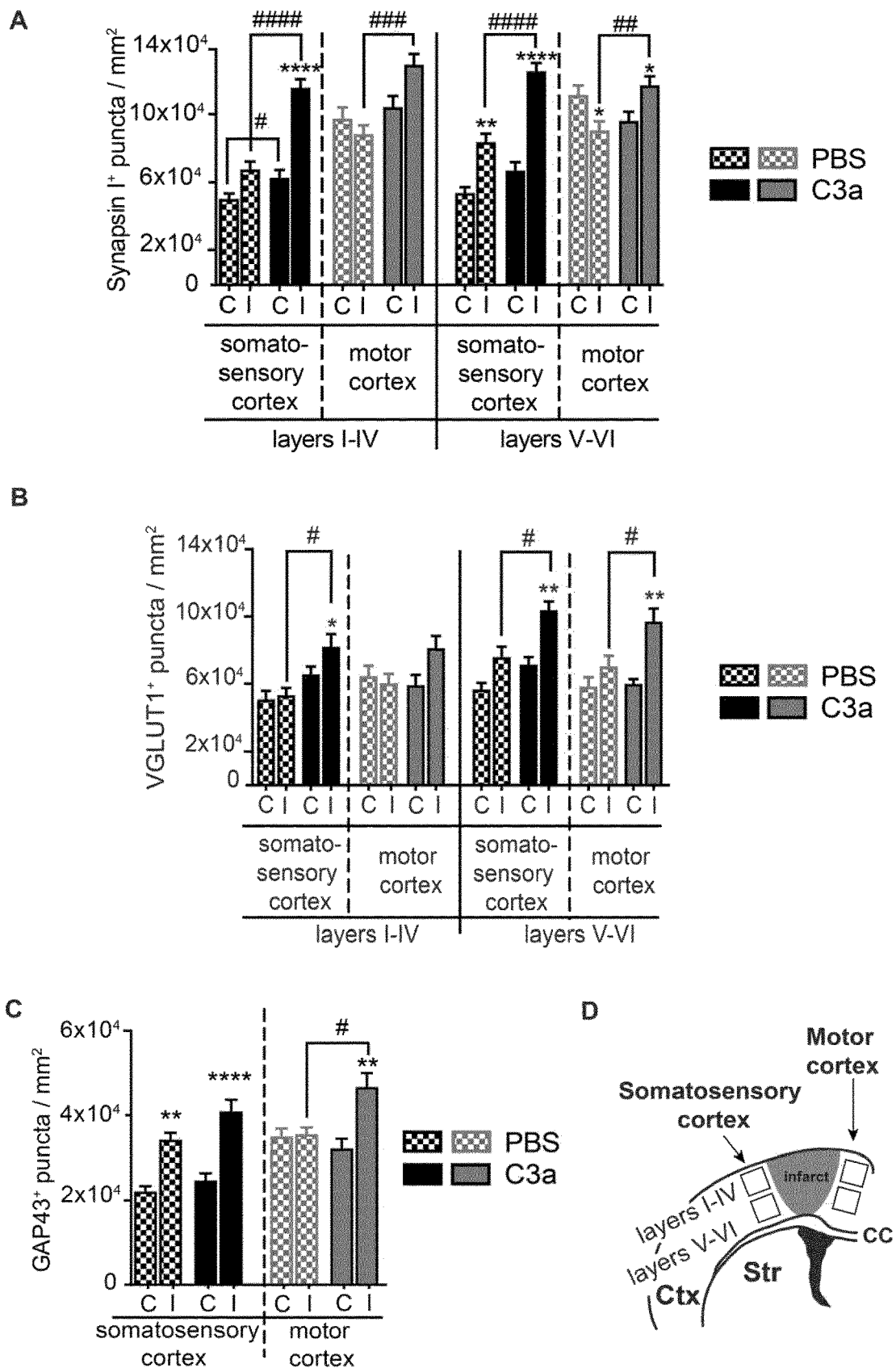
FIG. 5 shows that intranasal C3a increases synaptic density and GAP-43 expression in the ipsilesional cortex 21 days after stroke. (A) Quantification of synapsin I+ puncta. (B) Quantification of VGLUT1+ puncta. Mean±SEM; n=7 mice/treatment group. (C) Quantification of GAP-43+ puncta. Mean±SEM; n=14 mice/treatment group. (D) Schematic diagram indicating cortical regions chosen for analysis. One-way ANOVA with Sidak's planned comparisons: *P<0.05, P<0.01, **P<0.0001 for ipsilesional vs. contralesional hemisphere comparisons; #P<0.05, ##P<0.01, ###P<0.001, ####P<0.0001 for between-treatment comparisons. C—contralesional cortex; I—ipsilesional cortex

To investigate whether functional improvement in C3a-treated mice was due to increased neural plasticity, the inventors quantified the expression of synapsin I, VGLUT1 and GAP-43 in the cortex. The C3a-treated mice had (depending on the cortical depth) a 20% to 40% (in the ipsilesional motor cortex; P<0.001) and a 60% to 70% (in the ipsilesional somatosensory cortex; P>0.0001) higher density of synapsin I$^+$ puncta compared with PBS-treated mice (FIG. 5A). Synapsin I$^+$ puncta in the ipsilesional motor cortex were also larger (by 9.7%, P=0.0004 and 8.1%, P<0.0001 in the superficial and deep layers of cortex, respectively) in C3a-compared with PBS-treated mice. C3a treatment was associated with 20% increase in density of synapsin I$^+$ puncta in the contralesional somatosensory cortex (P=0.030, FIG. 5A). Similar to synapsin I, quantification of VGLUT1 expression showed a higher density and size of VGLUT1$^+$ puncta in the ipsilesional cortex of C3a treated mice, in particular in the deep cortical layers (FIG. 5B). The inventors observed a robust correlation between the density of synapsin I$^+$ and VGLUT1$^+$ puncta (R=0.768, P=0.0007 for somatosensory cortex; R=0.803, P=0.0005 for motor cortex) within pooled treatment groups. Importantly, the density of synapsin puncta in the deep layers of peri-infarct cortex was associated with functional recovery between days 7 and 21 post stroke (R$^2$=0.405, P$_{slope}$=0.0025 for motor cortex and change in impaired paw usage in cylinder test (R$^2$=0.155, P$_{slope}$=0.042 for somatosensory cortex and change in foot faults during grid walking). The size of synapsin puncta in peri-lesional motor cortex was associated with an improvement in right forepaw usage during the cylinder test (linear regression: R$^2$=0.247, P$_{slope}$=0.026). The association between the size of synapsin I$^+$ puncta in the somatosensory peri-infarct cortex and performance in grid walking task did not reach statistical significance (R$^2$=0.134, P$_{slope}$=0.050).

Motor cortex lesion led also to as much as a 75% increase in the density of GAP-43$^+$ puncta in the ipsilesional vs. contralesional somatosensory cortex (P<0.01, FIG. 5C). C3a-treated mice showed about a 50% increase in the density of GAP-43$^+$ puncta in the ipsilesional motor cortex compared with the corresponding contralesional region (P=0.012), and compared with the ipsilesional cortex of PBS-treated mice (P=0.015, FIG. 5C). The average size of GAP-43$^+$ puncta did not differ between the experimental groups. Jointly, these findings indicate that intranasal C3a treatment starting 7 days after stroke stimulates functional recovery in the relatively early phase after experimental stroke by increasing axonal and glial plasticity and the formation of new pre-synaptic terminals in the peri-infarct cortex.

Intranasal C3a Leads to a Faster and Sustained Functional Recovery

Figure 6:
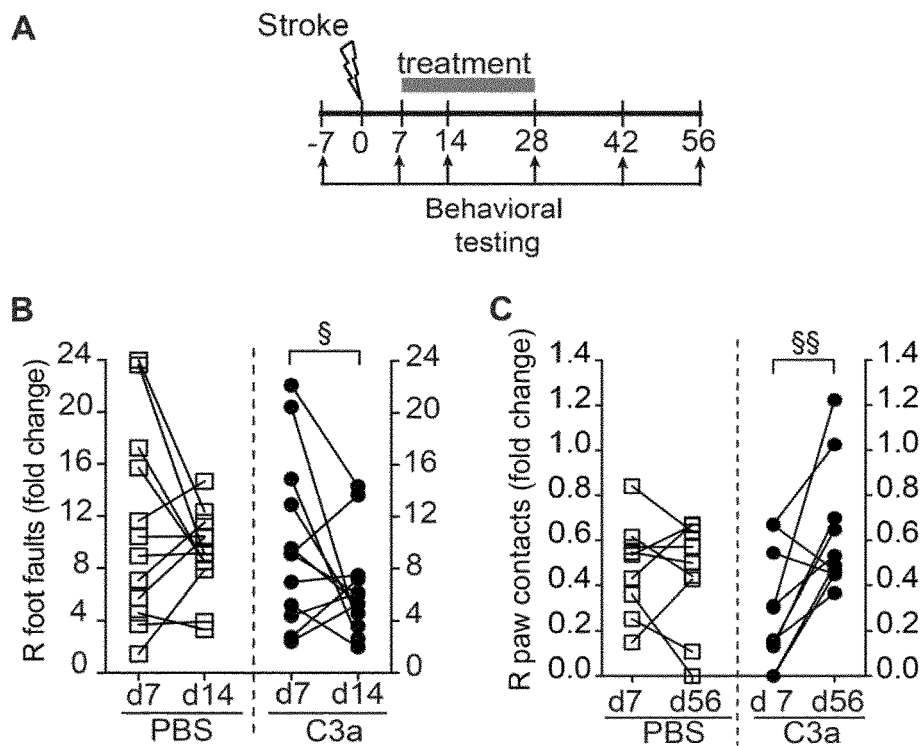
FIG. 6 shows that intranasal C3a leads to faster and sustained recovery of forepaw function. (A) Study design. (B) Grid walking task, change in the performance of individual mice in between days 7 and 14 after stroke. § P<0.05, Wilcoxon signed rank test. (C) Cylinder test, change in the performance of individual mice between days 7 and 56 post-stroke. §§ P<0.01, paired t-test.

Because neither of the treatment groups showed full recovery in terms of forepaw motor function as assessed by the grid walking task by 21 days post-stroke, the inventors next asked whether longer intranasal C3a exposure could provide greater benefit for functional recovery and whether functional improvement would be sustained after cessation of the treatment. Starting on day 7 after motor cortex stroke induction, mice were treated with C3a or PBS for 3 weeks and behavioural performance was assessed until day 56 post-stroke (FIG. 6A). In the grid walking task, both groups displayed a substantial degree of recovery over the two-month period. However, the extent and time course of functional recovery were markedly different between the groups. C3a-treated mice showed significantly fewer right foot faults compared with PBS-treated mice at days 14 (P=0.0097) and 56 post-stroke (P=0.047, Mann-Whitney U test). C3a-treated mice also had a significant reduction in foot faults within the first week of the treatment (day 14 vs. day 7 post-stroke, P=0.041, as determined by Dunn's test; or by Wilcoxon test P=0.039; FIG. 6B), while control mice did not show significant improvement until day 28 post-stroke (Dunn's test: P=0.98 or Wilcoxon test: P=0.31, FIG. 6B, for day 14 and P<0.001 for day 28 post stroke, as determined by Dunn's test). The functional improvement of C3a-treated mice continued after the conclusion of the treatment period and by the final day of testing their performance did not differ from pre-stroke baseline levels (baseline vs. day 56 post-stroke, Dunn's test: P=0.103). Performance of PBS-treated mice plateaued at day 42 post-stroke and did not reach baseline levels by day 56 post-stroke (Dunn's test: P=0.0113).

A similar positive effect of C3a treatment on post-stroke functional recovery was observed in the cylinder task. The average scores on the last day of testing showed only a trend toward a difference between groups (Sidak's test: P=0.0687), although the C3a-treated mice displayed a sustained functional improvement compared with day 7 at days 28 and 56 post-stroke (Dunnett's test: P=0.032 and P=0.0019, respectively) while changes in performance of PBS-treated mice were inconsistent and not statistically significant (Dunnett's test: P=0.982 for day 56). Also, paired analysis of individual mice showed that C3a-treated animals readily increased their affected paw usage between the treatment initiation and 4 weeks after the completion of the treatment period (paired t-test: P=0.009; 8/10 of mice improved), while in PBS-treated mice, overall right paw impairment did not change (paired t-test: P=0.673; only 3/9 of mice improved, FIG. 6C). Taken together, these data indicate that intranasal treatment with C3a supports faster and more complete motor function recovery, which is sustained beyond the treatment period.

Discussion

In the present study, the inventors evaluated the role of C3a and C3aR signalling in stroke-induced neural plasticity. The inventors found that C3a overexpression in reactive astrocytes increased, whereas C3aR deficiency decreased expression of GAP-43, a marker of post-stroke axonal, synaptic, and glial plasticity, without affecting the infarct size. Moreover, C3aR deficiency was associated with reduced expression of synapsin I, a structural element of pre-synaptic terminals and a marker of synaptic plasticity, as well as VGLUT1, a pre-synaptic marker of the majority of glutamatergic synapses (Micheva et al., 2010). Intranasal treatment with C3a starting 7 days post-stroke robustly upregulated the expression of neural plasticity markers and was associated with faster and sustained functional recovery in WT mice.

The inventors have previously shown that C3-deficient mice had increased infarct volume at 7 and 21 days after permanent middle cerebral artery occlusion (MCAO) (Rahpeymai et al., 2006) and that GFAP-C3a mice were strongly protected from neonatal hypoxic ischemic brain injury (Järlestedt et al., 2013). To study the role of C3a and C3aR in stroke-induced neural plasticity and functional recovery, the inventors used the photothrombotic stroke model, which results in an irreversibly damaged ischemic core in the targeted cortical region and a relatively narrow penumbra with limited possibilities of collateral blood flow. Consequently, this model offers high reproducibility of stroke location with a small infarct size, facilitating study of regeneration processes while evoking a similar early cellular response as the permanent MCAO model (Jander et al., 1995; Schroeter et al., 1994). The inventor's findings that the infarct volume was not affected by the overexpression of C3a or the absence of C3aR are therefore not surprising and do not preclude a possible role of C3a and C3aR in neuroprotection or ischemia-induced tissue injury.

Synaptic plasticity and functional remapping involving both the peri-infarct regions and the contralesional hemisphere are believed to play a critical role in the recovery of function after stroke (reviewed in Pekna et al., 2012). Axonal plasticity is a hallmark of regenerative plasticity and a mechanism that ultimately leads to the emergence of new synapses after an ischemic insult. This phenomenon is associated with reactivation of the intrinsic neuronal growth program and robust upregulation in the peri-infarct cortex of the membrane phosphoprotein GAP-43 (Carmichael et al., 2005), which associates with axonal growth cones and is used as marker of axonal sprouting (Benowitz et al., 1990; Benowitz and Routtenberg, 1997). GAP-43 is also upregulated during reactive synaptogenesis (Benowitz et al., 1990; Lin et al., 1992) and involved in pre-synaptic plasticity through regulation of vesicle trafficking (Hou and Dahlström, 2000) and neurotransmitter release (Dekker et al., 1991). Recently, astrocytic GAP-43 was shown to mediate glial plasticity during astrogliosis, attenuate microglial activation, and provide beneficial effects for neuronal survival and plasticity (Hung et al., 2016).

The inventor's findings that the expression of GAP-43 is reduced in the absence of C3aR and increased when C3a is expressed in reactive astrocytes or administered intranasally, together with previous results showing that C3 is upregulated in sprouting neurons isolated from rat cortex after ischemic stroke (Li et al., 2010), and that there is a stimulatory effect of C3a on neurite outgrowth in vitro (Shinjyo et al., 2009) support the conclusion that C3a signalling through C3aR plays a positive role in post-stroke neural plasticity, possibly including axonal sprouting.

While many growth-related genes, including GAP-43, are induced shortly after ischemia and expressed for at least 28 days in young adult (2-month-old) mice, GAP-43 expression in aged (20-month-old) mice peaks only transiently around at 3 and 14 days post-stroke (Li and Carmichael, 2006). The inventor's findings of a robust increase in C3a-associated GAP-43 expression in the ipsilesional motor cortex in up to 9-month-old GFAP-C3a mice 21 days post-stroke indicate that C3a signalling extends the plasticity window and makes the post-stroke brain milieu more permissive for functional recovery.

The inventors further observed a robust and to some extent cortical region- and layer-specific ischemia-induced increase in the density of glutamatergic synapses. This is in contrast to previous reports focusing on the first month after stroke that found a cortical layer-specific and transient effect of stroke on the density of GABAergic synapses (Hiu et al., 2016) or an early reduction in the density of pre-synaptic terminals followed by gradual recovery of baseline levels one month after stroke (Liauw et al., 2008). These differences between studies are conceivably due to differences in stroke models and quantification methods used. Together with reports of the association between synaptic density and better recovery of function after ischemic stroke (Chen et al., 2007; Cui et al., 2013; Cui et al., 2010; Liauw et al., 2008), the inventor's findings of improved recovery, increased expression of synapsin I and VGLUT1 in C3a treated mice, and association between synapsin I expression and functional improvement point to increased synaptic density as an important contributor to functional recovery.

Another important finding of the inventor's study is the positive effect of C3a-C3aR signalling on synaptic density in the peri-infarct region. Neuronal C3aR is a part of a signalling pathway that results in increased synaptic strength, and treatment with a C3aR antagonist or C3aR deficiency in neurons co-cultured with WT astrocytes reduced dendritic complexity (Lian et al., 2015). However, excessive activation of neuronal C3aR alters dendritic morphology and synaptic function (Lian et al., 2015) and in the context of neurotropic viral infection, C3aR is required for the removal of pre-synaptic terminals by an unidentified mechanism involving microglia (Vasek et al., 2016). The net effect of C3aR activation in the CNS thus appears to depend on the context and on the extent of C3aR activation. The timing of interventions targeting C3aR may therefore need to be carefully optimized.

In light of the role of neuronal C3aR in modulation of synaptic strength and dendritic morphology (Lian et al., 2015), the C3a-C3aR-mediated upregulation of expression of GAP-43 and increased number of pre-synaptic terminals, particularly glutamatergic terminals, observed in the inventor's study is conceivably due at least in part to a direct effect of C3a on neurons. However, given that C3aR is also expressed on glial, endothelial, stem, and immune cells, C3a can also exert its effects on post-stroke plasticity indirectly by modulating the functions of these cell types.

As the contralesional hemisphere becomes electrically activated after stroke (Calautti and Baron, 2003; Dijkhuizen et al., 2001), can be a source of transcallosal axonal sprouting (Carmichael and Chesselet, 2002), and shows evidence of synaptic plasticity, it cannot be regarded as a control region for neural plasticity studies. Increased turnover of mushroom-like dendritic spines and synapse number in contralesional somatosensory cortex was associated with establishing a new pattern of electrical circuit activity in the intact hemisphere and functional recovery (Luke et al., 2004; Takatsuru et al., 2009). Moreover, dendritic remodeling in the cortex contralesional to injury is characterized by the presence of enhanced-efficacy perforated and multiple synaptic bouton-containing synapses (Jones, 1999; Luke et al., 2004), both of which are morphologically larger than regular synapses (Ganeshina et al., 2004; Toni et al., 1999). Here, the inventors found that $C3aR^{-/-}$ mice had a standard number of synapsin $I^+$ as well as $VGLUT1^+$ pre-synaptic terminals, and intranasal C3a treatment increased the density of synapsin I⁺ terminals in the contralesional cortex. Together with smaller average size of synapsin I⁺ and VGLUT1⁺ puncta in the peri-infarct motor cortex of C3aR$^{-/-}$ mice, the inventor's findings suggest that C3aR signalling may be important for long-distance synaptic plasticity after stroke. Importantly, the inventors show that the differences in synaptogenic response observed in the contralesional hemisphere are not due to baseline differences between C3aR$^{-/-}$ and C3aR$^{+/+}$ mice.

Increased synaptogenesis and axonal plasticity provide greater potential for new axono-dendritic connections for neuronal communication and post-stroke circuit rewiring. However, beneficial effects on outcome need to be verified at the functional level. Since upregulation of GFAP expression in peri-infarct astrocytes starts within 24 h, peaks around 4 days, and persists for at least 2 months after photothrombotic stroke (Nowicka et al., 2008), a similar temporal pattern would be expected for C3a expression in GFAP-C3a mice. The inventors reasoned that high acute C3a levels produced by reactive astrocytes might not provide an optimal milieu for regeneration. Therefore, to assess the role of C3a on functional recovery and focus on its post-acute effects, the inventors used a pharmacological approach and treated WT mice with intranasal C3a starting 7 days after stroke. This C3a treatment, which avoids the potentially deleterious effects of C3a in the acute phase, was associated with increased synaptogenesis and GAP-43 expression as well as better recovery of forepaw function. The positive effect of intranasal C3a on functional recovery was sustained even after treatment cessation. It is noteworthy that intranasal treatment in mice requires repeated restraint, which can be regarded as predictable chronic mild stress. This, however, would not be an issue in human patients. Given the profound negative effect of stress on functional recovery from stroke (Walker et al., 2014), the efficacy of intranasal C3a treatment could be underestimated in a mouse model. In light of its anaphylatoxic properties, it is important to note that the inventors did not observe any adverse or systemic effects of intranasal C3a, even after repeated administration. These results show that delayed intranasal treatment with C3aR agonists is an attractive approach to improve functional recovery after ischemic brain injury.

Conclusion

C3a-C3aR signalling stimulates post-stroke synaptogenesis and axonal plasticity, and intranasal C3a treatment in the post-acute phase after ischemic stroke improves functional recovery. These findings open new avenues for translational research aiming to promote neural plasticity and recovery after brain injury.

Examples—Set 2

Materials and Methods

Animals

Subjects were male C57BL6/CNr mice (Charles River Laboratories, Sultzfield, Germany) and C3a receptor deficient (C3aR$^{-/-}$) mice (Kildsgaard et al., 2000) backcrossed to C57BL6/J mice (Jackson Laboratories, Bar Harbor, Me., USA) for 10 generations. The local Animal Ethics Committee in Gothenburg (308-2012; 41-2015) approved all animal experiments and mice were housed at Experimental Biomedicine (EBM), Sahlgrenska Academy, University of Gothenburg. Mice were kept under standard conditions of temperature (20° C.), and relative humidity (45%) and on an artificial light-dark cycle of 12 h (lights on at 06:00). Food and water were available ad libitum.

Experimental Design

Two studies differing in treatment duration and behavioural tests used were performed.

Figure 7:
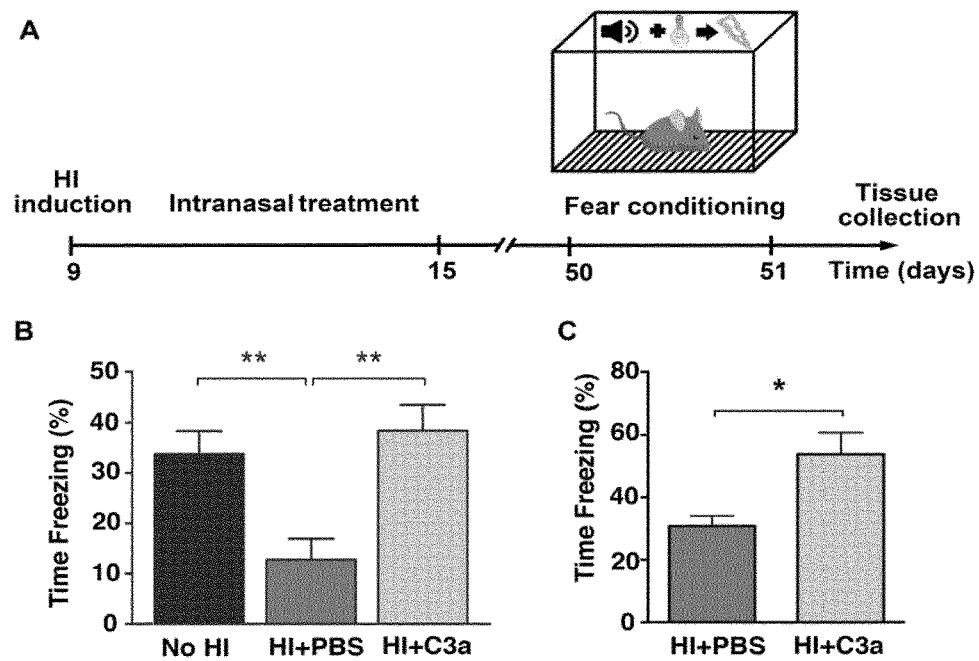
FIG. 7 shows that intranasal C3a treatment for 7 days ameliorates hypoxia-ischemia induced cognitive impairment similar to single dose intracerebroventricular injection of C3a. (A) Schematics of study design. At P9, mice were subjected to hypoxia-ischemia and (B) treated intranasally with PBS or C3a for 7 days (n=5-8 per group) or (C) treaded by a single intracerebroventricular injection of C3a ((n=17-18 per group), Järlestedt et al, 2013) Memory was assessed by cue-induced fear conditioning (percent freezing time 24 h after training). Mean±SEM. HI, hypoxic-ischemic injury. *p<0.05 by unpaired t test.

In the long-term study (7 days of intranasal treatment), 2 groups of wild-type (WT) and C3aR$^{-/-}$ mice subjected to neonatal HI injury and treated with either C3a or PBS were used; WT HI-C3a (n=5), WT HI-PBS (n=8), C3aR$^{-/-}$ HI-C3a (n=7), C3aR$^{-/-}$ HI-PBS (n=8). These mice were tested in a cue-induced fear conditioning test at P50 and brains were collected at P51 (FIG. 7A).

Figure 8:
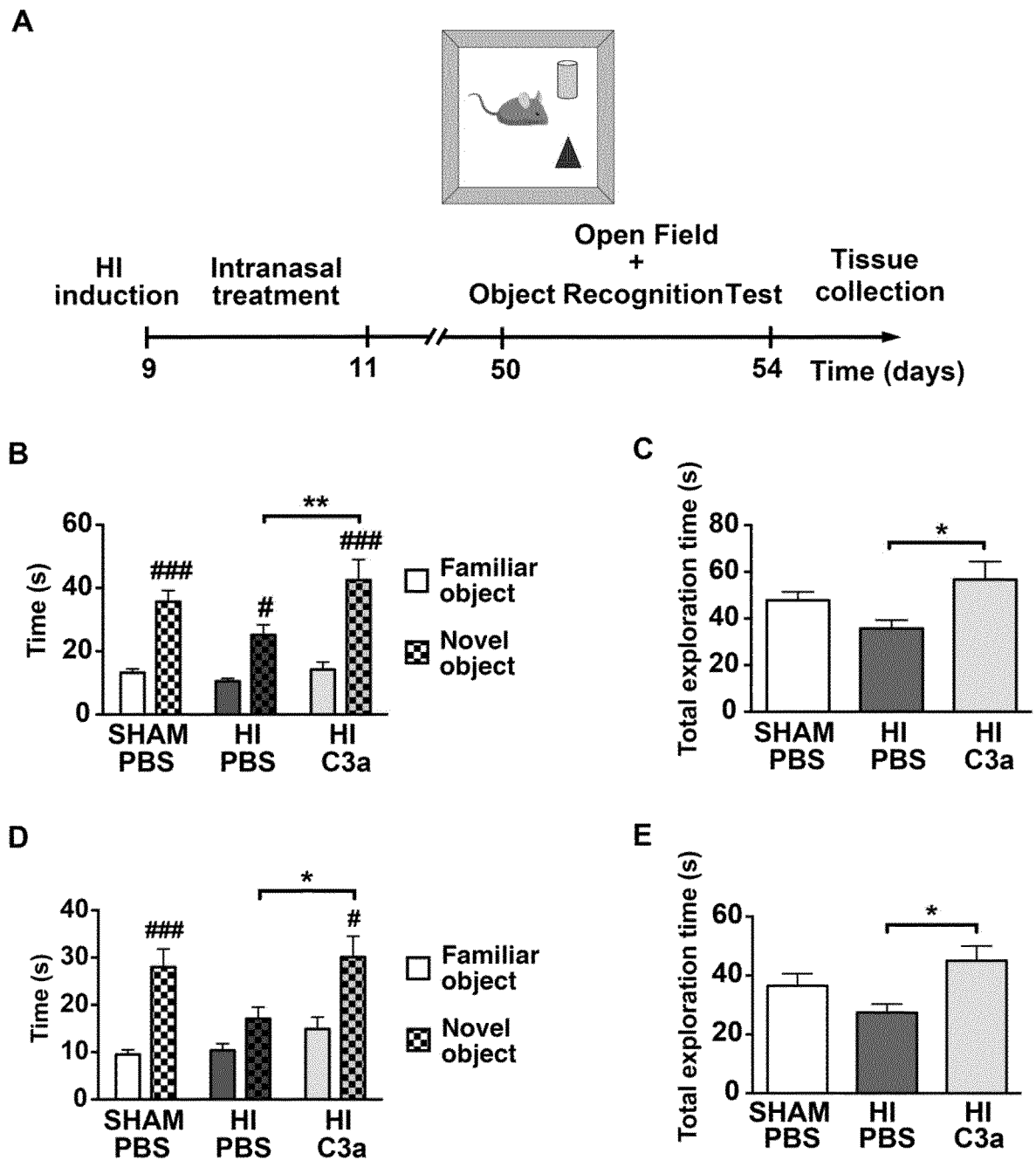
FIG. 8 shows that three-day long intranasal C3a treatment ameliorates hypoxia-ischemia induced cognitive impairment. (A) Schematics of study design. At P9, mice were subjected to sham procedure or hypoxia-ischemia followed by intranasal treatment with PBS or C3a for 3 days. Locomotive behaviour and memory were assessed by object recognition test. Time spent exploring individual objects and total exploration time during short-term memory testing 6 h later (B, C), and long-term-memory testing 24 h later (D, E). n=8-11 per group; mean±SEM. HI, hypoxic-ischemic injury. #p<0.05, ###p<0.001 novel vs. familiar object; *p<0.05, **p<0.01 C3a vs. PBS. Statistics used were two-way ANOVA and one-way ANOVA for evaluating the time spent exploring individual objects and total exploration time, respectively, followed by a Tukey's multiple comparisons post-hoc test.

In the short-term study (3 days of intranasal treatment), 3 groups of WT mice were used; animals subjected to neonatal HI injury and treated with either C3a (HI-C3a, n=18) or PBS (HI-PBS, n=18) and sham-operated animals treated with PBS (SHAM-PBS, n=19). These mice were tested in an open field and object recognition test (ORT) at P50-P54 and brains were collected at P55 (FIG. 8A).

HI Injury Induction

Neonatal HI injury was induced on postnatal day 9 (P9), as previously described with modifications for mice (Hedtjärn et al., 2002; Rice et al., 1981; Sheldon et al., 1998). Mice were anesthetized with 3.5% isoflurane (Baxter Medical, Kista, Sweden) for induction and 1.5% thereafter, in 1:1 oxygen and nitrous oxide. The left common carotid artery was dissected and permanently ligated with a prolene suture (6.0). The incision was closed and infiltrated with lidocaine (Xylocain®, Astra Zeneca, Gothenburg, Sweden). Mice were returned to the dam for 1 hour and then placed in a chamber with humidified air at 36° C. for 10 min, then exposed to humidified 10% oxygen in nitrogen for 30 min at 36° C., and then kept in humidified air at 36° C. for 10 min before being returned to the dam. Sham animals were subjected to an incision in the neck on P9. These pups were also removed from the dam for the time duration that injured animals stayed in the chamber, but remained instead in a warming tray at 36° C. under normal oxygen conditions. At postnatal day 21 (P21) mice were weaned and group housed with same sex littermates.

Intranasal C3a Administration

Purified human C3a (Complement Technology Inc., Tyler, Tex., USA) was diluted in sterile phosphate buffered saline (PBS) to a concentration of 200 nM, and a total of 8 µl i.e. 1.6 µmol (4 µl/nostril; corresponding to ca. 2.56 µg/kg body weight) of peptide solution or PBS was given intranasally to awake and hand-restrained mice held in a supine position. Solutions were administered through a pipette tip, drop-wise in 2 µl-portions divided by 1 min intervals to allow for absorption. This method of administration to one nostril at a time does not affect breathing. C3a or PBS was given every 24 hours for three (short-term study) or seven (long-term study) days starting 1 h after HI induction, i.e. between P9 and P11 or P9 and P15, respectively. Mice in each litter were randomly assigned to C3a or PBS treatment. Sham animals received PBS. The investigators carrying out behavioural studies and analysing data were blinded to treatment group.

Behavioural Analysis

Object Recognition Test

The object recognition test is based on the innate preference of mice to explore a novel object rather than a familiar one. Therefore, animals that remember the familiar object will spend more time exploring the novel object (Leger et al., 2013). From 3 days before starting the test, mice were daily handled for 2 min to minimize the possible stress due the researcher interaction. All experiments were performed at the same time of the day, between 9 am and 5 µm, and inside of a plastic box of 50×50×50 cm dimensions where the light intensity was dim and equal in all parts of the apparatus. Before being placed in the arena, mice had a 60 min habituation period in the behavioural room. Prior to the familiarization session, during which two identical objects were introduced, mice were habituated to the apparatus for 10 min during 3 consecutive days. Activity on the first habituation day was recorded as an open field test to assess locomotor and exploratory activities. During the familiarization session, two identical 250 ml bottles filled with shredded paper were placed at an equal distance from the arena walls (approximately 5 cm). Between mice, the apparatus and objects were cleaned with 50% ethanol to minimize olfactory cues. Animals were allowed to explore both objects for 10 min. A minimal exploration criterion of 20 s in total for both objects was used (Leger et al., 2013). Exploration was defined as directing the nose to the object at a distance <2 cm and/or touching the object with the nose or forepaws (Becerril-Ortega et al., 2014). Six hours after the familiarization session, intersession interval (ISI)=6 h, animals were tested for short-term memory (STM). This involved replacing one familiar object with a novel object (T75 culture flask filled with sand) placed in the same position. Long-term memory (LTM) was tested 24 h after the familiarization (ISI=24 h) by replacing the novel object used during the STM testing with another novel object (Lego tower). Animals were allowed to explore both objects for 10 min with a minimal exploration criterion of 20 s for both objects, during the SMT and LTM testing. Animals that did not reach the 20 s criterion were excluded from the experiment. Mice were tracked by Viewer3 video tracking system (Biobserve, Bonn, Germany), and the data were presented as time spent exploring individual objects and total exploration time(s).

Open Field

The activity of each animal on the first day of habituation to the object recognition test apparatus was recorded as an open field task to study locomotor and exploratory activities (Leke et al., 2012). Individual animals were placed in the square arena, and allowed to explore the apparatus for 10 min. The area was divided in 16 square zones, of which the four central squares (25% of the total area) were considered the central zone. The data were presented as average speed (cm/s), total activity (%), total locomotion time (s), total distance travelled (cm), distance travelled in the center (%), time spent in the center (%), number of rearing occurrences and number of grooming episodes.

Cue-Induced Fear Conditioning

Cue-induced fear conditioning with a shock-paired tone and light cue was performed on P49 and P50 as previously described (Järlestedt et al., 2011). On P49, mice were placed in an automatic reflex conditioning box (Ugo Basile, Comerio-Varese, Italy) adapted for fear conditioning. A tone and light cue were coupled to a programmed electrical stimulus to the floor bars, using an incorporated 8-pole circuit was coupled to a tone and light cue. Freezing behaviour, a defensive response to a perceived threat, was defined as a complete lack of movement and quantified by scoring freezing behaviour (on video footage) as present or absent once every 10 s for 2 min. Animals were then exposed to a paired tone (80 dB) and light (670 Hz) for a period of 20 s followed by a 2 s delay without any stimulus. After the delay, animals were exposed to a 2 s electrical stimulus (0.5 mA). Animals remained in the conditioning box for 30 s after the electrical stimulus to provide time for them to consolidate the association between the cue and the shock. On P50, animals were again placed in the conditioning box and freezing behaviour was measured for 2 min. Following this, the shock-paired tone and light were presented for 30 s and freezing behaviour was then measured again for 2 min. During the initial two-minute baseline test, mice were primarily engaged in exploratory behaviour, and freezing for all mice was zero or near zero regardless of genotype or treatment.

Brain Collection and Processing

On P51 (long-term study) or P55 (short-term study), mice were deeply anesthetized with thiopental [Pentothal Sodium (0.01 ml/g body weight), Hospira, Ill., USA)] and transcardially perfused with 0.9% saline, followed by 4% paraformaldehyde (PFA) in 0.1 M PBS. Brains were removed and post-fixed in 4% PFA at 4° C. for 24 h followed by 70% ethanol for 24 h. Tissue was processed using an automatic tissue processor (SAKURA Tissue Tek VIP 3000, Tournai, Belgium) and embedded in paraffin. Brains were cut at room temperature into 8-µm serial coronal sections using a sliding microtome (Microm HM 450, Thermo Scientific, Massachusetts, USA), attached to silane coated slides and dried at RT.

Histomorphologic Evaluation

For the histomorphologic evaluation, slides were incubated for 1 h at 65° C. and stained with haematoxylin and eosin. A wide-field microscope (Nikon Eclipse 80i; Nikon Instruments Inc., Tokyo, Japan) equipped with a color camera (Nikon DXM 1200F) was used to obtain images of brain sections 208 µm apart between −1.60 mm and −2.02 mm relative to Bregma; 3 sections/mouse. ImageJ 1.46r software was used to trace around the ipsilesional and contralesional hippocampus and hemisphere. Volumes were calculated according to the Cavalieri's principle, where $V=\Sigma A \times P \times T$ (Svedin et al., 2007) and hippocampus volume/hemisphere volume ratio was calculated for each hemisphere.

Immunohistochemistry

Neuronal nuclei (NeuN), growth associated protein 43 (GAP-43), synapsin I (SYN), vesicular glutamate transporter 1 (VGLUT1), Glial Fibrillary Acidic Protein (GFAP) and ionized calcium-binding adapter molecule 1 (Iba-1) were visualized in the cornu ammonis (CA) and dentate gyrus (DG) of the dorsal hippocampus by immunohistochemistry. Briefly, following heat-induced antigen retrieval with 0.01 M citrate buffer (pH 6, 0.05% Tween 20) for 3×5 min, sections were washed 3×5 min with PBS-T (0.05% Tween 20), non-specific protein binding was reduced by incubation with blocking buffer [4% normal donkey serum (NeuN and Iba-1), 1% bovine serum albumin (GAP-43 and SYN), 3% normal goat serum (VGLUT1), 2% bovine serum albumin (GFAP) in PBS-T] for 1 h at room temperature (RT). Tissue was then incubated with the primary antibody [anti-NeuN biotinylated (1:200, MAB 377B, Millipore, Mass., USA), anti-GAP-43 (1:1000, MAB347, Millipore, Mass., USA), anti-SYN (1:150, SC-7379, Santa Cruz, Calif., USA), anti-VGLUT1 (1:500, AB5905, Millipore, Mass., USA), anti-GFAP (1:200, Z0334, Dako, Stockholm, Sweden), anti-Iba-1 (1:500, 019-19741, Wako, Osaka, Japan)] in blocking buffer overnight at 4° C. One slide per staining batch was incubated only with blocking buffer without primary antibody and used as a negative control. Next, sections were washed 3×5 min with PBS-T and incubated with the secondary antibody [rabbit-anti mouse biotinylated Ig (1:200, GAP-43, E0354, Dako, Stockholm, Sweden), donkey-anti goat biotinylated Ig (1:200, SYN, 705065147, Jackson ImmunoResearch Inc., PA, USA), Alexa Fluor 488 goat-anti guinea pig Ig (1:500, VGLUT1, A11073, Molecular Probes, Oregon, USA), Alexa Fluor 488 goat-anti rabbit (1:2000, GFAP, A11034, Molecular Probes, Oregon, USA), donkey-anti rabbit biotinylated (1:500, Iba-1, 711-065-152, Jackson ImmunoResearch Inc., PA, USA), in blocking buffer for 1 h at RT. After washing 3×5 min with PBS-T, sections were incubated with Streptavidin-Cy3 (1:100 (GAP-43, SYN), 1:300 (NeuN), S6402, Sigma-Aldrich, Missouri, USA) in blocking buffer for 1 h at RT. Then, sections were washed 3×5 min with PBS-T, mounted with Pro Long Gold (P36931, Life Technologies, CA, USA) and cover slipped for 24 h before being sealed with nail polish. For Iba-1 staining, following secondary antibody, sections were incubated with an avidin/biotin complex (VECTASTAIN® Elite ABC kit, PK-6100, Vector Laboratories Inc., CA, USA) followed by DAB Substrate Kit (SK-4100, Vector Laboratories Inc., CA, USA) according to manufacturer's instructions. Next, sections were washed 3×5 min with PBS-T, dehydrated (70% EtOH 2 min, 95% EtOH 2 min, 100% EtOH 2 min) and cleared with xylene for 5 min. Slides were mounted with VectaMount medium (H-5000, Vector Laboratories Inc., CA, USA) and cover slipped.

NeuN positive cells, GFAP positive relative area, as well as GAP-43, SYN, and VGLUT1 positive puncta were counted by using MetaMorph software (ver. 7.8.6, Molecular Devices, CA, USA) on confocal images obtained with a 20× (NeuN and GFAP) or 63× (GAP-43, SYN, and VGLUT1) objective (Carl Zeiss LSM 700 Laser Scanning Microscope, Jena, Germany). Iba-1 positive cell somata were counted on bright field images obtained with a 20× objective (Nikon Eclipse 80i). The entire region of CA1, CA3 and DG was imaged for NeuN, GFAP and Iba-1 analysis, while stratum oriens of CA1 and molecular layer of DG were used for sections stained with GAP-43, SYN, and VGLUT1 antibodies. Three sections per animal (208 µm apart) were used for the analysis and the data were presented as either density (positive cells/µm2) for NeuN and Iba-1 or density (positive puncta/µm2) and mean area of the positive punctum (µm2) for GAP-43, SYN, and VGLUT1. For GFAP, the data were presented as positive area relative to the total area (%).

Statistical Analysis

Data were analyzed with IBM SPSS Statistics 20 (New York, USA) and GraphPad Prism 6.0f (GraphPad Software Inc., CA, USA). The Gaussian distribution of data was verified using the Kolmogorov-Smirnov test, the variance homogeneity was assessed using the Levene Test.

Unpaired t test was used to analyze the cue-induced fear conditioning experimental data. For the analysis of the total exploration time during the object recognition test and the open field experiment, one-way Analysis of Variance (ANOVA) was used, followed by a Tukey's multiple comparisons post-hoc test. Two-way ANOVA, with a Tukey's multiple comparisons post-hoc test, was used to analyze time spent exploring individual objects during the object recognition test, as well as the histomorphologic data and image analysis data. Two-way repeated measures ANOVA with a Tukey's multiple comparisons post-hoc test were used to analyze the body weight. Data are presented as mean±SEM. P values <0.05 were considered statistically significant.

Results

Intranasal C3a Treatment Ameliorates HI-Induced Cognitive Impairment in a C3aR-Dependent Manner The inventors previously reported that single i.c.v. injection of C3a 1 h after HI induction prevented HI-induced cognitive impairment when mice were tested as adults (Järlestedt et al., 2013). To determine whether such a protective effect of C3a can be achieved by intranasal administration, mice received C3a or PBS once daily for 7 days starting 1 h after HI induction. As in the previous study (Järlestedt et al., 2013), memory function was assessed using cue-induced fear conditioning 42 days later (FIG. 7A). The inventors observed that mice subjected to HI and treated with C3a showed a significantly increased freezing behavior after presentation of the conditioned cue compared with mice subjected to HI and treated with PBS (p<0.05), suggesting an enhanced memory function in C3a treated mice (FIG. 7B). Thus the effect of intranasal treatment with C3a is comparable to the previously reported effect of single intracerebroventricular injection of C3a (Järlestedt et al., 2013), FIG. 7C. Next, to investigate whether the protective effect of intranasal C3a against HI-associated cognitive deficit is mediated through the canonical C3a receptor C3aR, the inventors applied the same experimental protocol to C3aR$^{-/-}$ mice. The extent of freezing in cue-induced fear conditioning on P51 did not differ between C3aR$^{-/-}$ mice treated with C3a or PBS. Jointly, these results indicate that intranasal treatment with C3a ameliorates the HI-induced cognitive impairment and the protective effect of intranasal C3a administration on memory function after neonatal HI injury is mediated through C3aR.

To further assess the protective effects of intranasal C3a treatment on cognitive performance of mice after neonatal HI and to determine whether the effects can be achieved after a shorter treatment period, the inventors treated another cohort of mice with intranasal C3a or PBS for 3 days starting 1 h post-HI and assessed short and long-term memory at P53-P54 using object recognition test. The inventors found that in the familiarization phase the exploratory behavior was not altered by HI or C3a treatment. Although HI injury did not affect the short-term memory, as assessed at 6 h after the familiarization, the C3a treated mice spent more time exploring the novel object compared with the PBS-treated mice post-HI (p<0.01, FIG. 8B), which was also reflected in longer total object exploration time (p<0.05, FIG. 8C). When exploratory behavior was tested 24 h after familiarization, the mice treated with PBS post-HI spent comparable time exploring the novel and familiar objects. In contrast, the sham-operated and C3a treated mice spent significantly longer time exploring the novel compared to familiar object (p<0.001 and p<0.05, respectively; FIG. 8D). Further, the total object exploration time of C3a treated mice was longer compared to PBS treated mice (p<0.05; FIG. 8E). Jointly, these results indicate that long-term memory is impaired in adult mice subjected to neonatal HI and intranasal C3a treatment is protective against such cognitive impairment.

Exploratory Behavior and Locomotion are not Altered by HI Injury or C3a Treatment To confirm that HI or C3a treatment did not affect general exploratory behavior or locomotion of mice, the inventors used an open field evaluation of sham mice treated with PBS and mice subjected to HI and treated with PBS or C3a for 3 days. Mice in all groups showed comparable average speed, activity levels, locomotion time and distance travelled in all three groups at P50, indicating that HI or C3a treatment did not affect general exploratory and locomotor activities. Furthermore, there were no differences between groups regarding the distance travelled and time spent in the center of the arena or the number of rearing and grooming episodes, indicating that anxiety-like behavior was not induced by HI or C3a treatment.

Intranasal C3a Ameliorates HI-Induced Glial Response

Figure 9:
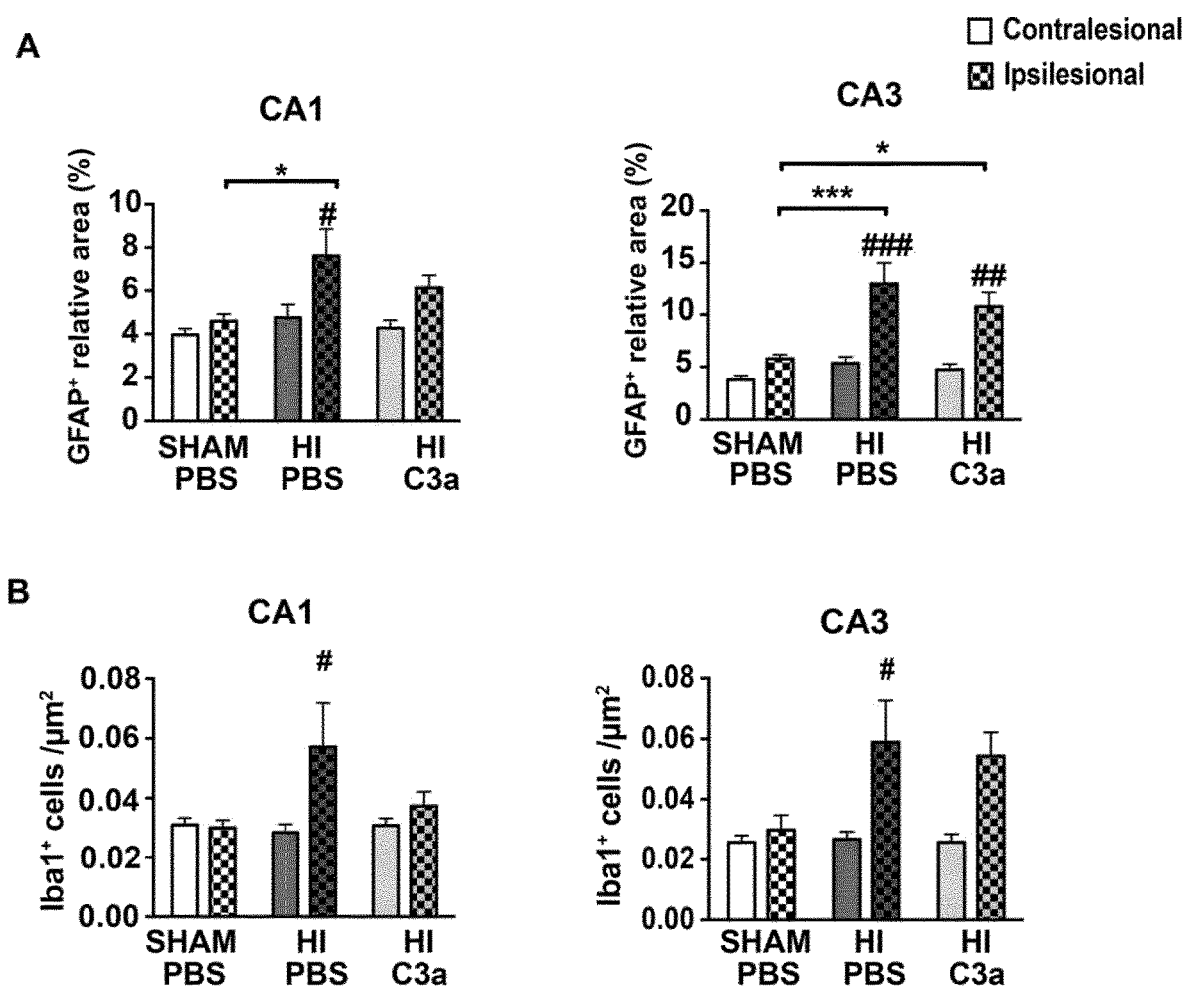
FIG. 9 shows that intranasal C3a ameliorates hypoxia-ischemia-induced reactive gliosis. (A) GFAP positive area relative to total area of CA1 and CA3. (B) Density of Iba-1 positive cells in CA1 and CA3. Mean±SEM. (n=6 per group). #p<0.05, ##p<0.01, ###p<0.001 ipsilesional vs. contralesional; *p<0.05, ***p<0.001 HI vs. sham by two-way ANOVA and Tukey's multiple comparisons post-hoc test. HI, hypoxic-ischemic injury. GFAP, glial fibrillary acidic protein. Iba-1, ionized calcium-binding adapter molecule 1.

To determine the effect of C3a treatment on glial responses, the inventors quantified GFAP and Iba-1$^+$ immunoreactivity in the CA/DG of the dorsal hippocampus at P55 in mice treated for 3 days after HI. The inventors found that HI on P9 led to an increase in GFAP$^+$ area in the ipsilateral compared with contralateral CA and DG regions in PBS treated mice, indicating HI-induced astrocyte activation. In both CA1 and CA3, this increase was also apparent in comparison with sections from sham mice. The proportion of GFAP relative area in CA1 and DG of C3a treated mice did not differ between the hemispheres or in comparison with sham mice (FIG. 9A). Mice subjected to HI and administered PBS exhibited higher density of Iba-1$^+$ cells in the ipsilateral CA and DG compared to contralateral CA and DG, indicating HI-induced microglial proliferation. In C3a treated mice, the density of Iba-1$^+$ cells did not differ between the hemispheres (FIG. 9B). Jointly, these results provide the evidence for ameliorated response of astrocytes and microglia in the C3a treated mice.

Intranasal C3a Does Not Affect HI-Induced Loss of Hippocampal Tissue

Consistent with the inventor's previous report (Järlestedt et al., 2013), moderate HI at P9 resulted in more than 50% reduction in the volume of the hippocampus in the injured compared to contralesional hemisphere at P51-55 (p<0.001). Regardless of the treatment length, intranasal C3a administration did not affect HI-induced loss of hippocampal tissue in WT or C3aR$^{-/-}$ mice.

To assess potential adverse effects of intranasal C3a administration on the overall animal health status and development, the inventors recorded animal weight gain across surgeries, treatments and different genotype conditions. The results show that neither the surgery nor the C3a treatment affected body weight gain in mice, thus excluding any pronounced adverse effect of the C3a treatment. Together, these results demonstrate that the intranasal treatment of mice with C3a is safe but does not have any measurable neuroprotective or growth stimulatory effect in the HI injured hippocampus.

Intranasal C3a Does Not Affect HI-Induced Decrease in Neuronal Density in the Dorsal Hippocampus Next, to determine the effect of C3a treatment on neuronal density, the inventors quantified NeuN$^+$ cells in the CA/DG of the dorsal hippocampus at P55 in mice treated for 3 days following HI. The inventors found that in CA1 and CA3, neuronal density was decreased in the ipsilesional hemisphere compared with contralesional hemisphere of both HI groups (p<0.01 and p<0.05, respectively). The number of NeuN$^+$ cells of the injured CA1 of PBS but not C3a treated mice was lower compared with sham mice (p<0.05). In the injured CA3 of C3a but not PBS treated mice, the numbers of NeuN$^+$ cells were lower compared with sham mice (p<0.01). No effect of HI or C3a treatment was found with regard to NeuN$^+$ cell density in the DG (data not shown). Jointly, these results demonstrate that neonatal HI leads to a substantial reduction in neuronal density in the CA of the dorsal hippocampus, this neuronal loss is not substantially affected by intranasal C3a treatment.

HI Leads to the Increase in GAP-43 Expression in the Dorsal Hippocampus that is not Affected by C3a Treatment Next, the inventors performed immunostaining with antibodies against GAP-43, a phosphoprotein localized in the neuronal growth cone that is involved in neurite extension and regarded as a surrogate marker of axonal plasticity (Benowitz and Routtenberg, 1997); it also mediates glial plasticity during astrogliosis (Hung et al., 2016). GAP-43 expression is highly upregulated in the adult cortex after ischemic stroke (Carmichael et al., 2005). The inventors did not find any differences between groups with regard to the density of GAP-43$^+$ puncta in the CA1. However, the average GAP-43$^+$ punctum area in the CA1 of the HI injured hippocampus of PBS treated, but not C3a treated, mice was larger compared with sham mice (p<0.05). No effect of HI or C3a treatment was found with regard to the expression of GAP-43 in the dentate gyrus. These data show that in response to HI, the different regions of the dorsal hippocampus respond differently to HI with regard to the expression of GAP-43.

The inventors also used antibodies against synapsin I (a pan-synaptic marker, (Micheva et al., 2010)) and VGLUT1 that has been shown to visualize the majority of glutamatergic synapses (Micheva et al., 2010). The inventors did not find any differences in the CA1 or dentate gyrus of the dorsal hippocampus in the density or average area of synapsin I$^+$ and VGLUT1$^+$ puncta between the groups or between the HI injured and contralesional hemisphere. As the VGLUT1 positive synapses stand for approximately 75% of all synapses visualized by antibodies against synapsin I and quantified at array tomography level (Micheva et al., 2010), the higher density of VGLUT1 positive puncta as compared to the density of puncta visualized by the antibody against synapsin I in the inventor's study conceivably reflect the difference in affinity and detection threshold between the antibodies used.

Discussion

The inventors have identified that intranasal C3a treatment ameliorates HI-induced cognitive impairment as assessed by two different behavioural paradigms. The inventors also show that the positive effects of C3a treatment on cognitive function are lost in the absence of C3aR. Intranasal C3a treatment ameliorated reactive gliosis in the CA1 and DG but did not reverse HI-induced hippocampal tissue loss/atrophy or reduction in neuronal density. Likewise, axonal sprouting and synaptic density, as assessed by the expression of GAP-43 and synapsin I together with VGLUT1 immunohistochemistry, respectively, in the hippocampus were not affected by intranasal C3a treatment.

While over-expression of C3a in reactive astrocytes was beneficial in terms of tissue protection, single dose intraventricular administration of C3a 1 h after HI induction was not neuroprotective (Järlestedt et al., 2013). The single dose C3a treatment did, however, prevent HI-induced cognitive impairment in wild-type mice as assessed 42 days later (Järlestedt et al., 2013). These results, together with the present data suggest that the reversal of HI-induced cognitive impairment by C3a is independent of neuronal density. In support of this notion, exposure to enriched environment was effective in recovering declarative but not aversive memory impairment and preserved hippocampal dendritic spine density loss after neonatal HI injury in rats (Rojas et al., 2013). Environmental enrichment, however, did not affect HI-induced tissue atrophy in the hippocampus (Pereira et al., 2008). Similarly, estradiol therapy improved behavioural performance but did not reverse the HI-induced loss of hippocampal volume (Waddell et al., 2016).

The inventors observed that HI led to increased expression of GAP-43 in the hippocampal CA1 but the GAP-43 expression was not further increased by intranasal C3a treatment. Thus, the positive effects of intranasal C3a on cognitive performance of mice do not appear to be mediated via increased expression of markers of spouting axons or synapses but rather involve other components of neuronal functioning such as modulation of synaptic plasticity. In support of this notion, in vitro, C3a increased neurite outgrowth of newly differentiated neurons (Shinjyo et al., 2009) and basal C3aR signalling has been suggested to play a role in normal dendritic extension (Lian et al., 2015). In addition, C3aR signalling was shown to increase synaptic strength by promoting membrane localization of a-amino-3-hydroxy-5-methyl-4-isoxazolepropionic acid (AMPA) receptors (Lian et al., 2015). In adult mice, single intraventricular injection of 10 µmol C3a 30 min prior to training session was reported to ameliorate amnesia induced by global cerebral ischemia when assessed 24 h later, although the underlying mechanisms were not addressed by the authors (Jinsmaa et al., 2000). The inventor's findings of the reversal of HI-induced cognitive impairment by intranasal C3a are in line with these previous reports and provide a strong evidence for the role of C3a in protection against injury-induced amnesia. The anti-amnestic effect of C3a observed after brief intranasal treatment with the peptide in the absence of any detectable adverse effects of the treatment provides direct evidence that targeting C3aR in the injured immature brain could be clinically feasible and potentially applicable to the treatment of infants at high risk of developing HIE.

Consistent with previous reports (Chavez-Valdez et al., 2012; Qiu et al., 2007; Teo et al., 2015) the inventors observed HI-induced astrocyte activation in the ipsilateral hippocampus. This astroglial response, which persists for at least 6 weeks after HI, was ameliorated by intranasal C3a treatment. These findings suggest that the beneficial effects of intranasal C3a treatment in terms of cognitive performance may be mediated, at least partially by astrocytes. This reasoning is further supported by the inventor's previous data demonstrating that C3a, in a C3aR-dependent manner, attenuated ischemia-induced upregulation of GFAP in cultured primary astrocytes and increased astrocyte survival after ischemic stress (Shinjyo et al., 2016).

Previous study found increased density of microglial cells in the ipsilateral hippocampus of juvenile mice 7 to 9 days post-HI (Cikla et al., 2016; Jantzie et al., 2005). The inventor's data demonstrate that this HI-induced proliferative response of microglia is evident even after the mice reached adulthood and can be attenuated by intranasal C3a treatment. In the absence of any measurable effect of C3a treatment on neuronal density or the expression of synaptic markers, these findings further support the contention that the effects of C3a on neuronal function are conceivably mediated through the glial compartment. The specific mechanisms underlying the beneficial effects of intranasal C3a on the neonatal brain in the context of HI injury warrant further investigation.

Conclusion

The inventor's results demonstrate that a pharmacological treatment that targets endogenous C3aR using a clinically feasible non-invasive mode of administration can reverse HI-induced cognitive impairment, conceivably through targeting the glial compartment. Intranasal administration appears to be a plausible route to deliver C3aR agonists into the brain of asphyxiated infants at high risk of developing HIE.

REFERENCES

Arumugam T V, Woodruff T M, Lathia J D, Selvaraj P K, Mattson M P, Taylor S M. Neuroprotection in stroke by complement inhibition and immunoglobulin therapy. Neuroscience 2009; 158: 1074-89.

Arvidsson A, Collin T, Kirik D, Kokaia Z, Lindvall O. Neuronal replacement from endogenous precursors in the adult brain after stroke. Nat Med 2002; 8: 963-70.

Baskin Y K, Dietrich W D, Green E J. Two effective behavioral tasks for evaluating sensorimotor dysfunction following traumatic brain injury in mice. J Neurosci Methods 2003; 129: 87-93.

Benowitz L I, Rodriguez W R, Neve R L. The pattern of GAP-43 immunostaining changes in the rat hippocampal formation during reactive synaptogenesis. Brain Res Mol Brain Res 1990; 8: 17-23.

Benowitz L I, Routtenberg A. GAP-43: an intrinsic determinant of neuronal development and plasticity. Trends Neurosci 1997; 20: 84-91.

Boos L, Campbell I L, Ames R, Wetsel R A, Barnum S R. Deletion of the complement anaphylatoxin C3a receptor attenuates, whereas ectopic expression of C3a in the brain exacerbates, experimental autoimmune encephalomyelitis. J Immunol 2004; 173: 4708-14.

Calautti C, Baron J C. Functional neuroimaging studies of motor recovery after stroke in adults: a review. Stroke 2003; 34: 1553-66.

Carmichael S T, Archibeque I, Luke L, Nolan T, Momiy J, Li S. Growth-associated gene expression after stroke: evidence for a growth-promoting region in peri-infarct cortex. Exp Neurol 2005; 193: 291-311.

Carmichael S T, Chesselet M F. Synchronous neuronal activity is a signal for axonal sprouting after cortical lesions in the adult. J Neurosci 2002; 22: 6062-70.

Carmichael S T, Wei L, Rovainen C M, Woolsey T A. New patterns of intracortical projections after focal cortical stroke. Neurobiol Dis 2001; 8: 910-22.

Chen J, Cui X, Zacharek A, Jiang H, Roberts C, Zhang C, et al. Niaspan increases angiogenesis and improves functional recovery after stroke. Ann Neurol 2007; 62: 49-58.

Costa C, Zhao L, Shen Y, Su X, Hao L, Colgan S P, et al. Role of complement component C5 in cerebral ischemia/reperfusion injury. Brain Res 2006; 1100: 142-51.

Cui X, Chopp M, Zacharek A, Cui Y, Roberts C, Chen J. The neurorestorative benefit of GW3965 treatment of stroke in mice. Stroke 2013; 44: 153-61.

Cui X, Chopp M, Zacharek A, Roberts C, Buller B, Ion M, et al. Niacin treatment of stroke increases synaptic plasticity and axon growth in rats. Stroke 2010; 41: 2044-9.

De Simoni M G, Storini C, Barba M, Catapano L, Arabia A M, Rossi E, et al. Neuroprotection by complement (C1) inhibitor in mouse transient brain ischemia. J Cereb Blood Flow Metab 2003; 23: 232-9.

Dekker L V, De Graan P N, Pijnappel P, Oestreicher A B, Gispen W H. Noradrenaline release from streptolysin O-permeated rat cortical synaptosomes: effects of calcium, phorbol esters, protein kinase inhibitors, and antibodies to the neuron-specific protein kinase C substrate B-50 (GAP-43). J Neurochem 1991; 56: 1146-53.

Dijkhuizen R M, Ren J, Mandeville J B, Wu O, Ozdag F M, Moskowitz M A, et al. Functional magnetic resonance imaging of reorganization in rat brain after stroke. Proc Natl Acad Sci USA 2001; 98: 12766-71.

Ducruet A F, Zacharia B E, Sosunov S A, Gigante P R, Yeh M L, Gorski J W, et al. Complement inhibition promotes endogenous neurogenesis and sustained anti-inflammatory neuroprotection following reperfused stroke. PLoS One 2012; 7: e38664.

Fang Y, Zhang T, Lidell L, Xu X, Lycke N, Xiang Z. The immune complex CTA1-DD/IgG adjuvant specifically targets connective tissue mast cells through FcgammaRIIIA and augments anti-HPV immunity after nasal immunization. Mucosal Immunol 2013; 6: 1168-78.

Feigin V L, Forouzanfar M H, Krishnamurthi R, Mensah G A, Connor M, Bennett D A, et al. Global and regional burden of stroke during 1990-2010: findings from the Global Burden of Disease Study 2010. Lancet 2014; 383: 245-54.

Ganeshina O, Berry R W, Petralia R S, Nicholson D A, Geinisman Y. Synapses with a segmented, completely partitioned postsynaptic density express more AMPA receptors than other axospinous synaptic junctions. Neuroscience 2004; 125: 615-23.

Gong P, Zhao H, Hua R, Zhang M, Tang Z, Mei X, et al. Mild hypothermia inhibits systemic and cerebral complement activation in a swine model of cardiac arrest. J Cereb Blood Flow Metab 2015; 35: 1289-95.

Gu W, Brännström T, Wester P. Cortical neurogenesis in adult rats after reversible photothrombotic stroke. J Cereb Blood Flow Metab 2000; 20: 1166-73.

Heese K, Hock C, Otten U. Inflammatory signals induce neurotrophin expression in human microglial cells. J Neurochem 1998; 70: 699-707.

Hiu T, Farzampour Z, Paz J T, Wang E H, Badgely C, Olson A, et al. Enhanced phasic GABA inhibition during the repair phase of stroke: a novel therapeutic target. Brain 2016; 139: 468-80.

Hou X E, Dahlström A. Synaptic vesicle proteins and neuronal plasticity in adrenergic neurons. Neurochem Res 2000; 25: 1275-300.

Huang J, Kim L J, Mealey R, Marsh H C, Jr., Zhang Y, Tenner A J, et al. Neuronal protection in stroke by an sLex-glycosylated complement inhibitory protein. Science 1999; 285: 595-9.

Hung C C, Lin C H, Chang H, Wang C Y, Lin S H, Hsu P C, et al. Astrocytic GAP43 Induced by the TLR4/NF-kappaB/STAT3 Axis Attenuates Astrogliosis-Mediated Microglial Activation and Neurotoxicity. J Neurosci 2016; 36: 2027-43.

Jander S, Kraemer M, Schroeter M, Witte O W, Stoll G. Lymphocytic infiltration and expression of intercellular adhesion molecule-1 in photochemically induced ischemia of the rat cortex. J Cereb Blood Flow Metab 1995; 15: 42-51.

Järlestedt K, Rousset C I, Stahlberg A, Sourkova H, Atkins A L, Thornton C, et al. Receptor for complement peptide C3a: a therapeutic target for neonatal hypoxic-ischemic brain injury. FASEB J 2013; 27: 3797-804.

Jauneau A C, Ischenko A, Chatagner A, Benard M, Chan P, Schouft M T, et al. Interleukin-1beta and anaphylatoxins exert a synergistic effect on NGF expression by astrocytes. J Neuroinflammation 2006; 3: 8.

Jones T A. Multiple synapse formation in the motor cortex opposite unilateral sensorimotor cortex lesions in adult rats. J Comp Neurol 1999; 414: 57-66.

Kildsgaard J, Hollmann T J, Matthews K W, Bian K, Murad F, Wetsel R A. Cutting edge: targeted disruption of the C3a receptor gene demonstrates a novel protective anti-inflammatory role for C3a in endotoxin-shock. J Immunol 2000; 165: 5406-9.

Kind L S. Fall in rectal temperature as an indication of anaphylactic shock in the mouse. J Immunol 1955; 74: 387-90.

Lee J K, Park M S, Kim Y S, Moon K S, Joo S P, Kim T S, et al. Photochemically induced cerebral ischemia in a mouse model. Surg Neurol 2007; 67: 620-5.

Li S, Carmichael S T. Growth-associated gene and protein expression in the region of axonal sprouting in the aged brain after stroke. Neurobiol Dis 2006; 23: 362-73.

Li S, Overman J J, Katsman D, Kozlov S V, Donnelly C J, Twiss J L, et al. An age-related sprouting transcriptome provides molecular control of axonal sprouting after stroke. Nat Neurosci 2010; 13: 1496-504.

Lian H, Yang L, Cole A, Sun L, Chiang A C, Fowler S W, et al. NFkappaB-activated astroglial release of complement C3 compromises neuronal morphology and function associated with Alzheimer's disease. Neuron 2015; 85: 101-15.

Liauw J, Hoang S, Choi M, Eroglu C, Sun G H, Percy M, et al. Thrombospondins 1 and 2 are necessary for synaptic plasticity and functional recovery after stroke. J Cereb Blood Flow Metab 2008; 28: 1722-32.

Lin L H, Bock S, Carpenter K, Rose M, Norden J J. Synthesis and transport of GAP-43 in entorhinal cortex neurons and perforant pathway during lesion-induced sprouting and reactive synaptogenesis. Brain Res Mol Brain Res 1992; 14: 147-53.

Lochhead J J, Thorne R G. Intranasal delivery of biologics to the central nervous system. Adv Drug Deliv Rev 2012; 64: 614-28.

Lu P, Yang H, Jones L L, Filbin M T, Tuszynski M H. Combinatorial therapy with neurotrophins and cAMP promotes axonal regeneration beyond sites of spinal cord injury. J Neurosci 2004; 24: 6402-9.

Luke L M, Allred R P, Jones T A. Unilateral ischemic sensorimotor cortical damage induces contralesional synaptogenesis and enhances skilled reaching with the ipsilateral forelimb in adult male rats. Synapse 2004; 54: 187-99.

Micheva K D, Busse B, Weiler N C, O'Rourke N, Smith SJ. Single-synapse analysis of a diverse synapse population: proteomic imaging methods and markers. Neuron 2010; 68: 639-53.

Mocco J, Mack W J, Ducruet A F, Sosunov S A, Sughrue M E, Hassid B G, et al. Complement component C3 mediates inflammatory injury following focal cerebral ischemia. Circ Res 2006; 99: 209-17.

Nowicka D, Rogozinska K, Aleksy M, Witte O W, Skangiel-Kramska J. Spatiotemporal dynamics of astroglial and microglial responses after photothrombotic stroke in the rat brain. Acta Neurobiol Exp (Wars) 2008; 68: 155-68.

Pekna M, Pekny M, Nilsson M. Modulation of neural plasticity as a basis for stroke rehabilitation. Stroke 2012; 43: 2819-28.

Porritt M J, Andersson H C, Hou L, Nilsson Å, Pekna M, Pekny M, et al. Photothrombosis-induced infarction of the mouse cerebral cortex is not affected by the Nrf2-activator sulforaphane. PLoS One 2012; 7: e41090.

Rahpeymai Y, Hietala M A, Wilhelmsson U, Fotheringham A, Davies I, Nilsson A K, et al. Complement: a novel factor in basal and ischemia-induced neurogenesis. EMBO J 2006; 25: 1364-74.

Schallert T, Fleming S M, Leasure J L, Tillerson J L, Bland S T. CNS plasticity and assessment of forelimb sensorimotor outcome in unilateral rat models of stroke, cortical ablation, parkinsonism and spinal cord injury. Neuropharmacology 2000; 39: 777-87.

Schroeter M, Jander S, Witte O W, Stoll G. Local immune responses in the rat cerebral cortex after middle cerebral artery occlusion. J Neuroimmunol 1994; 55: 195-203.

Shinjyo N, de Pablo Y, Pekny M, Pekna M. Complement Peptide C3a Promotes Astrocyte Survival in Response to Ischemic Stress. Mol Neurobiol 2015: doi: 10.1007/s12035-015-9204-4.

Shinjyo N, Ståhlberg A, Dragunow M, Pekny M, Pekna M. Complement-derived anaphylatoxin C3a regulates in vitro differentiation and migration of neural progenitor cells. Stem Cells 2009; 27: 2824-32.

Takatsuru Y, Fukumoto D, Yoshitomo M, Nemoto T, Tsukada H, Nabekura J. Neuronal circuit remodeling in the contralateral cortical hemisphere during functional recovery from cerebral infarction. J Neurosci 2009; 29: 10081-6.

Toni N, Buchs P A, Nikonenko I, Bron C R, Muller D. LTP promotes formation of multiple spine synapses between a single axon terminal and a dendrite. Nature 1999; 402: 421-5.

Vasek M J, Garber C, Dorsey D, Durrant D M, Bollman B, Soung A, et al. A complement-microglial axis drives synapse loss during virus-induced memory impairment. Nature 2016; 534: 538-43.

Vavrek R, Girgis J, Tetzlaff W, Hiebert G W, Fouad K. BDNF promotes connections of corticospinal neurons onto spared descending interneurons in spinal cord injured rats. Brain 2006; 129: 1534-45.

Walker F R, Jones K A, Patience M J, Zhao Z, Nilsson M. Stress as necessary component of realistic recovery in animal models of experimental stroke. J Cereb Blood Flow Metab 2014; 34: 208-14.

Watson B D, Dietrich W D, Busto R, Wachtel M S, Ginsberg M D. Induction of reproducible brain infarction by photochemically initiated thrombosis. Ann Neurol 1985; 17: 497-504.

Wieloch T, Nikolich K. Mechanisms of neural plasticity following brain injury. Curr Opin Neurobiol 2006; 16: 258-64.

Winship I R, Murphy T H. Remapping the somatosensory cortex after stroke: insight from imaging the synapse to network. Neuroscientist 2009; 15: 507-24.

Yang S, Wang X, Zhang X, Lu Y, Wang Z. Neuroprotective effects of the SCR1-3 functional domain of CR1 on acute cerebral ischemia and reperfusion injury in rats. Neurol Res 2013; 35: 976-83.

Bahadur, S., Pathak, K., 2012. Physicochemical and physiological considerations for efficient nose-to-brain targeting. Expert opinion on drug delivery 9, 19-31.

Becerril-Ortega, J., Bordji, K., Freret, T., Rush, T., Buisson, A., 2014. Iron overload accelerates neuronal amyloid-beta production and cognitive impairment in transgenic mice model of Alzheimer's disease. Neurobiol Aging 35, 2288-2301.

Bokisch, V. A., Muller-Eberhard, H. J., 1970. Anaphylatoxin inactivator of human plasma: its isolation and characterization as a carboxypeptidase. J Clin Invest 49, 2427-2436.

Chavez-Valdez, R., Martin, L. J., Flock, D. L., Northington, F. J., 2012. Necrostatin-1 attenuates mitochondrial dysfunction in neurons and astrocytes following neonatal hypoxia-ischemia. Neuroscience 219, 192-203.

Cikla, U., Chanana, V., Kintner, D. B., Covert, L., Dewall, T., Waldman, A., Rowley, P., Cengiz, P., Ferrazzano, P., 2016. Suppression of microglia activation after hypoxia-ischemia results in age-dependent improvements in neurologic injury. J Neuroimmunol 291, 18-27.

De Rosa, R., Garcia, A. A., Braschi, C., Capsoni, S., Maffei, L., Berardi, N., Cattaneo, A., 2005. Intranasal administration of nerve growth factor (NGF) rescues recognition memory deficits in AD11 anti-NGF transgenic mice. Proc Natl Acad Sci USA 102, 3811-3816.

Edwards, A. D., Brocklehurst, P., Gunn, A. J., Halliday, H., Juszczak, E., Levene, M., Strohm, B., Thoresen, M., Whitelaw, A., Azzopardi, D., 2010. Neurological outcomes at 18 months of age after moderate hypothermia for perinatal hypoxic ischaemic encephalopathy: synthesis and meta-analysis of trial data. BMJ (Clinical research ed.) 340, c363.

Finkelman, F. D., Khodoun, M. V., Strait, R., 2016. Human IgE-independent systemic anaphylaxis. The Journal of allergy and clinical immunology 137, 1674-1680.

Hagberg, H., Mallard, C., Ferriero, D. M., Vannucci, S. J., Levison, S. W., Vexler, Z. S., Gressens, P., 2015. The role of inflammation in perinatal brain injury. Nat Rev Neurol 11, 192-208.

Hedtjärn, M., Leverin, A.-L., Eriksson, K., Blomgren, K., Mallard, C., Hagberg, H., 2002. Interleukin-18 involvement in hypoxic-ischemic brain injury. J Neurosci. 22, 5910-5919.

Jantzie, L. L., Cheung, P. Y., Todd, K. G., 2005. Doxycycline reduces cleaved caspase-3 and microglial activation in an animal model of neonatal hypoxia-ischemia. J Cereb Blood Flow Metab 25, 314-324.

Järlestedt, K., Atkins, A. L., Hagberg, H., Pekna, M., Mallard, C., 2011. Trace fear conditioning detects hypoxic-ischemic brain injury in neonatal mice. Dev. Neurosci. 33, 222-230.

Jinsmaa, Y., Takahashi, M., Takahashi, M., Yoshikawa, M., 2000. Anti-analgesic and anti-amnesic effect of complement C3a. Life sciences 67, 2137-2143.

Kurinczuk, J. J., White-Koning, M., Badawi, N., 2010. Epidemiology of neonatal encephalopathy and hypoxic-ischaemic encephalopathy. Early Hum Dev 86, 329-338.

Leger, M., Quiedeville, A., Bouet, V., Haelewyn, B., Boulouard, M., Schumann-Bard, P., Freret, T., 2013. Object recognition test in mice. Nat Protoc 8, 2531-2537.

Leke, R., de Oliveira, D. L., Mussulini, B. H., Pereira, M. S., Kazlauckas, V., Mazzini, G., Hartmann, C. R., Silveira, T. R., Simonsen, M., Bak, L. K., Waagepetersen, H. S., Keiding, S., Schousboe, A., Portela, L. V., 2012. Impairment of the organization of locomotor and exploratory behaviors in bile duct-ligated rats. PLoS One 7, e36322.

Lin, S., Fan, L. W., Rhodes, P. G., Cai, Z., 2009. Intranasal administration of IGF-1 attenuates hypoxic-ischemic brain injury in neonatal rats. Exp. Neurol. 217, 361-370.

Mwaniki, M. K., Atieno, M., Lawn, J. E., Newton, C. R., 2012. Long-term neurodevelopmental outcomes after intrauterine and neonatal insults: a systematic review. Lancet 379, 445-452.

Pereira, L. O., Strapasson, A. C., Nabinger, P. M., Achaval, M., Netto, C. A., 2008. Early enriched housing results in partial recovery of memory deficits in female, but not in male, rats after neonatal hypoxia-ischemia. Brain Res 1218, 257-266.

Perez-Alcazar, M., Daborg, J., Stokowska, A., Wasling, P., Bjorefeldt, A., Kalm, M., Zetterberg, H., Carlström, K., C. T., E., Blomgren, K., Hanse, E., Pekna, M., 2014. Altered cognitive performance and synaptic function in the hippocampus of mice lacking C3. Exp. Neurol. 253, 154-164.

Qiu, L., Zhu, C., Wang, X., Xu, F., Eriksson, P. S., Nilsson, M., Cooper-Kuhn, C. M., Kuhn, H. G., Blomgren, K., 2007. Less neurogenesis and inflammation in the immature than in the juvenile brain after cerebral hypoxia-ischemia. J Cereb Blood Flow Metab 27, 785-794.

Rice, J. E.r., Vannucci, R. C., Brierley, J. B., 1981. The influence of immaturity on hypoxic-ischemic brain damage in the rat. Ann. Neurol. 9, 131-141.

Rojas, J. J., Deniz, B. F., Miguel, P. M., Diaz, R., Hermel Edo, E., Achaval, M., Netto, C. A., Pereira, L. O., 2013. Effects of daily environmental enrichment on behavior and dendritic spine density in hippocampus following neonatal hypoxia-ischemia in the rat. Exp Neurol 241, 25-33.

Scafidi, J., Hammond, T. R., Scafidi, S., Ritter, J., Jablonska, B., Roncal, M., Szigeti-Buck, K., Coman, D., Huang, Y., McCarter, R. J. J., Hyder, F., Horvath, T. L., Gallo, V., 2014. Intranasal epidermal growth factor treatment rescues neonatal brain injury. Nature 506, 230-234.

Schafer, D. P., Lehrman, E. K., Kautzman, A. G., Koyama, R., Mardinly, A. R., Yamasak, R., Ransohoff, R. M., Greenberg, M. E., Barres, B. A., Stevens, B., 2012. Microglia sculpt postnatal neural circuits in an activity and complement-dependent manner. Neuron 74, 691-705.

Sheldon, R. A., Sedik, C., Ferriero, D. M., 1998. Strain-related brain injury in neonatal mice subjected to hypoxia-ischemia. Brain Res. Bull. 810, 114-122.

Stevens, B., Allen, N. J., Vazquez, L. E., Howell, G. R., Christopherson, K. S., Nouri, N., Micheva, K. D., Mehalow, A. K., Huberman, A. D., Stafford, B., Sher, A., Litke, A. M., Lambris, J. D., Smith, S. J., John, S. W., Barres, B. A., 2007. The classical complement cascade mediates CNS synapse elimination. Cell 131, 1164-1178.

Svedin, P., Hagberg, H., Savman, K., Zhu, C., Mallard, C., 2007. Matrix metalloproteinase-9 gene knock-out protects the immature brain after cerebral hypoxia-ischemia. J Neurosci 27, 1511-1518.

Teo, J. D., Morris, M. J., Jones, N. M., 2015. Hypoxic postconditioning reduces microglial activation, astrocyte and caspase activity, and inflammatory markers after hypoxia-ischemia in the neonatal rat brain. Pediatr Res 77, 757-764.

Waddell, J., Hanscom, M., Shalon Edwards, N., McKenna, M. C., McCarthy, M. M., 2016. Sex differences in cell genesis, hippocampal volume and behavioral outcomes in a rat model of neonatal HI. Exp Neurol 275 Pt 2, 285-295.

Bellucci, A., Mercuri, N. B., Venneri, A., Faustini, G., Longhena, F., Pizzi, M., Missale, C., Spano, P., 2016. Review: Parkinson's disease: from synaptic loss to connectome dysfunction. Neuropathology and applied neurobiology 42, 77-94.

Burda, J. E., Bernstein, A. M., Sofroniew, M. V., 2016. Astrocyte roles in traumatic brain injury. Experimental neurology 275 Pt 3, 305-315.

Chen, L. W., Horng, L. Y., Wu, C. L., Sung, H. C., Wu, R. T., 2012. Activating mitochondrial regulator PGC-1alpha expression by astrocytic NGF is a therapeutic strategy for Huntington's disease. Neuropharmacology 63, 719-732.

Dawbarn, D., Allen, S. J., 2003. Neurotrophins and neurodegeneration. Neuropathology and applied neurobiology 29, 211-230.

Ducruet, A. F., Hassid, B. G., Mack, W. J., Sosunov, S. A., Otten, M. L., Fusco, D. J., Hickman, Z. L., Kim, G. H., Komotar, R. J., Mocco, J., Connolly, E. S., 2008. C3a receptor modulation of granulocyte infiltration after murine focal cerebral ischemia is reperfusion dependent. J Cereb Blood Flow Metab 28, 1048-1058.

Filli, L., Schwab, M. E., 2015. Structural and functional reorganization of propriospinal connections promotes functional recovery after spinal cord injury. Neural regeneration research 10, 509-513.

Goldshmit, Y., Lythgo, N., Galea, M. P., Turnley, A. M., 2008. Treadmill training after spinal cord hemisection in mice promotes axonal sprouting and synapse formation and improves motor recovery. Journal of neurotrauma 25, 449-465.

Hilton, B. J., Anenberg, E., Harrison, T. C., Boyd, J. D., Murphy, T. H., Tetzlaff, W., 2016. Re-Establishment of Cortical Motor Output Maps and Spontaneous Functional Recovery via Spared Dorsolaterally Projecting Corticospinal Neurons after Dorsal Column Spinal Cord Injury in Adult Mice. The Journal of neuroscience: the official journal of the Society for Neuroscience 36, 4080-4092.

Horner, P. J., Gage, F. H., 2000. Regenerating the damaged central nervous system. Nature 407, 963-970.

Klos, A., Tenner, A. J., Johswich, K. O., Ager, R. R., Reis, E. S., Kohl, J., 2009. The role of the anaphylatoxins in health and disease. Mol Immunol 46, 2753-2766.

Loane, D. J., Byrnes, K. R., 2010. Role of microglia in neurotrauma. Neurotherapeutics: the journal of the American Society for Experimental NeuroTherapeutics 7, 366-377.

Marlier, Q., Verteneuil, S., Vandenbosch, R., Malgrange, B., 2015. Mechanisms and Functional Significance of Stroke-Induced Neurogenesis. Frontiers in neuroscience 9, 458.

Mestriner, R. G., Pagnussat, A. S., Boisserand, L. S., Valentim, L., Netto, C. A., 2011. Skilled reaching training promotes astroglial changes and facilitated sensorimotor recovery after collagenase-induced intracerebral hemorrhage. Experimental neurology 227, 53-61.

Mufson, E. J., Mahady, L., Waters, D., Counts, S. E., Perez, S. E., DeKosky, S. T., Ginsberg, S. D., Ikonomovic, M. D., Scheff, S. W., Binder, L. I., 2015. Hippocampal plasticity during the progression of Alzheimer's disease. Neuroscience 309, 51-67.

Murphy, T. H., Corbett, D., 2009. Plasticity during stroke recovery: from synapse to behaviour. Nature reviews. Neuroscience 10, 861-872.

Nakagawa, H., Ueno, M., Itokazu, T., Yamashita, T., 2013. Bilateral movement training promotes axonal remodeling of the corticospinal tract and recovery of motor function following traumatic brain injury in mice. Cell death & disease 4, e534.

Pekny, M., Wilhelmsson, U., Pekna, M., 2014. The dual role of astrocyte activation and reactive gliosis. Neuroscience letters 565, 30-38.

Rynkowski, M. A., Kim, G. H., Garrett, M. C., Zacharia, B. E., Otten, M. L., Sosunov, S. A., Komotar, R. J., Hassid, B. G., Ducruet, A. F., Lambris, J. D., Connolly, E. S., 2009. C3a receptor antagonist attenuates brain injury after intracerebral hemorrhage. J Cereb Blood Flow Metab 29, 98-107.

Scheff, S. W., Price, D. A., Schmitt, F. A., Mufson, E. J., 2006. Hippocampal synaptic loss in early Alzheimer's disease and mild cognitive impairment. Neurobiology of aging 27, 1372-1384.

Shiromoto, T., Okabe, N., Lu, F., Maruyama-Nakamura, E., Himi, N., Narita, K., Yagita, Y., Kimura, K., Miyamoto, O., 2016. The Role of Endogenous Neurogenesis in Functional Recovery and Motor Map Reorganization Induced by Rehabilitative Therapy after Stroke in Rats. Journal of stroke and cerebrovascular diseases: the official journal of National Stroke Association.

Sun, D., Daniels, T. E., Rolfe, A., Waters, M., Hamm, R., 2015. Inhibition of injury-induced cell proliferation in the dentate gyrus of the hippocampus impairs spontaneous cognitive recovery after traumatic brain injury. Journal of neurotrauma 32, 495-505.

Tamakoshi, K., Ishida, A., Takamatsu, Y., Hamakawa, M., Nakashima, H., Shimada, H., Ishida, K., 2014. Motor skills training promotes motor functional recovery and induces synaptogenesis in the motor cortex and striatum after intracerebral hemorrhage in rats. Behavioural brain research 260, 34-43.

Ten, V. S., Yao, J., Ratner, V., Sosunov, S., Fraser, D. A., Botto, M., Sivasankar, B., Morgan, B. P., Silverstein, S., Stark, R., Polin, R., Vannucci, S. J., Pinsky, D., Starkov, A. A., 2010. Complement component C1q mediates mitochondria-driven oxidative stress in neonatal hypoxic-ischemic brain injury. J. Neurosci. 30, 2077-2087.

Warraich, Z., Kleim, J. A., 2010. Neural plasticity: the biological substrate for neurorehabilitation. P M & R: the journal of injury, function, and rehabilitation 2, S208-219.

Wu, F., Zou, Q., Ding, X., Shi, D., Zhu, X., Hu, W., Liu, L., Zhou, H., 2016. Complement component C3a plays a critical role in endothelial activation and leukocyte recruitment into the brain. J Neuroinflammation 13, 23.

Zang, D. W., Lopes, E. C., Cheema, S. S., 2005. Loss of synaptophysin-positive boutons on lumbar motor neurons innervating the medial gastrocnemius muscle of the SOD1G93A G1H transgenic mouse model of ALS. Journal of neuroscience research 79, 694-699.

The invention claimed is:

1. A method of improving recovery in a mammalian subject that has suffered an ischemic stroke, the method comprising administering to the subject a therapeutically effective amount of a composition comprising a human C3a receptor agonist and a pharmaceutically acceptable carrier,
wherein the composition is administered intranasally, beginning after the subacute phase of the ischemic stroke.

2. The method according to claim 1, wherein the subject is an adult human.

3. The method according to claim 2, wherein the human C3a receptor agonist is administered daily to the subject intranasally for a period effective to improve motor function in the subject.

4. The method according to claim 2, wherein the human C3a receptor agonist is administered daily to the subject intranasally for at least three weeks.

5. The method according to claim 2, wherein the human C3a receptor agonist is administered to the subject intranasally, beginning at least seven days following the ischemic stroke.

6. The method according to claim 5, wherein the human C3a receptor agonist is administered daily to the subject intranasally for at least three weeks.

7. The method according to claim 1, wherein the C3a receptor agonist comprises a peptide comprising amino acids 73-77 of SEQ ID NO: 1 at its C-terminus.

8. The method according to claim 1, wherein the C3a receptor agonist comprises a peptide comprising amino acids 65 to 77 of SEQ ID NO: 1.

9. The method according to claim 1, wherein the C3a receptor agonist comprises an amino acid sequence at least 90% identical to the human C3a amino acid sequence shown in SEQ ID NO: 1 and having C3a receptor agonist activity.

10. The method according to claim 1, wherein the C3a receptor agonist is a C3a peptide, Trp-Trp-Gly-Lys-Lys-Tyr-Arg-Ala-Ser-Lys-Leu-Gly-Leu-Ala-Arg (SEQ ID NO: 2); Phe-Leu-Pro-Leu-Ala-Arg (SEQ ID NO: 3); Phe-Ile-Pro-Leu-Ala-Arg (SEQ ID NO: 6); Phe-Trp-Thr-Leu-Ala-Arg (SEQ ID NO: 7); Phe-Leu-Thr-Leu-Ala-Arg (SEQ ID NO: 8); Boc-Leu-oxazole-Arg; Boc-Ile-oxazole-Arg; Boc-Ile-5-methyl-oxazole-Arg; 3-indole-carboxylic acid-Leu-imidazole-Arg; 3-indole-carboxylic acid-Leu-oxazole-Arg; 5-bromonicotinic acid-Leu-oxazole-Arg; 4-(biphenyl-4-yl)-4-oxobutanoic acid-Ile-oxazole-Arg; isoquinoline-1-Ile-oxazole-Arg; (2-Benzhydryl-4-methyl-1H-imidazole-5-carbonyl)-L-Arg; (2-Benzhydryl-1H-imidazole-5-carbonyl)-L-Arg; (2-Benzhydryl-1,5-dimethyl-1H-imidazole-4-carbonyl)-L-Arg; or 2-cyclohexyl-2-phenyl-N-[1-(3-pyridin-3-ylpropanoyl)piperidin-4-yl]acetamide.

11. The method according to claim 1, wherein the pharmaceutically acceptable carrier comprises phosphate-buffered saline or a gel comprised of one or more of colloidal silicon dioxide, cellulose, cellulose derivatives, polysaccharides, and polyvinyl alcohol.

12. The method according to claim 1, wherein the C3a receptor agonist comprises:
 (a) the amino acid sequence shown in SEQ ID NO: 1; or
 (b) an amino acid sequence at least 90% identical to (a) that has C3a receptor agonist activity; or
 (c) a fragment of (a) or (b) with C3a receptor agonist activity.

13. The method according to claim 12, wherein (b), the amino acid sequence at least 90% identical to (a), is identical across its entire length except for conservative substitutions.

14. The method according to claim 12, wherein (c), the fragments of (a) or (b) with C3a receptor agonist activity, include the six cysteine residues at positions equivalent to positions 22, 23, 36, 49, 56, and 57 of SEQ ID NO: 1.

* * * * *

UNITED STATES PATENT AND TRADEMARK OFFICE
CERTIFICATE OF CORRECTION

PATENT NO. : 11,266,715 B2
APPLICATION NO. : 16/462697
DATED : March 8, 2022
INVENTOR(S) : Marcela Pekna et al.

Page 1 of 1

It is certified that error appears in the above-identified patent and that said Letters Patent is hereby corrected as shown below:

On the Title Page

At item (87), Line 2, "May 24, 2011" should be -- May 24, 2018 --.

Signed and Sealed this
Twenty-fourth Day of January, 2023

Katherine Kelly Vidal
*Director of the United States Patent and Trademark Office*

SEQUENCE LISTING

<160> NUMBER OF SEQ ID NOS: 8

<210> SEQ ID NO 1
<211> LENGTH: 77
<212> TYPE: PRT
<213> ORGANISM: Homo sapiens

<400> SEQUENCE: 1

```
Ser Val Gln Leu Thr Glu Lys Arg Met Asp Lys Val Gly Lys Tyr Pro
1               5                   10                  15

Lys Glu Leu Arg Lys Cys Cys Glu Asp Gly Met Arg Glu Asn Pro Met
            20                  25                  30

Arg Phe Ser Cys Gln Arg Arg Thr Arg Phe Ile Ser Leu Gly Glu Ala
        35                  40                  45

Cys Lys Lys Val Phe Leu Asp Cys Cys Asn Tyr Ile Thr Glu Leu Arg
    50                  55                  60

Arg Gln His Ala Arg Ala Ser His Leu Gly Leu Ala Arg
65                  70                  75
```

<210> SEQ ID NO 2
<211> LENGTH: 15
<212> TYPE: PRT
<213> ORGANISM: Homo sapiens

<400> SEQUENCE: 2

```
Trp Trp Gly Lys Lys Tyr Arg Ala Ser Lys Leu Gly Leu Ala Arg
1               5                   10                  15
```

<210> SEQ ID NO 3
<211> LENGTH: 6
<212> TYPE: PRT
<213> ORGANISM: Homo sapiens

<400> SEQUENCE: 3

```
Phe Leu Pro Leu Ala Arg
1               5
```

<210> SEQ ID NO 4
<211> LENGTH: 9628
<212> TYPE: DNA
<213> ORGANISM: Homo sapiens

<400> SEQUENCE: 4

```
ctgtgaggtc agatagtggt ctagagcata agacttaact tattgccgga aacagagaga      60
gaacagaaga agagaaagct cagcaaattt tcttgccata cttcatgact tcactgtggc     120
taagtgtggg gaccagacag gactcgtgga gacatccagg tgctgaagcc ttcagctact     180
gtctcagttt tttggtaaga aaacctagac ctacctgatg acttgtgctt agcctgtttt     240
gctcattata ggtaatgagt ttgagtgtca ctatcttcta tttcccctat tccttctctg     300
actttgaatt cttttatctt atctctatgt ctaacttcct ttttctaaat attccacatt     360
gcatttgtct ttgcttttaa tattttcata gtggaattaa tagtgaattt ttacatcatt     420
```

```
tctttcctttt ctttgaattg gctatgtatt tcaccctgaa ctttgattcc agctgtcccc    480
attaatttgt ttttcaaata attgattgca cttttttttcc ctttccattt cctctttctt    540 tttttttattc ttttgcccat tccttattgc tactgactct gttatcctat tactacaatt    600
tgattctggg gtccactttt ctttctctat cacagtggaa ttttagtttc aggatattaa    660
ttacctttaa attacggctg gtcaacttag taataatttt ttttaatcct ctactaatct    720
taaacacata aaggtatggt attttttagcc aaattaactt gaagaaatgt aaaaagtaat    780
cttgctctgc aggactttt tttttttttt tttttttttga cacagagtct cactctgttg    840
cccaggctgg agtacagtag catgatctca gctcactgca acctccgcct cccaggttca    900
agcgattctc ctgcctcagc ctcctgagta ggtgggattg caggcacgtg ctaccacacc    960
cagttaaatt ttttttgtatt tttagtagag acagggttcc accatgttgg ccaggttggt   1020
ctcaaactcc tgacctcagg tgatctaccc gcctctgcct cccaaagtgc tgggattaca   1080
ggcgtgagcc accacaccca gccttgttct aaaggacttt taatccctga ctcctacata   1140
ctttcatttc aaaacagata ataacaatat ttaacatata gctcatgaca gataactcta   1200
tttttattaa aattttgctg tttgcagtcc ctgctactct agttcatgca gttctcggca   1260
gcttcccctt tattagcaat accatatatc tttttttttt taatgtgatt tttttttttt   1320
tttggtagta aaaacagcat ttgcctaaca gtcctcggac ctgaaatcca agaacctccc   1380
tagtaatgat tatatgcttg taatctaatt tgctgagttt cactgtcaaa cttgagaaat   1440
aaaagcagag aaaacgtagg ctgggcacag tggctcatgt ctgtaacccc agcacactgt   1500
gaggccaaca tgggaggatt gcttgagtcc aggagtttga gagcagcttg ggcaacatag   1560
caagacccta tctctacaaa caaacaaaca aacaacaac aacaacaaca acaaaatgag   1620
gagaggagag atgattacca agttttcttt cagccctagc atcccatgac tctattcttc   1680
tctcaatatt ttagggggt accgtgatag tatttaaata tctgagtaga caaggccatg   1740
gaaaggggaa tgagaataat ttcttcttct tttttttttt ttgagatgga gttttgcttt   1800
tgttgcccag gctggagtgt agtggcgcaa cctcggctca ccacaacctc tgcctcccag   1860
gttcaagcga ttctcctgcc tcagcctcct gagtagctgg gattacaggc atgtgccacc   1920
atgcccacct aattttgtat ttttagtaga cacagagttt ctccatgttg gataggctgg   1980
tctcaaactg acctcaggtg atctgcctgc cttggcttcc caaagtgctg ggataacagg   2040
tgtgagccac tgtgcccagc ccatgtcttc ttttttatta ttttgttgac ttgctatttt   2100
aacttctgct aatcatatga ggccctatgg caatatttgg ctgactcagc agaactactt   2160
tcaagtcaca aaaatatttt gagcctctat aaaagtaaaa tgttatttta tccagtaaaa   2220
attaggaatt tcacaaaaag aaagttaaaa gggacagcat gggaattaag gaagaggcct   2280
gggtaaggat tacatggata caaattagaa ttttagatgt aattgcaaaa gaaaaaaaaa   2340
gtcaaccccc aaaatgggca tccatctatt caagtaattt ttttttttctt ttttttctt   2400 ttgagacaga gtctctttgt catgcaggct ggagtgcagt ggtgcaatct cagctcactg   2460
caacctccac ctctccagtt caagcgattc tcgtgcctca gcctcccaag tagctgggat   2520
tacaagtgtg agctaccaca cccagctaat ttttgtattt ttggtagaga tgggattttg   2580
ccatgttagc caggctggtc ttgaactcct agccccaagc gatcttctcc cctcggcccc   2640
ccaaagtgct gcgattacag gcatgagcca ctgcgcccag cctttccaca taatctttaa   2700
ccttggtgtc tcataaggca ttatgttaaa ttatgtgaaa tgagcattta tgaataagac   2760 tccttttttac catcataaag tttaaatcca gaataataga ttagacagcc attataatta   2820
```

```
ttgtacaaga taaaatgtgt cattgcatat agaatatgaa aaaaaggttc aaacatgcgc    2880
acacacacaa attaagaagc tgaagacttg gtgaagggca taattccaga tagaagtaaa    2940
cagcattagc catggaacgg aaaatggcat taagttggaa tagtgaattg ttcaggaaag    3000
ctataaagca gggtacattt acgagcatgt tcacagttag gggaaggtaa tatcacagag    3060
gccaagagaa gagagtgtta agaagtcagt gtatctaatg acacatattg tggaaggtga    3120
ctgagaaaca aacgtttgga tttggttttt agaagtaatt ttagcagaat tatggaagca    3180
gaagatacat tacaaagaat taagaagttg gtggccggcc gggcctggtg gctcacatct    3240
gtaatcccgg gactttggga ggccgaggcg ggcggatcac caggtcagga atcaagatc    3300 atcctggcta acatggtgaa accccgtctc tactaaaaat acaaaaatta gccgggcgtg    3360
gtggtacacg cctgtaatcc cagctcctcg ggaggctgag gcagaagaat tgcttaaacc    3420
cgggatgcgg aggctgtagt gagccgagat cgcaccattg cactccagcc tgggagacag    3480
agcgagactc catcacaaaa aaaaaaaaaa aaaaaaaaa aagggccggg cgcggtggct    3540
cacgcctgta atcccaacac tttgggaggc cgaggcgggc ggatcgcctg aggtcgggag    3600
atcaacatca tcctggccaa catggagaaa ccccgttctc tactaaaaat acaaaaaaaa    3660
attagccggg catggtggcg catgcctgta atcccagcta ctgggaggct gaggcaggag    3720
aatcacttga acccgggagg aggaggttgc agtgagccaa gatcgcgcca ctgcactcca    3780
gcgtgggcaa caagagcgaa actccatctc aagaaaaaag aaaaaagaa gaagttagtg    3840 ttcagaacag taggcgtagg ccccaaaaca aagcagtatc cttgaaaaag agaaattatg    3900
ctaaattaag agacttaaga agaaagtgcg atctgaagta gatattgtcg tggacaagcc    3960
agctataaaa gatgtcttag ggacagttga aaaataatca tataaagggg ggggcatggt    4020
ggttcgtgcc tgtaatctca gcacttcggg aggccgagga agaatcagta gagcccagga    4080
gttggagacc agcctgagca acatagcaag accccatctt tacaaacaga aacaaaacag    4140
ataaaggtcg ggtattcctt atggtacata ttgtataatg tggagactgc taactgaaaa    4200
aagaaaaaaa tgtataaaaa atatgtattt acacccatgt tcattgatgc ataattcaca    4260
atagtcaaaa ggtgaaagca atccagatgt cctctgtgga atgactggat aaacaaaatg    4320
aagtatagac ctacaatgga atattattca gccttaaaaa gaaagaaaat tctgacccat    4380
gccacaacgc ggaggaagct tgaagacatt atgctaagtg aaatacacca gacacaaaaa    4440
gacaaatact gtgtgattcc acttagatca gatatctaaa gtagtcgaat tcatagaaat    4500
tgaaagtaca atggtgattg ccaggggctg agaaaaggag aaaatgggga attctttcct    4560
gagcacattt tcagttttgt aagatgaaaa agttctgaaa attggttgta caacgtgaat    4620
atggtaaaca ctactgaact gtgtacttaa aaatggtgaa gatggtaaat gttatgatac    4680
atgtgtttgg caattaaaat ttttttgtta gggccaggcg cggtggctcg cacctgtaat    4740
cccagcactt tgggagggag aggagggagg atcactcgag cctagcagtt caagagtagc    4800
ctggccaaca tggcaaaacc tgtctctgct aaaaatacaa aaattagttg gtacgttggt    4860
gggcaactgc agtcccagct actcaggagg ctgaggcacg ataattgctt gaacccggga    4920
ggcagaggct gcagtgagcc gagattgtat cactgcactc cagcctgaat gacggaggga    4980
gattctgtct caaaataat aataataata ataataaata aataaatgaa gcactgtccc    5040
acatattaga aggcttctag ccatcacagc ccctgctgtc taaagatacg catgtgtata    5100
cctaaatgca cacacacaca taaaaaagg tcaagaggat ataaattcag gtgctaaaat    5160
```

```
aataatcact gactagtgag tatatttta ttttctttt tgtttgtcta tattttccaa      5220
ttttcttcat gcatatttt tgcttttgta ataataaagc tcttttccca agttacggtc      5280
ataaaacaca aataaataag aaagaaatga taggtagtga ggaagtcaat gcagagggcc      5340
aacaactctt ggaaaatttg aaagcaaaag gagatggagt tgtatctaaa agacatcgct      5400
gagtctagag tacctctttc tgtggcggcg agtcctctga aaatctggtg gggagagtgg      5460
atgaagcttc tgccctcaga gaaatgagaa tatgtaaagt tgaagttttg catatcattt      5520
taggtggtga tggaacttcc taaaacccctt tcgtgacctc aggttggaga cctccagtcc      5580
agatatttt tgtgtgtttac ttatttagct tatttgttta tttttaaaca cactgggtga      5640
agaaaggagc cagtggaaaa accaagattg aaagtacaag aaagaggaga aatttacact      5700
aatatggact ccagatgag gctgtgattt tgatacacac ataaatcaat acagtagatt      5760
ttaaattgtc tatcatagga tgggcatggt ggctcatgcc tataatccca gcactttggg      5820
aggccaaggc aggcagatca cccgaggtca ggagttcaag accagcctgg ccaacatggc      5880
aaaacccccgt ctctactaaa aatacaaaaa ttagccaggc gtggtggtgc acgcctgtaa      5940
tcccagctac tctggaggct gaggcaggag aatcgcttga actcgggagg cggagcttac      6000
agtgagctga aatcaatcca ctgcactcca gcctgcgcga cagaggaaga ctctgtctga      6060
aaaataatta ataaattaat aaataaatat aattgtctat cagagaatgc ttttatgtgg      6120
tcccgtgtga ggtgaaggaa ggcaaactaa acagcgtga ggaccttctg gtttcatgat      6180
cccacatctt tatgtgggaa gattagaatc ctaagaatat gtatgcattt tcaaaaagat      6240
actgtttgtt ttaacatttt tttcatcttt ttgcagaagt ttagcaatgg cgtctttctc      6300
tgctgagacc aattcaactg acctactctc acagccatgg aatgagcccc cagtaattct      6360
ctccatggtc attctcagcc ttactttttt actgggattg ccaggcaatg ggctggtgct      6420
gtgggtggct ggcctgaaga tgcagcggac agtgaacaca atttggttcc tccacctcac      6480
cttggcggac ctcctctgct gcctctcctt gccccttctcg ctggctcact tggctctcca      6540
gggacagtgg ccctacggca ggttcctatg caagctcatc ccctccatca ttgtcctcaa      6600
catgtttgcc agtgtcttcc tgcttactgc cattagcctg gatcgctgtc ttgtggtatt      6660
caagccaatc tggtgtcaga atcatcgcaa tgtagggatg gcctgctcta tctgtggatg      6720
tatctgggtg gtggcttttg tgatgtgcat tcctgtgttc gtgtaccggg aaatcttcac      6780
tacagacaac cataatagat gtggctacaa atttggtctc tccagctcat tagattatcc      6840
agacttttat ggagatccac tagaaaacag gtctcttgaa acattgttc agccgcctgg      6900
agaaatgaat gataggttag atccttcctc tttccaaaca aatgatcatc cttggacagt      6960
ccccactgtc ttccaacctc aaacatttca aagaccttct gcagattcac tccctagggg      7020
ttctgctagg ttaacaagtc aaaatctgta ttctaatgta tttaaacctg ctgatgtggt      7080
ctcacctaaa atccccagtg ggttccctat tgaagatcac gaaaccagcc cactggataa      7140
ctctgatgct tttctctcta ctcattaaa gctgttccct agcgcttcta gcaattcctt      7200
ctacgagtct gagctaccac aaggtttcca ggattattac aattaggcc aattcacaga      7260
tgacgatcaa gtgccaacac cctcgtggc aataacgatc actaggctag tggtgggttt      7320
cctgctgccc tctgttatca tgatagcctg ttacagcttc attgtcttcc gaatgcaaag      7380
gggccgcttc gccaagtctc agagcaaaac ctttcgagtg gccgtggtgg tggtggctgt      7440
cttttcttgtc tgctgactc cataccacat ttttggagtc ctgtcattgc ttactgaccc      7500
agaaactccc ttggggaaaa ctctgatgtc ctgggatcat gtatgcattg ctctagcatc      7560
```

```
tgccaatagt tgctttaatc ccttccttta tgccctcttg gggaaagatt ttaggaagaa    7620
agcaaggcag tccattcagg gaattctgga ggcagcctct agtgaggagc tcacacgttc    7680
cacccactgt ccctcaaaca atgtcatttc agaaagaaat agtacaactg tgtgaaaatg    7740
tggagcagcc aacaagcagg ggctcttagg caatcacata gtgaaagttt ataagaggat    7800
gaagtgatat ggtgagcagc ggacttcaaa aactgtcaaa gaatcaatcc agcggttctc    7860
aaacggtaca cagactattg acatcagcat cacctagaaa cttgttagaa atgcaaattc    7920
tcaagccgca tcccagactt gctgaatcgg aatctctggg ggttgggacc cagcaagggc    7980
acttaacaaa ccctcgtttc tgattaatgc taaatgtaag aatcattgta aacattagtt    8040
ctatttctat cccaaactaa gctatgtgaa ataagagaag ctactttgtt tttaaatgat    8100
gttgaatatt tgtcgatatt tccatcatta aattttcct tagcattgtc taagtcttcc     8160
agattccatt taaaaccatt tcttgttctc ctacgtgagt gaaagatgat catatatcct    8220
aatgctttgt tgtcgtgtgg tgttgatggt tttaaacgaa aagaaagtgc aaaaagaaaa    8280
tgcctgtgaa gacaagaagc catgagactg agtctggagc atagggttat gcaatgatgc    8340
ctgtccctgg gaacacccct gggtacagga tatagaaatt ccactatta catgagttt     8400 ccactattac aactaaataa gcatctattg tgtgaaaact gactcatgaa atgttatgaa    8460
agctgtggtt tggggagttc tgtttcttct aactgcctac cggttgggca cctatttcc     8520 actcctcttc ctaagctcct taatttcctt attactcccc agcctccaaa tcttccacat    8580
cagactttgt gcctcaaaca acctctaatt tcgtaagatt ctagttactc ccttcctctt    8640
gctccaaatg aatactttct aagaaagtat ttcaagtgga aggagaaaga gggtggagga    8700
tggagcagca attcttctac tctctgcaac tgagtaccct accaggcttg ccatcacatt    8760
ttaaaacatg acgacaggca acttacatgc caaaattacc aaatatatct tctgggtttt    8820
ttaaatcctt ttctttgcca aagtaataca tgcacatagt tttaaaataa tttaataagg    8880
tatataatga aatatgaggt ctcctacctc actgtgccca aaagttccct cctcccactc    8940
tcatttccca gagataatcc ttgcacaatt ttagatgttt cctttgataa ttatcatgat    9000
gtttctaaat catgtgctta tgctgctctt ttctggaggc atgataaaac gacttcttgt    9060
tttgaaagat gaagatgttt atccaagcac cccatatttt taatttgttt atccagcatc    9120
ccaacattca ttaataacca tatttaatt cattcatgac cacatatttt tcttctactt     9180
tgtctataca ctccaaccat ttatatagct ttccttctgt cccttttca tttaaaacaa     9240 aattacctaa ctccctacca ccttctcatt tttctgtata tataaatgtt tgtgtcaaac    9300
gtctgaaatt tctggcttgt ttgtatcaca acgtggcctc atctaaacca aatacaatga    9360
tgtagtctaa aaacagaaaa tgacatgtgt tttagacctg caagcacacta tctgttcaat    9420 ggctgaggtg agggtctgga ctacagattt tttataaagt atatgcagaa aaattacaaa    9480
tcactaggaa ttctttcagt tgtgaagaat gtctgacata agatttgaag tgctacctt     9540 ccagcttata tattaatttg cttatatatt tgatatgaat aaatgctttt tttctcatgg    9600
gtccttgcga ggctcagaga tttatgaa                                       9628
```

<210> SEQ ID NO 5
<211> LENGTH: 482
<212> TYPE: PRT
<213> ORGANISM: Homo sapiens

<400> SEQUENCE: 5

-continued

```
Met Ala Ser Phe Ser Ala Glu Thr Asn Ser Thr Asp Leu Leu Ser Gln
1               5                   10                  15

Pro Trp Asn Glu Pro Val Ile Leu Ser Met Val Ile Leu Ser Leu
            20                  25                  30

Thr Phe Leu Leu Gly Leu Pro Gly Asn Gly Leu Val Leu Trp Val Ala
            35                  40                  45

Gly Leu Lys Met Gln Arg Thr Val Asn Thr Ile Trp Phe Leu His Leu
50                  55                  60

Thr Leu Ala Asp Leu Leu Cys Cys Leu Ser Leu Pro Phe Ser Leu Ala
65                  70                  75                  80

His Leu Ala Leu Gln Gly Gln Trp Pro Tyr Gly Arg Phe Leu Cys Lys
                85                  90                  95

Leu Ile Pro Ser Ile Ile Val Leu Asn Met Phe Ala Ser Val Phe Leu
            100                 105                 110

Leu Thr Ala Ile Ser Leu Asp Arg Cys Leu Val Val Phe Lys Pro Ile
            115                 120                 125

Trp Cys Gln Asn His Arg Asn Val Gly Met Ala Cys Ser Ile Cys Gly
    130                 135                 140

Cys Ile Trp Val Val Ala Phe Val Met Cys Ile Pro Val Phe Val Tyr
145                 150                 155                 160

Arg Glu Ile Phe Thr Thr Asp Asn His Asn Arg Cys Gly Tyr Lys Phe
                165                 170                 175

Gly Leu Ser Ser Ser Leu Asp Tyr Pro Asp Phe Tyr Gly Asp Pro Leu
            180                 185                 190

Glu Asn Arg Ser Leu Glu Asn Ile Val Gln Pro Pro Gly Glu Met Asn
            195                 200                 205

Asp Arg Leu Asp Pro Ser Ser Phe Gln Thr Asn Asp His Pro Trp Thr
    210                 215                 220

Val Pro Thr Val Phe Gln Pro Gln Thr Phe Gln Arg Pro Ser Ala Asp
225                 230                 235                 240

Ser Leu Pro Arg Gly Ser Ala Arg Leu Thr Ser Gln Asn Leu Tyr Ser
                245                 250                 255

Asn Val Phe Lys Pro Ala Asp Val Val Ser Pro Lys Ile Pro Ser Gly
            260                 265                 270

Phe Pro Ile Glu Asp His Glu Thr Ser Pro Leu Asp Asn Ser Asp Ala
            275                 280                 285

Phe Leu Ser Thr His Leu Lys Leu Phe Pro Ser Ala Ser Ser Asn Ser
    290                 295                 300

Phe Tyr Glu Ser Glu Leu Pro Gln Gly Phe Gln Asp Tyr Tyr Asn Leu
305                 310                 315                 320

Gly Gln Phe Thr Asp Asp Gln Val Pro Thr Pro Leu Val Ala Ile
                325                 330                 335

Thr Ile Thr Arg Leu Val Val Gly Phe Leu Leu Pro Ser Val Ile Met
            340                 345                 350

Ile Ala Cys Tyr Ser Phe Ile Val Phe Arg Met Gln Arg Gly Arg Phe
    355                 360                 365

Ala Lys Ser Gln Ser Lys Thr Phe Arg Val Ala Val Val Val Ala
    370                 375                 380

Val Phe Leu Val Cys Trp Thr Pro Tyr His Ile Phe Gly Val Leu Ser
385                 390                 395                 400

Leu Leu Thr Asp Pro Glu Thr Pro Leu Gly Lys Thr Leu Met Ser Trp
            405                 410                 415

Asp His Val Cys Ile Ala Leu Ala Ser Ala Asn Ser Cys Phe Asn Pro
```

```
                420                 425                 430
Phe Leu Tyr Ala Leu Leu Gly Lys Asp Phe Arg Lys Lys Ala Arg Gln
            435                 440                 445

Ser Ile Gln Gly Ile Leu Glu Ala Ala Phe Ser Glu Glu Leu Thr Arg
            450                 455                 460

Ser Thr His Cys Pro Ser Asn Asn Val Ile Ser Glu Arg Asn Ser Thr
465                 470                 475                 480

Thr Val

<210> SEQ ID NO 6
<211> LENGTH: 6
<212> TYPE: PRT
<213> ORGANISM: Homo sapiens

<400> SEQUENCE: 6

Phe Ile Pro Leu Ala Arg
1               5

<210> SEQ ID NO 7
<211> LENGTH: 6
<212> TYPE: PRT
<213> ORGANISM: Homo sapiens

<400> SEQUENCE: 7

Phe Trp Thr Leu Ala Arg
1               5

<210> SEQ ID NO 8
<211> LENGTH: 6
<212> TYPE: PRT
<213> ORGANISM: Homo sapiens

<400> SEQUENCE: 8

Phe Leu Thr Leu Ala Arg
1               5
```